United States Patent [19]

Fukuda et al.

[11] Patent Number: 5,521,085
[45] Date of Patent: May 28, 1996

[54] **TRANSFORMED CELL LINES PRODUCING HUMAN MONOCLONAL ANTIBODIES SPECIFIC FOR *PSEUDOMONAS AERUGINOSA* SEROTYPES**

[75] Inventors: Tamotsu Fukuda, Mobara; Yasushi Ono, Shiki; Shiro Shigeta, Fukushima; Yasuyuki Kuriowa, Mobara; Hisayoshi Ooka, Fukushima, all of Japan

[73] Assignee: Mitsui Toatsu Chemicals, Inc., Tokyo, Japan

[21] Appl. No.: 41,244

[22] Filed: Apr. 1, 1993

Related U.S. Application Data

[63] Continuation-in-part of Ser. No. 431,097, Nov. 3, 1989, abandoned, Ser. No. 602,235, Nov. 8, 1990, abandoned, and Ser. No. 879,118, May 5, 1992, abandoned, which is a continuation of Ser. No. 251,217, Aug. 8, 1988, abandoned.

[30] Foreign Application Priority Data

| Dec. 15, 1986 | [JP] | Japan | 61-296594 |
|---|---|---|---|
| Dec. 14, 1987 | [WO] | WIPO | PCT/JP87/00976 |
| Nov. 9, 1988 | [JP] | Japan | 63-281460 |
| Nov. 9, 1988 | [JP] | Japan | 63-281461 |
| Mar. 20, 1989 | [JP] | Japan | 1-66326 |
| Mar. 20, 1989 | [JP] | Japan | 1-66327 |
| Mar. 20, 1989 | [JP] | Japan | 1-66328 |
| Mar. 20, 1989 | [JP] | Japan | 1-66329 |
| May 11, 1989 | [JP] | Japan | 1-116048 |
| Mar. 19, 1990 | [WO] | WIPO | PCT/JP90/00367 |

[51] Int. Cl.$^6$ .................. C12N 5/10; C07K 16/12; C07K 16/18
[52] U.S. Cl. ............... 435/240.2; 530/388.4; 530/388.15
[58] Field of Search ............ 530/388.4, 388.15; 435/240.27, 240.2; 424/85.8, 150.1

[56] References Cited

U.S. PATENT DOCUMENTS 4,834,975  5/1989  Siadak et al. .

5,252,480  10/1993  Yokota et al. .................. 435/240.27

FOREIGN PATENT DOCUMENTS

| 0256713 | 7/1987 | European Pat. Off. . |
|---|---|---|
| 217527 | 8/1987 | European Pat. Off. . |
| 0322762 | 7/1989 | European Pat. Off. . |
| 59-296622 | 2/1984 | Japan . |
| 60-248626 | 12/1985 | Japan . |
| 61-91134 | 5/1986 | Japan . |
| 2185266 | 7/1987 | United Kingdom . |

OTHER PUBLICATIONS

Chemical Abstracts, 103, 1985, 69500a.

Chemical Abstracts, 104, 1986, 32782p.

Sawada, S. et al., J. Gen Microbiol, 133:3581–3590, 1987.

Verhoef, J. et al., Eur. J. Clin Microbiol Infect Dis, 9(4):247–250, Apr. 1990.

Cross, A. S. et al., I & I, 61(7):2741–2747, Jul. 1993.

*Primary Examiner*—David L. Lacey
*Assistant Examiner*—Susan A. Loring
*Attorney, Agent, or Firm*—Nixon & Vanderhye

[57] ABSTRACT

The present invention relates to human monoclonal antibodies capable of plurally binding with O-antigens of *Pseudomonas aeruginosa*, relates to novel parent cell lines for producing human hybridomas derived from human immunoglobulin synthesizing cells, which cell lines themselves incapable of producing human immunoglobulin and capable of fusing with human antibody-producing cells, relates to human-human hybridomas which can secrete monoclonal antibodies capable of binding with at least one of serotypes of *Pseudomonas aeruginosa*, relates to pharmaceutical compositions for prophylaxis or therapy of *Pseudomonas aeruginosa* infectious diseases, and relates to prophylactic or therapeutic methods for *Pseudomonas aeruginosa* infectious diseases.

5 Claims, 4 Drawing Sheets

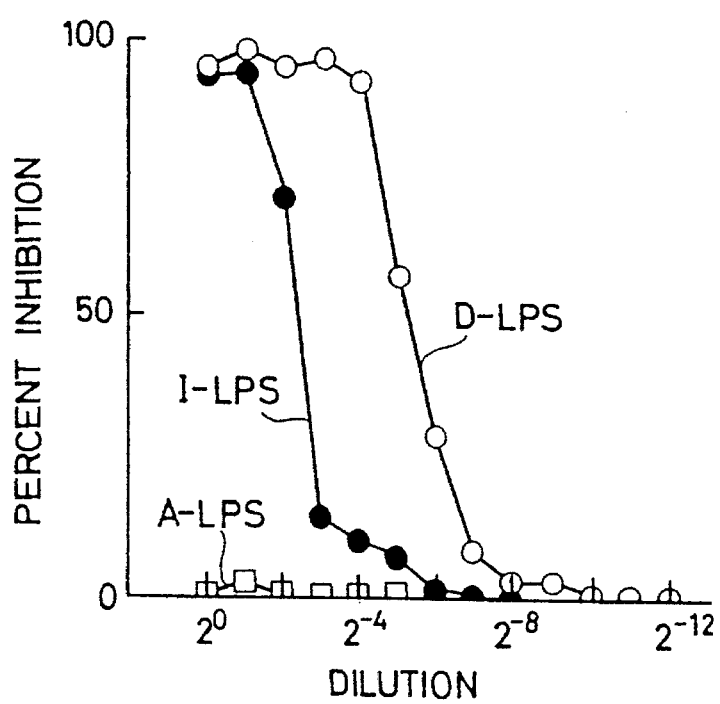
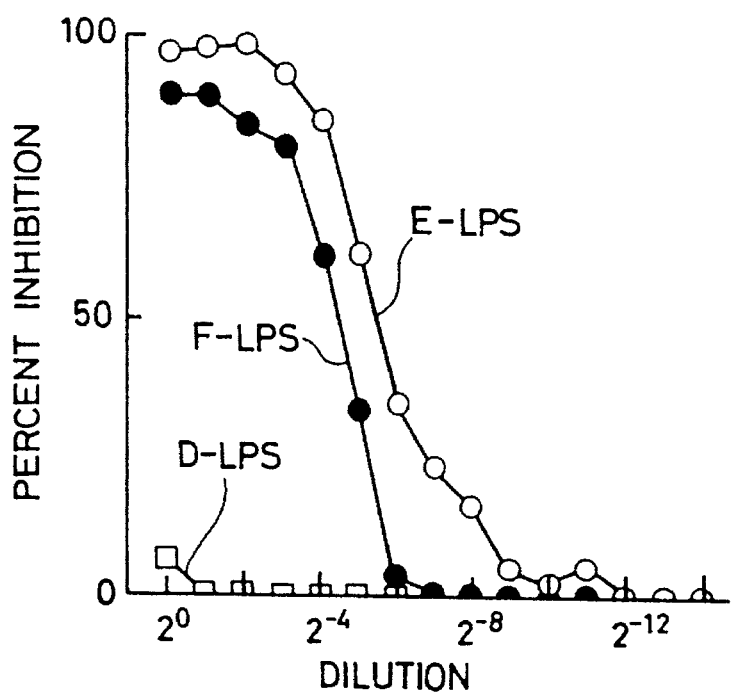

TRANSFORMED CELL LINES PRODUCING HUMAN MONOCLONAL ANTIBODIES SPECIFIC FOR *PSEUDOMONAS AERUGINOSA* SEROTYPES

This application is a continuation-in-part of application Ser. No. 07/431,097, filed Nov. 3, 1989, abandoned, and a continuation-in-part of application Ser. No. 07/602,235, filed Nov. 8, 1990, abandoned, and a continuation-in-part of application Ser. No. 07/879,118, filed May 5, 1992, abandoned which is a continuation of application Ser. No. 07/251,217, filed Aug. 8, 1988, abandoned.

FIELD OF THE INVENTION

The present invention relates to cells which produce human monoclonal antibodies to *Pseudomonas aeruginosa* each of which is single monoclonal antibody but shows affinity to O-antigens of plural *Pseudomonas aeruginosa* of different serotypes, and said antibodies, and prophylactic and therapeutic agents against *Pseudomonas aeruginosa* infectious diseases containing the same as an effective ingredient as well as preparations thereof.

Further, the present invention relates to a novel parent cell line for producing human hybridomas. More particularly, the present invention relates to novel parent cell line for producing human hybridomas derived from human immunoglobulin synthesizing cells. This cell line is itself incapable of producing human immunoglobulin and is capable of fusing with human antibody-producing cells. The cell line is selective to human hybridomas and is capable of imparting high antibody productivity to human hybridomas.

Furthermore, the present invention relates to a human-human hybridoma cell line which can stably supply in large quantity human monoclonal antibodies having reactivity with at least one serotype bacteria of the major causative bacteria of infectious diseases with *Pseudomonas aeruginosa*. The present invention also relates to human monoclonal antibodies produced by the human-human hybridoma cell line and to pharmaceutical compositions for prophylaxis and treatment of *Pseudomonas aeruginosa* infectious diseases using the human monoclonal antibodies as an effective ingredient. Methods of treating these diseases are also disclosed.

PRIOR ART

*Pseudomonas aeruginosa* is widely present in the natural world and can be found in drainages and in addition, the oral cavities or intestines of man and animals in a high frequency. This bacterium exhibits its pathogenicity in patients with general infectious diseases caused by virulence of this bacterium per se but rather in patients with reduced resistance to infection, namely, a cancer patient, a patient under immunosuppressive therapy, a transplant recipient, a patient with burn, a neonate and the like.

*Pseudomonas aeruginosa* infectious diseases would be infectious diseases currently considered to be most difficult for treatment. That is, *Pseudomonas aeruginosa* not only shows resistance to almost all antibiotics conventionally used hitherto but also tends to readily induce resistance to antibiotics developed in recent years. Taking the limit of antibiotic therapy into account, therefore, prophylaxis and therapy have been investigated, aiming at enhancing an ability capable of treating *Pseudomonas aeruginosa* in a host. One is investigation on development of vaccine but it is difficult to expect an immediate effect on the patient who has already been infected. On the other hand, preparations comprising human immunoglobulin purified from healthy donors' sera or plasma, and its chemically modified product as an effective ingredient have been often used for treatment of *Pseudomonas aeruginosa* infectious diseases in recent years. Among antibodies contained in these preparations, however, an amount of an antibody having affinity to *Pseudomonas aeruginosa* and effective for the treatment is not constant and its amount is small so that many investigators doubt the prophylactic and therapeutic effect of these preparations. For this reason, development of human monoclonal antibodies effective in a small dose has been urgently desired.

On the other hand, as surface antigens of *Pseudomonas aeruginosa*, it is known that outer membrane protein (OMP), polysaccharide antigen derived from flagellum or slime and lipopolysaccharide (hereafter simply referred to as LPS) antigen are present. Among them, LPS is composed of O-polysaccharide (hereafter sometimes referred to as O-antigen) that is a serotype specific epitope, and lipid A and a core region which are a basic structure common to gram negative bacteria. The O-specific polysaccharide chain is composed of repetitive oligosaccharides. Serological classification of *Pseudomonas aeruginosa* is made by immunological property of this O-specific polysaccharide chain. However, even now, there is much argument about serological classification of *Pseudomonas aeruginosa*. In Japan, serological classification of the Serotyping Committee for the Japan *Pseudomonas aeruginosa* Society in which *Pseudomonas aeruginosa* is classified into 13 kinds from group A to group M has been widely used [Homma, Japan J. Exp. Med., 46, 329–336 (1976)]. The serological classification of the Serotyping Committee for the Japan *Pseudomonas aeruginosa* Society is compared with other classification, as described below.

| Comparison of serological classification of the Serotyping Committee for the Japan *Pseudomonas aeruginosa* Society with other classification | | | |
|---|---|---|---|
| Serotyping Committee for the Japan *Pseudomonas aeruginosa* Society | Homma | Lanyi | Fisher |
| A | 1 | 1 | — |
| B | 2 | 3 | 3 |
|   | 7 |   | 7 |
|   | 13 |   |   |
|   | 16 |   |   |
| C | 3 | 5 | 6 |
| D | 4 | 10 | — |
| E | 5 | 7 | 2 |
| F | 6 | 11 | — |
| G | 8 | 4 | 1 |
| H | 9 | 2 | 5 |
| I | 10 | 6 | 4 |
| J | 11 | 12 | — |
| K | 12 | — | — |
| L | 14 | 13 | — |
| M | 15 | 9 | — |
|   | 17 |   |   |
|   | — | 8 | — |

In recent years, a primary structure of O-specific polysaccharide chain has been clarified in proper course [for example, Kropinski et al., Antibiot. Chemother., 36, 58–73 (1985)] and there is a possibility that a new classification may be adopted in the future. It is known that an antibody to O-specific polysaccharide chain of LPS of *Pseudomonas aeruginosa*, namely, an antibody to *Pseudomonas aeruginosa* O-antigen, has a potent bacteriolytic or opsonic activity via the complement system. Aiming at obtaining human monoclonal antibodies effective for prophylaxis and therapy of *Pseudomonas aeruginosa* infectious diseases, the present inventors made extensive investigations and found for the first time that human monoclonal antibodies to serotype antigens of *Pseudomonas aeruginosa*, namely, monoclonal antibodies capable of serotype specifically reacting with *Pseudomonas aeruginosa*, possess a very high protective activity against *Pseudomonas aeruginosa* infection of the same serotype and came to accomplish an invention described in Published Unexamined Japanese Patent Application No. 248626/1985. However, as is described in Published Unexamined Japanese Patent Application Nos. 152280/1986 and 155398/1986 which were subsequently published and relate to protection of human monoclonal antibodies to O-specific polysaccharide chains of LPS of *Pseudomonas aeruginosa* from infection, serotype specific human monoclonal antibodies reacting with Pseudomonas aeruginosaspecifically react only with *Pseudomonas aeruginosa* of single serotype and have a protective activity against *Pseudomonas aeruginosa* infection of the same serotype but has no protective activity against *Pseudomonas aeruginosa* infection of other serotypes.

On the other hand, monoclonal antibodies to outer membrane protein of *Pseudomonas aeruginosa* [Sawada et al., J. Infect. Dis., 150, 570–576 (1985), Yoshiaki NAKAMURA et al., Jpn. J. Bacteriol., 39, 337 (1984)] or human monoclonal antibodies to common polysaccharides of *Pseudomonas aeruginosa* [Sawada et al., J. Infect. Dis., 150, 1290–1299 (1985)] are all low in their protective activity against *Pseudomonas aeruginosa* infection.

In 1975, Köhler and Milstein selected and isolated for the first time a single mouse hybridoma capable of producing mouse monoclonal antibody by using mouse myeloma cell line P3X63Ag8 as a parent cell line, fusing the parent cells with mouse spleen cells and then culturing the fused cells in selective culture medium containing aminoputerine, hypoxanthine and thymidine [G. Köhler and C. Milstein, Nature, 256, 495 (1975)]. Since then attempts have been made to produce a single human hybridoma capable of producing human monoclonal antibody by using as the parent cell line a mouse myeloma cell line, a hetero myeloma cell line, which is a hybridoma between mouse myeloma cell and human cell, a human myeloma cell line or a human lymphoblast cell line and fusing the parent cell line with human antibody-producing cell. However, in the case of using as the parent cell line a mouse myeloma cell line or a hereto myeloma cell line and fusing the parent cell line with a human antibody-producing cell, the thus produced human hybridomas also synthesize and secret mouse protein (an inwanted antigen) in addition to human antibodies. Therefore, it is not necessarily appropriate to use the resulting hybridomas for producing human monoclonal antibodies for administration to humans.

On the other hand, an attempt to produce human hybridomas by fusion between a parent cell line having human chromosome alone and a human antibody-producing cell has been reported by Olsson and Kaplan as well as Croce et al. in 1980 [L. Olsson and H. S. Kaplan, Proc. Natl. Acad. Sci., 77 5429 (1980), C. M. Croce et al., Nature 288, 488 (1980)]. Then many reports on the production of hybridomas followed. However, in parent cell lines suited for producing human hybridomas capable of imparting high antibody productivity to the resulting human hybridomas, the cells themselves synthesize human immunoglobulin, though its degree is different. For example, KR-12 having selectivity to a human hybridoma between human myeloma cell line RPMI 8226 and human lymphoblast cell line KR-4 is currently one of a few parent cell lines suited for producing human hybridomas, however it senthesizes and secretes heavy chain (human gamma chain) and light chain (human lambda chain, human kappa chain) of immunoglobulins derived-from the respective cell lines [ Japanese Patent Laying-Open No. 61-128886] (a Japanese patent laying-open means the publication of an application). As parent cell lines for producing human hybridomas derived from human myeloma cell lines or human lymphoblasts, several patent applications have been filed, directed to ATCC CRL 8032 and ATCC CRL 8038 [Japanese Patent Laying-Open No. 57-126424], WI-L2-729 HF2 [ Japanese Patent Laying-Open No. 57-208987], ATCC CRL 8083 [ Japanese Patent Laying-Open No. 58-501257], ATCC CRL 8147 [ Japanese Patent Laying-Open No. 59-66883], UC 729-6 [U.S. Pat. No. 4,451,570], ATCC CRL 8221 [ Japanese Patent Laying-Open No. 59-198970], LTR228 [Japanese Patent Laying-Open No. 60-251881], HIH/TO1 [Japanese Patent Laying-Open No. 62-155083], and ATCC HB 9320 [Japanese Patent Laying-Open No. 64-60373]. Some of these parent cell lines do not secrete human immunoglobulin but all of them synthesize human immunoglobulin.

For this reason, attempts have been made to mutate a cell line incapable of producing human immunoglobulin from the existing parent cell line suited for production of human hybridomas. For example, "Monoclonal Antibody Production Techniques and Applications" authored and edited by L. B. S. Chook (1987), MARCEL DEKKER, INC., page 12, describes isolating cells incapable of expressing human immunoglobulin on the cell surface by reacting anti-human immunoglobulin antibody with a cell mass mutated from KR-12 in the presence of a complement to kill cells expressing human immunoglobulin on the cell membrane surface followed by cloning manipulation using cell sorting and limiting dilution. However, cells incapable of synthesizing human immunoglobulin could not be obtained.

As a parent cell line incapable of producing human immunoglobulin, a patent application has been filed directed to HOMO7 [Japanese Patent Laying-Open No. 63-185374]. However, no working example is found on the amount of antibodies secreted by human hybridoma produced. The presence of a parent cell line derived from cells other than human myeloma cells or human lymphoblasts or their human hybridomas is also reported. However, there is no description of the amount of antibodies secreted by human hybridomas produced in patent applications directed to Burkitt's lymphoma-derived parent cell lines [Japanese Patent Laying-Open Nos. 60-141285 and 61-242575]. In a patent application directed to a human melanoma cell-derived parent cell line [Japanese Patent Laying-Open No. 59-132885], no working example is found on the production of human hybridomas.

*Pseudomonas aeruginosa* infectious diseases are opportunistic infectious diseases frequently caused in patients with various basal diseases or patients who have been given immunosuppressive drugs. *Pseudomonas aeruginosa* infectious diseases are currently considered to be infectious diseases which are most difficult to treat. That is, *Pseudomonas aeruginosa* not only shows resistance to almost all antibiotics conventionally used, but also has a strong tendency to readily induce resistance to antibiotics developed in recent years. For this reason, investigations have been made on both prophylaxis and therapy, to enhance the ability of the host to kill *Pseudomonas aeruginosa*.

In recent years, immune serum globulins having as the effective ingredient human immunoglobulin purified from healthy donors' sera or plasma, or its chemically modified derivative have often been used for the treatment of *Pseudomonas aeruginosa* infectious diseases. However, among the antibodies contained in these immune serum globulins, the amount of antibody having affinity to *Pseudomonas aeruginosa* and effective for the treatment desired is not certain or its content is small. Thus, the prophylactic and therapeutic effects of these immune serum globulins are often problematic. There is thus a need to develop human monoclonal antibodies effective in small doses for this purpose.

*Pseudomonas aeruginosa* is classified by its serotype, using an immune antibody capable of recognizing the O-polysaccharide side chain on the lipopolysaccharide (hereafter simply referred to as LPS) present on the outer membrane, i.e., an antibody to *Pseudomonas aeruginosa* serotype-specific O-antigen. The serotype classification of *Pseudomonas aeruginosa* is currently a topic of discussion. In Japan, serologic classification of the Serotyping Comittee for the Japan *Pseudomonas aeruginosa* Society [Homma, Japan J. Exp. Med., 46, 329–336 (1976)] has been widely used which classifies *Pseudomonas aeruginosa* into 13 serotypes from group A to group M. In this specification and the claims that follow we use the serologic classification of the Serotyping Committee for the Japana *Pseudomonas aeruginosa* Society. Each serotype of *Pseudomonas aeruginosa* is isolated from patients with *Pseudomonas aeruginosa* infectious diseases in the clinics with a constant ratio. It is known that a ratio of 5 serotypes of groups A, B, E, G and I is predominant in the 13 serotypes.

On the other hand, mouse monoclonal antibody to *Pseudomonas aeruginosa* has been produced by the mouse-mouse hybridoma technique developed by Köhler and Milstein [Köhler and Milstein, Nature, 256, 495–497 (1975)]. Since then [for example, Hancock et al., Infect. Immun., 37, 166–171 (1982)], the technique has been applied to serotype classification for example, Meiji Seika, EP 101039] or used for basic research for a survey of monoclonal antibodies useful for protection from infections, etc.

Sadoff et al. report that mouse monoclonal antibody to the O-polysaccharide side chain on the serotype-specific LPS molecule of *Pseudomonas aeruginosa* has a high protection activity against lethal challenge with bacteria of the corresponding serotype in the experimental infection using mice [Sadoff et al., Abstracts of the 1982 Interscience Conference on Antimicrobial Agents and Chemotherapy, No. 253 (1982)]. In the following reports, the effectiveness of mouse or human monoclonal antibodies to serotype-specific O-antigen of *Pseudomonas aeruginosa* is shown in in vivo or in vitro tests [for example, Sawada et al., J. Infect. Dis., 150, 570–576 (1984); Yoshiaki Nakamura et al., Japanese Journal of Bacteriology, 39, 337 (1984); Pennington, Infect. Immun., 54, 239–244 (1986); Suzuki et al., Microbiol. Immunol, 31, 959–966 (1987), Zwermik et al., Infect. Immun., 56, 1873–1879 (1988)]. Furthermore, application of serotype-specific human monoclonal antibodies to prophylaxis and therapy of *Pseudomonas aeruginosa* infectious diseases has been described in a patent application directed to antibodies capable of independently recognizing the O-polysaccharide side chain on the serotype-specific LPS molecule [Japanese Patent Application Laid-Open No. 60-248626] and a patent application directed to antibodies capable of recognizing a plurality of O-polysaccharide side chains in common [International Patent Application Laid-Open No. WO 88/04669], by the present inventors as well as in other patent applications [Genentech Systems Corporation, EP 163493 and BE 905890; Teijin Limited, WO 86/03754; Wakunaga pharmaceutical Co., Ltd., Japanese Patent Application Laid-Open No. 61-091134; Merck & Company Incorporated, EP 256713].

PROBLEMS TO BE SOLVED BY THE INVENTION

As described above, human monoclonal antibodies to O-antigen of *Pseudomonas aeruginosa* have a very high activity as protective antibodies, as compared to human monoclonal antibodies to other antigens of *Pseudomonas aeruginosa* but are effective only for *Pseudomonas aeruginosa* infection of the corresponding serotype. According to the serological classification of the Serotyping Committee for the Japan *Pseudomonas aeruginosa* Society, O-antigen is classified into 13 groups and the serotype of *Pseudomonas aeruginosa* clinically isolated also covers all of these serotype bacteria, although there is a difference in frequency. Therefore, in order to generally use human monoclonal antibodies to O-antigen as a prophylactic and therapeutic agent against *Pseudomonas aeruginosa* infectious diseases, it is necessary to prepare a preparation by combining several to ten-odd kinds of antibodies. However, as the number of monoclonal antibodies to be used in combination increases, complexity in quality control of the preparation, etc. increases. In order to reduce such a complexity, it is desired to obtain human monoclonal antibodies to O-antigens showing cross reactivity with *Pseudomonas aeruginosa* of a plurality of different serotypes and having a potent protective activity against infectious diseases caused by *Pseudomonas aeruginosa* of a plurality of different serotypes. However, there is no successful report on this. In addition, it is also an important subject to prepare a cell line capable of producing the aforesaid human monoclonal antibodies in a large quantity stably, which can be safely injected to human.

Where the yield of antibodies produced from the human hybridomas produced is low, costs for producing of antibodies are high, so that industrial utilization is generally considerably limited. For this reason, a parent cell line that cannot impart high antibody productivity to the desired human hybridoma so produced is of little value for industrial utilization.

On the other hand, where a parent cell line itself synthesizes human immunoglobulin, the resulting human hybridoma synthesizes human immunoglobulin derived from human antibody-producing cells and human immunoglobulin derived from the parent cell line. Therefore, there is a possibility that, on occasion, a plurality of partially recombined antibodies might be secreted. In addition, the binding specificity of the antibody to antigen is derived from the structure of both heavy chain and light chain of human immunoglobulin in the variable amino acid sequence region. Accordingly, where the heavy chains and light chains derived from human antibody-producing cells and the parent cell line are recombined with each other, it is presumed that the binding activity or specificity of the secreted antibodies to the desired antigens might be reduced. In fact, Shinmoto et al. reported that the human hybridoma between the parent cell line HO323 capable of synthesizing but incapable of secreting human IgM and human lymphocyte produces the antibody in which the heavy chain and light chain of human IgM derived from the parent cell line are recombined with the heavy chain and light chain of human IgA derived from the human lymphocyte [H. Shinmoto et al., Agric. Biol.

Chem., 50, 2217 (1986)]. It was reported that the human hybridoma between KR-12 and human IgM-producing cell line having reactivity with tetanus toxin secreted almost the same amount of human IgG and human IgM and furthermore, human IgM alone out of the two antibodies has a reactivity with tetanus toxin [D. Kozbor et al., J. Immunol., 133, 3001 (1984)].

In general, human monoclonal antibody is produced by infecting human B cells with Epstein-Barr virus (hereafter simply referred to as EB virus) to convert the B cells into EB virus transformed cells or by fusing human antibody producing cells such as B cells and a parent cell line capable of infinite proliferation to convert it into a human-mouse hetero hybridoma or human-human hybridoma.

In the transformant produced by EB virus transformation, the amount of antibodies produced is generally poor and subculture stability is inferior. Furthermore, due to relatively high auxotrophy, the transformant is not suited for mass production using a serum-free medium. In the case of fusing with human antibody producing cells using mouse myeloma as the parent cell line, the produced human-mouse hereto hybridoma synthesizes and secretes mouse protein together with human antibodies and hence, it is not always suitable to use the transformant as the cell line for producing human monoclonal antibody administered to a human. Further, in the case of producing human-human hybridoma by fusion with human antibody producing cells using cells having a human chromosome alone and capable of infinite proliferation as the parent cell line, some problems are encountered. For example, the fusion efficiency of a human myeloma-derived parent cell line with human antibody producing cells is poor. Although the fusion efficiency of EB virus transformed cells-derived parent cell line with human antibody producing cells is relatively high, most of the resulting human-human hybridomas also produce antibodies having no antigen specificity and at the same time, produce only a minor amount of antibodies. The human-human hybridomas produced by fusion of human antibody producing cells and the parent cells derived from the hybridoma between human myeloma cells and EB virus transformed cells produce a relatively high amount of antibodies, but the possibility of simultaneously producing antibodies having no antigen specificity is not eliminated.

MEANS FOR SOLVING THE PROBLEMS

The present inventors have made extensive investigations aiming at obtaining a cell line capable of secreting a single human monoclonal antibody having a high protective activity and capable of recognizing *Pseudomonas aeruginosa* having a plurality of serotypes in common and have come to accomplish the present invention.

The present invention is to obtain a self-reproducing cell line capable of continuously producing a human monoclonal antibody capable of reacting with a plurality of different O-antigens of *Pseudomonas aeruginosa* in common, namely, a human monoclonal antibody capable of plurally reacting with O-antigens of *Pseudomonas aeruginosa* and to achieve prophylaxis and therapy of *Pseudomonas aeruginosa* infectious diseases in human and animal using the human monoclonal antibody produced by this cell line singly or in combination as a prophylactic and therapeutic agent against *Pseudomonas aeruginosa* infectious diseases. Human antibody producing cells (B cells) are infected with Epstein-Barr virus (hereafter simply referred to as EB virus) to effect transformation (hereafter referred to as EB virus transformation); alternatively, human antibody producing cells are fused to human or animal derived cells capable of indefinite growth, for example, tumor cells, to obtain colonies capable of indefinite growth. From the colonies, a cell line capable of producing a single human monoclonal antibody having a reactivity with a plurality of *Pseudomonas aeruginosa* of different serotypes is selected by screening using the enzyme immunoassay and cloning. Next, this cell is cultured and a single human monoclonal antibody having a reactivity with *Pseudomonas aeruginosa* having different serotypes is purified from the culture solution in a conventional manner, for example, column chromatography, electrophoresis, precipitation, extraction, etc. The purified human monoclonal antibody can be provided as liquid preparations or lyophilized preparations for prophylaxis and therapy of *Pseudomonas aeruginosa* infectious diseases, singly or after adding optional additive thereto.

The present inventors have made extensive investigations with an attempt to produce a parent cell line derived from human for human hybridomas imparting high antibody productivity to the produced human hybridomas yet the cell per se being incapabale of synthesizing human immunoglobulin. As a result, applicants have successfully isolated a novel parent cell line for human hybridoma which is a mutant cell line derived from a human hybridoma capable of synthesizing and secreting heavy chain (human gamma chain) and light chain (human lambda chain, human kappa chain) human immunoglobulin but does not synthesize heavy chain (human gamma chain), does not synthesize heavy chain (human gamma chain) and light chain (human lambda chain) or, does not synthesize heavy chain (human gamma chain) and light chain (human lambda chain, human kappa chain) of immunoglobulins.

Köhler reported that a mouse hybridoma capable of secreting a plurality of different antibodies was produced and the mechanism on deletion of expression of the heavy chain and light chain in mouse immunoglobulin was examined. As the result, deletion in expression of the heavy chain of mouse immunoglobulin was noted mainly due to chromosomal deficiency [G. Köhler, Proc. Natl. Acad. Sci., 77, 2197 (1980)]. On the other hand, the present inventors found in the past that when a mouse hybridoma between a mouse myeloma cell and a mouse spleen cell was repeatedly freeze storaged and subcultured continuously, mouse hybridomas maintaining a high proliferation characteristics as myeloma cells are expressed with high frequency, notwithstanding that they lost the ability to synthesize and secrete antibodies.

Therefore, after inducing mutation on the known and generally available human hybridoma cell line ATCC CRL 8658, a novel single cell line was produced by screening cells that maintain the proliferation ability but do not synthesize or secrete the heavy chain (human gamma chain) of human immunoglobulin or, both or either one of the heavy chain (human gamma chain) and light chain (human lambda chain, human kappa chain) of human immunoglobulin. We have confirmed that this novel cell line is capable of fusing with human antibody-producing cells, maintains the selectivity characteristic of human hybridomas and, unlike the parent cell line used to induce the present parent cell line, this human hybridoma synthesizes and secretes human immunoglobulin derived from the human antibody-producing cells. It has thus been found that the present parent cell line is a parent cell line useful for the production of human hybridomas suited for practically and efficiently producing human monoclonal antibodies.

What is particularly important in the present invention is the successful isolation of a parent cell line that does not synthesize the heavy chain (human gamma chain), does not synthesize the heavy chain (human gamma chain) and the light chain (human lambda chain), or does not synthesize the heavy chain (human gamma chain) and the light chain (human lambda chain, human kappa chain), as the result of mutation for the purpose of obtaining a cell line from which only the undesired characteristic that the parent cell line itself synthesizes human immunoglobulin although it maintains the ability of imparting high antibody productivity to the human-hybridoma with human antibody-producing cells. It is further been confirmed that the novel parent cell line of this invention is capable of fusing with human lymphoblasts, can impart high human antibody productivity to the exemplified human hybridomas and can produce only the heavy chain derived from human lymphoblasts as the heavy chain.

Therefore, an object of the present invention is to provide a parent cell line for producing a cell line capable of industrial production of human monoclonal antibodies which can be used over wide areas such as prophylaxis, treatment, diagnosis, etc. of various diseases.

A characterizing feature of the present invention lies in producing cells themselves incapable of synthesizing human immunoglobulin from cells that are capable of synthesizing human immunoglobulin. The starting materials are not limited only to a particular human hybridoma cell line ATCC CRL 8658 between human myeloma cell line RPMI 8226 and human lymphoblast cell line GM 1500. Various human myeloma cells, human lymphoblasts or newly created human hybridomas by fusion of these cells are also usable. In addition, RPMI 8226 or human hybridomas derived from a cell line of which the human immunoglobulin synthesizing ability of RPMI 8226 is deleted, GM 1500 or human hybridomas derived from a cell line of which human immunoglobulin synthesizing ability of GM 1500 is deleted, can also be used. In addition to mutants derived therefrom, human hybridomas produced from a plurality of generally available cells can be appropriately selected.

The present inventors have found human-human hybridomas capable of producing human monoclonal antibodies having reactivity with at least one serotype bacteria which are the major causative bacteria of *Pseudomonas aeruginosa* infections; that the human-human hybridomas can be stably proliferated in various media and can maintain a relatively large quantity of antibody production over long periods of time; and further that these human-human hybridomas are cultured and human monoclonal antibodies having reactivity with at least one serotype bacteria which are the major causative bacteria of *Pseudomonas aeruginosa* infections can be prepared from the culture.

Based on these results, the present inventors have examined the protective activity of these antibodies produced by the human-human hybridomas against *Pseudomonas aeruginosa* infections and have come to accomplish the present invention.

The term "the major causative bacteria" as used in this application refers to bacteria of 5 serotypes of groups A, B, E, G and I in the serologic classification by the Serotyping Comittee for the Japan *Pseudomonas aeruginosa* Society.

The term "human-human hybridoma" as used in this application refers to hybridomas having a human chromosome alone produced by fusing the parent cell line capable of infinite proliferation and having a human chromosome alone with human antibody producing cells.

The term "selection characteristic" as used herein refers to the chemical or physical properties of the parent cell line which enables to select the produced hybridoma from the unfused cells. For example, in the case of using a parent cell line resistant to 8-azaguanine or 6-thioguanine and ouabain as the selection characteristic, only the hybridoma derived from the human antibody producing EB virus transformed cells can survive in the medium containing hypoxanthine, azaserine and ouabain.

A parent cell line having the selection characteristic described above can be appropriately selected. Furthermore, the human antibody producing cells capable of reacting with *Pseudomonas aeruginosa* can be appropriately selected from human B cells and cells derived therefrom.

Hereafter the present invention is described by referring to the case of producing a human-human hybridoma using as the parent cell line having a human chromosome alone and infinite growth ability and resistance to 8-azaguanine and ouabain and using as the human antibody producing cells human antibody producing EB virus transformed cells having reactivities respectively with groups A, B, E, G and I of *Pseudomonas aeruginosa* in the serologic classification by the Serotyping Comittee for the Japan *Pseudomonas aeruginosa* Society, through fusion between both cells.

BRIEF DESCRIPTION OF THE DRAWINGS

FIGS. 1 through 7 drawings show results obtained by examining cross reactivity of human monoclonal antibodies with O-antigens of *Pseudomonas aeruginosa* by inhibition tests of LPSs of a variety of serotype *Pseudomonas aeruginosa* on binding of human monoclonal antibody to LPS. FIG. 1 shows LPSs of group D and group I *Pseudomonas aeruginosa* inhibit the binding of HPs1. FIG. 2 shows LPSs of group E and group F *Pseudomonas aeruginosa* inhibit the binding of HPs2. FIG. 3 shows LPSs of group A and group L *Pseudomonas aeruginosa* inhibit the binding of HPs4. FIG. 4 shows LPSs of group G and group H *Pseudomonas aeruginosa* inhibit the binding of HPs5. FIG. 5 shows LPSs of group E and group F *Pseudomonas aeruginosa* inhibit the binding of HPs6. FIG. 6 shows LPSs of group A and group F *Pseudomonas aeruginosa* inhibit the binding of HPs7. FIG. 7 shows LPSs of group E and group F *Pseudomonas aeruginosa* inhibit the binding of HPs8.

DETAILED DESCRIPTION OF THE INVENTION

1. *Pseudomonas aeruginosa* used

Figure 3:
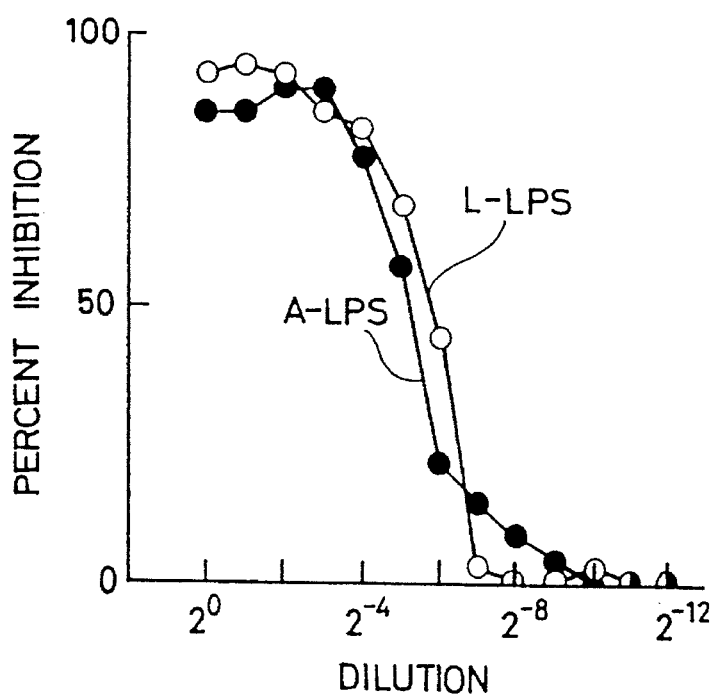

For convenience, classification of *Pseudomonas aeruginosa* follows the serological classification of the Serotyping Committee for the Japan *Pseudomonas aeruginosa* Society in the present invention. Strains belonging to group A to group M which are shown in Table 1 are used.

Most strains belonging to group A to group M can be acquired from American Type Culture Collection (ATCC) and University of Tokyo, Institute of Medical Science.

2. Preparation of human monoclonal antibodies

The human monoclonal antibodies capable of plurally reacting with O-antigens of *Pseudomonas aeruginosa*, namely, human monoclonal antibodies to O-specific polysaccharide chain of LPS of *Pseudomonas aeruginosa*, according to the present invention can b4 prepared by the EB virus transformation method, the cell fusion method, etc.

The production of the human monoclonal antibodies according to the present invention by the EB virus transformation method can be performed by (1) preparing human antibody producing cells (human B cells), (2) infecting human antibody producing cells with EB virus to effect transformation, (3) detecting secretion of antibodies capable of reacting with plural *Pseudomonas aeruginosa* of different serotypes, (4) selecting a single cell line from the transformed cell colony (this operation is sometimes simply referred to as cloning hereinafter), (5) culturing the cell line and (6) purifying human monoclonal antibody from the culture.

Next, each step will be described in detail.

(1) Preparation of antibody producing cells

Human antibody producing cells (B cells) used in the method of the present invention can be obtained from peripheral blood, lymph node, tonsil or spleen collected from healthy donor capable of producing antibodies to *Pseudomonas aeruginosa*, or patient with *Pseudomonas aeruginosa* infectious disease past history, or from cord blood upon delivery, etc., by a known method. Isolation and concentration of human antibody producing cells (B cells) obtained from, for example, blood, tissues described above, etc. can be efficiently carried out by the density gradient centrifugation method using cell separation media such as Ficoll-Conray, etc., the E rosette formation method, the panning method, etc. in combination.

(2) Transformation

Transformation of human antibody producing cells (B cells) with EB virus can be carried out in a manner similar to known methods [for example, Nature, 269, 420–422 (1977)].

B95-8 cells (marmoset leucocyte derived cells capable of producing infectious EB virus) are cultured in 20% fetal calf serum (hereafter merely referred to as FCS)-containing RPMI 1640 medium (hereafter sometimes merely referred to as culture solution). The culture supernatant on the 7th day close to the stationary phase is centrifuged to obtain a vital solution. [Proc. Jap. Soc. Immunol., 4, 399–401 (1974)]. Next, human antibody producing cells (B cells) obtained in (1) are centrifuged and the supernatant is removed by suction and the viral solution is added to the thus obtained pellets to disperse them, followed by incubation at 37° C. for an hour in the presence of 5% carbon dioxide. After incubation, centrifugation is performed. After removing the supernatant by suction, the culture solution is added to the pellets in a cell density of $1 \times 10^5$ to $5 \times 10^5$/ml to disperse the cells. The cell dispersion is separately charged in each well of a 24 well culture plate or a 96 well culture plate followed by incubation at 37° C. for 2 to 4 weeks in the presence of 5% carbon dioxide. During the course of incubation, it is desired to replenish a half of the culture solution with a fresh culture solution.

(3) Detection of antibodies

Detection of the antibodies having reactivity with plural *Pseudomonas aeruginosa* of different serotypes can be performed by ordinary radio immunoassay, enzyme immunoassay, etc. [book entitled "Monoclonal Antibody", page 144, published by Kodansha Publishing Co., Ltd. (1983), and others]. In the present invention, the enzyme immunoassay is used. That is, there is used as a simple method the dot-immunobinding assay [hereafter simply referred to as DIBA, Anal. Biochem., 119, 142–147 (1982)] which comprises previously fixing 0.3% formalinized bacterial cells or LPSs of plural *Pseudomonas aeruginosa* of different serotypes to membrane filter, reacting the cell culture supernatant in a container for a definite time period, then reacting with enzyme conjugated rabbit anti-human antibody and determining the presence or absence of production and its amount of antibody produced by a degree in color formation of substrate through enzymatic reaction. If necessary, immunoglobulin type can be determined using an enzyme conjugated anti-human antibody specific to human immunoglobulin type.

(4) Cloning

A well in which the objective antibody is present is selected by testing the culture supernatant of each well where cell growth colonies have been noted, by the enzyme linked immunosorbent assay (hereafter simply referred to as ELISA method) described above, etc. Then, the cells in this well are subjected to cloning by the soft agar method [book entitled "Advanced Tissue Cultures", page 289, published by Soft Science Publishing Co. (1985), and others] or by the limiting dilution method [book entitled "Monoclonal Antibody", page 73, published by Kodansha Publishing Co., Ltd. (1983), and others]. Further after growth of the cells by cloning is noted, assay is again performed by ELISA described above. By cloning one to several times, a monoclonal cell line capable of secreting the objective antibody alone can be obtained.

(5) Culture of established cell line

The cell line established by the method of (4) can be cultured using ordinary medium. For example, the culture solution described above, ordinary low serum medium or serum free medium can be appropriately used.

(6) Purification of human monoclonal antibodies

Purification of the human monoclonal antibodies in accordance with the present invention from the culture solution can be performed by known methods in combination, for example, non-specific purification methods such as the ammonium sulfate precipitation method, the gel filtration method, the ion-exchange resin chromatography method, etc., the affinity chromatography method using a carrier having fixed thereto an antigen or a substance (for example, protein A, anti-human immunoglobulin antibody, etc.) having affinity to human monoclonal antibodies, or the like.

Production of the human monoclonal antibodies of the present invention according to the cell fusion method can be carried out in a manner similar to known methods [book entitled "MONOCLONAL ANTIBODIES", page 363, published by Plenum Press and others]. That is, the human monoclonal antibodies can be produced by (1) preparing human antibody producing cells (human B cells, etc.), (2) cell fusing the human antibody producing cells to cells capable of indefinite growth, (3) detecting secretion of antibodies capable of reacting with plural *Pseudomonas aeruginosa* of different serotypes, (4) selecting a single cell line from the hybridoma colonies, (5) culturing the cell line and then (6) purifying the human monoclonal antibodies from the culture.

(1) Preparation of antibody producing cells

As the antibody producing cells used for cell fusion, antibody producing cells similar to those as in the EB virus transformation method described above can be used. In addition, EB virus transformed cell colonies obtained by the EB virus transformation method described above and capable of secreting the objective antibody prior to cloning, or a single EB virus transformed cell line obtained by cloning can also be used. Further, human antibody producing cells (B cells) are cultured in culture solution supplemented with pokeweed mitogen (PWM) for several days to proliferate the antibody producing cells, which can also be provided for cell fusion.

(2) Cell fusion

In production of human B cell hybridomas, it is preferred to use human derived myeloma cells, myeloma like cells, lymphoblast cells or lymphoblast like cells capable of indefinite growth and sensitive to culture solution containing hypoxanthine, aminopterine and thyroidine (HAT medium) or culture solution containing hypoxanthine and azaserine (HA medium) as partner cells. Mouse myeloma cells, etc. sensitive to HAT medium can also be used as partner cells.

For example, mouse myeloma cells, P3-NS1/1-Ag4.1 (abbreviation, NS-1) as partner cells are mixed with cells of a well in which production of the objective antibody has been noted after transformation with EB virus or with antibody producing cells isolated from peripheral blood, etc. in a ratio of approximately 1:1 to 1:10. A medium (RPMI 1640 medium containing 50% polyethylene glycol and 10% dimethylsulfoxide, or the like) for cell fusion is added to the mixture followed by fusing cells by known methods. Then, the cells are dispersed in HAT-ouabain culture solution (culture solution further containing ouabain in the aforesaid HAT medium, HAT-O medium) suited for growth of the fused hybridoma alone in a cell density of $1 \times 10^5$ to $5 \times 10^6$/ml. The cell dispersion is separately charged in a 24 well or 96 well culture plate followed by incubation at 37° C. for about 2 to about 4 weeks in the presence of 5% carbon dioxide. During course of the incubation, it is desired to replenish a half of the HAT-O medium with a fresh HAT-O medium every 3 to 5 days. In this case, when mouse peritoneal exudate cells, etc. are co-present as feeder cells, growth of the hybridoma can be accelerated.

Further the hybridoma can be produced by mixing human lymphoblast like cells, MHP-315 as partner with EB virus transformed cell line or antibody producing cells isolated from peripheral blood, etc. in a ratio of approximately 1:1 to 1:10, performing cell fusion as described above, then dispersing the cells in HA-ouabain culture solution (culture solution further containing ouabain in the aforesaid HA medium, HA-O medium) and culturing.

As the partner cells, there can be used mouse derived X63, P3 U1, X63,653, SP2/0, etc. and human derived SKO-007, GM1500, etc.

(3) Detection of antibodies

With respect to the well in which clear growth of the hybridoma has thus been noted, antibodies showing reactivity with plural *Pseudomonas aeruginosa* of different serotypes are detected by the enzyme immunoassay in a manner similar to the EB virus transformation method described above.

(4) Cloning

As stated in the EB virus transformation method described above, cloning is repeated to obtain a single cell line.

(5) Culture of established cell

In a manner similar to the EB virus transformation method described above, the single cell line can be cultured in a suitable culture solution.

(6) Purification of antibodies

In a manner similar to the EB virus transformation method described above, the human monoclonal antibodies of the present invention can be purified from the culture solution.

3. Production of human monoclonal antibody preparations

The human monoclonal antibodies capable of plurally reacting with O-antigens of *Pseudomonas aeruginosa* can be used as liquid preparations or lyophilized preparations singly or as admixture with conventionally used additives or excipients. Upon actual use in prophylaxis and therapy of *Pseudomonas aeruginosa* infectious diseases, the human monoclonal antibodies of the present invention can be used singly or as a mixture of two or more monoclonal antibodies; alternatively, the human monoclonal antibodies may also be used as admixture with other human monoclonal antibodies against *Pseudomonas aeruginosa* and/or human globulin preparations. Particularly in the case of producing mixed preparations, the use of the present antibodies results in broadening a protection spectrum of the antibodies and therefore, the number of kinds of human monoclonal antibodies to be mixed can be reduced.

Dose and route for injection of the human monoclonal antibodies according to the present invention can be appropriately chosen but it is preferred that the dose be 0.01 to 10 mg/kg body weight and the route for injection can be intradermal, subcutaneous, intramuscular, intravenous, etc.

4. Examples

The present invention will be described in more detail with reference to the examples below.

EXAMPLE 1

Production of Human Monoclonal Antibodies by ES Virus Transformation Technique (1)

(1) Preparation of antigen

Following the serological classification of the Serotyping Committee for the Japan *Pseudomonas aeruginosa* Society (group A to group M), bacterial cells and LPSs used for antibody assay were prepared from strains shown in Table 1 below.

TABLE 1

| Serological Classification of the Serotyping Committee for the Japan *Pseudomonas aeruginosa* Society | Strain* | |
|---|---|---|
| A | *Pseudomonas aeruginosa* | IID 1001(ATCC 27577) |
| B | | IID 1002(ATTC 27578), IID 1007(ATCC 27583) IID 1013(ATCC 27589), IID 5004 |
| C | | IID 1003(ATCC 27579) |
| D | | IID 1004(ATCC 27580) |
| E | | IID 1005(ATCC 27581), PA103 |
| F | | IID 1006(ATCC 27582), F7 |
| G | | IID 1008(ATCC 27584), P28 |
| H | | IID 1009(ATCC 27585) |
| I | | IID 1010(ATCC 27586) |
| J | | IID 1011(ATCC 27587) |
| K | | IID 1012(ATCC 27588) |
| L | | IID 1014(ATCC 27590) |
| M | | IID 5018 |

*Among strains of *Pseudomonas aeruginosa* of group A to group M exemplified in Table 1, ATCC strains within parenthesis and IID strains have been stored in American Type Culture Collection and University of Tokyo, Institute of Medical Science, respectively and are freely assigned to a third person.

Each *Pseudomonas aeruginosa* strain was cultured in nutrient agar (Nissui Pharmaceutical Co., Ltd.) at 37° C. overnight. Proliferated colonies were collected and suspended in physiological salt solution to prepare a cell suspension. 0.5 ml of the cell suspension was inoculated in Sakaguti flask charged with 150 ml of Homma et al's synthetic medium [Tanamoto et al., J. Biochem., 83, 711–718 (1978)] per flask followed by shaking culture at 37° C. for 16 hours. After incubation, formalin was added to the flask in a final concentration of 0.3% and the system was allowed to stand at room temperature for an hour. Lastly, the cells were collected by centrifugation (12,000×g, 30 minutes). After washing with physiological salt solution and then distilled water in sequence, the cells were lyophilized to give formalinized dry cells. Each serotype *Pseudomonas aeruginosa* LPS was obtained using 20 g of formalinized wet cells prior to lyophilization as starting materials and purified by the hot phenol extraction method [book entitled "Meneki Jikken Sosaho" (Method for Immunological Experiments), page 2037, edited by Japanese society of Immunology (1978)]. Yields (dry weight) of LPSs from formalinized cells of the respective serotype *Pseudomonas aeruginosa* were 25 to 75 mg.

(2) Preparation of EB viral solution

B95-8 cells producing and releasing EB virus were suspended in RPMI 1640 medium containing 20% FCS (hereafter sometimes referred to as culture solution) in a density of $3 \times 10^5$/ml followed by static culture at 37° C. in the presence of 5% carbon dioxide. The culture supernatant on the 7th day close to the stationary phase was collected by centrifugation (800×g, 10 minutes). After filtering through membrane filter (Millipore) having a pore size of 0.45 microns, the filtrate was used as EB viral solution for transformation experiment.

(3) Preparation of human antibody producing cells (lymphocytes)

An equal amount of RPMI 1640 medium was added to 50 ml of heparinized peripheral blood collected from healthy donor to dilute to 2-fold. Then, the dilution was laid on a Ficoll-Paque (Pharmacia) of a half amount of the dilution so as not to disturb the interface followed by centrifugation (400×g, 30 minutes) at room temperature. After the centrifugation, the interface phase was taken out using a pasteur pipette and an equal amount of 20% FCS-containing RPMI 1640 medium was added thereto. The mixture was centrifuged (250×g, 10 minutes) at room temperature. The precipitated cells were suspended in 20% FCS-containing RPMI 1640 medium. Centrifugal operation was further repeated once to obtain pellet (cell count $5 \times 10^7$) of human antibody producing cells (lymphocytes).

(4) Transformation with EB virus

To 5×10 of human antibody producing cells was added 50 ml of the viral solution prepared in (2) followed by incubation at 37° C. for an hour. After incubation, the cells were collected by centrifugation (250×g, 10 minutes). The cells were dispersed in 20% FCS-containing RPMI 1640 medium. After adjusting the density to $5 \times 10^5$/ml, 0.1 ml each of the suspension was added to a 96 well flat bottom culture plate followed by static culture at 37° C. in the presence of 5% carbon dioxide. Four days after, 0.1 ml of 20% FCS-containing RPMI 1640 medium was added to the culture and thereafter, a half of the culture solution was replaced with a fresh culture solution every 4 or 5 days. By the antibody detection method shown in (5), cells of a well in which the reactivity with *Pseudomonas aeruginosa* was noted were cultured in a 24 well culture plate on an enlarged scale.

(5) Detection of antibodies

With respect to the well in which cell growth was noted, the presence or absence of human monoclonal antibodies to *Pseudomonas aeruginosa* in the culture supernatant was determined by the DIBA method classified into the enzyme-linked immunosorbent assay. In the case of the culture supernatant in the 96 well flat bottom culture plate, 0.1 ml of the culture supernatant in each well was reacted with grid-printed nitrocellulose membrane filter (3.1 mm square) having fixed a mixture of 0.4 μg/dot each of formalinized dry cells from *Pseudomonas aeruginosa* of 13 serotypes in a 96 well U-shaped bottom multiplate. In the case of the culture supernatant in the 24 well culture plate, 0.2 ml of the culture supernatant in each well was reacted in a 48 well culture plate with grid-printed nitrocellulose membrane filters (6.2 mm×9.3 mm square) having fixed formalinized dry cells from *Pseudomonas aeruginosa* of 6 kinds of group A to group F and 7 kinds of group G to group M on different places. After reacting at room temperature for 2 hours and then reacting with peroxidase-conjugated rabbit anti-human immunoglobulin (DAKO) for 2 hours, color was formed using 4-chloro-1-naphthol as a substrate. Antibody production was judged to be positive with those in which color formation was noted on the antigen-fixed nitrocellulose membrane filter by observation with the naked eye.

(6) Cloning

The cells of a well in which the reactivity with plural *Pseudomonas aeruginosa* of different serotypes was noted by the antibody detection method were transferred to a 6 cm dish. The cells proliferated on the 6 cm dish were cloned by the soft agar method. Firstly, after accurately counting the cells with a hemacytometer, the cells were made a cell suspension in a density of $1 \times 10^6$/ml and 0.1 ml of the cell suspension was added to 30 ml of a culture solution containing 0.3% agarose (SeaPlaque agarose, FMC) followed by mixing them. Next, 3 ml of the culture solution containing the cells and 0.3% agarose was separately charged in a 6 cm dish, which had been solidified by previously separately charging 4 ml of the culture solution containing 0.5% agarose, to solidify (10 dishes per each well). The 6 cm dish in which the cells had been separately charged was subjected to static culture at 37° C. in the presence of 5% carbon dioxide. Three to five weeks after, the cells grew in soft agar and colonies were recognized with the naked eye; at this stage, each colony was transferred with a pasteur pipette to and cultured in each well of a 96 well flat bottom culture plate in which 0.1 ml/well of the culture solution had been separately charged. Two days after, 0.1 ml of the culture solution was added and further 2 days after, the presence or absence of human monoclonal antibodies to *Pseudomonas aeruginosa* in the culture supernatant was determined by the DIBA method, with respect to the well in which cell growth was noted. Cells in a well in which antibody production was judged to be positive were cultured in a 24 well culture plate on an enlarged scale. Three days after, the presence or absence of human monoclonal antibodies to *Pseudomonas aeruginosa* in the culture supernatant was determined by the DIBA method, with respect to the wells in 24 well culture plate. Operations similar to above were again repeated as described above, with cells in a well which was judged to produce an antibody capable of reacting with *Pseudomonas aeruginosa* of a plurality of serotypes, to effect cloning. Thus, EB virus transformed cell line MP 5035 capable of producing human monoclonal antibody HPs1 (IgM) having cross reactivity with group I and group D of serotype in the serological classification of the Serotyping Committee for the Japan *Pseudomonas aeruginosa* Society, and EB virus transformed cell line MP 5038 capable of producing human monoclonal antibody HPs2 (IgM) having cross reactivity with group E and group F of serotype in the serological classification of the Serotyping Committee for the Japan *Pseudomonas aeruginosa* Society, were obtained. MP 5035 and MP 5038 have been deposited in the Fermentation Research Institute of the Agency of Industrial Science and Technology of Japan under FERM BP-1598 and FERM BP-1596.

(7) Culture of cell line and purification of antibodies

Two EB virus transformed cell lines capable of producing human monoclonal antibodies HPs1 and HPs2 respectively were cultured in RITC 55-9 medium [Exp. Cell Res., 138,127–134 (1982)] containing 0.5% bovine serum albumin (hereafter merely referred to as BSA) using a flask (bottom area of 175 cm$^2$). The culture was centrifuged (400×g, 30 minutes) to give the supernatant and, the antibodies were purified by the 50% ammonium sulfate precipitation method and the fractionation method using Sephacryl S-300 (Pharmacia) column. From 250 ml of the culture solution obtained by culturing the EB virus transformed cell line capable of producing HPs1, 2.5 mg of IgM fraction was obtained and 76 mg of IgM fraction was obtained from 2 liters of the culture solution obtained by culturing the EB virus transformed cell line capable of producing HPs2.

EXAMPLE 2

Production of Human Monoclonal Antibodies by EB Virus Transformation Technique (2)

Transformation with EB virus was carried out in a manner similar to Example 1 except for using peripheral blood collected from patients with *Pseudomonas aeruginosa* infectious disease. Pellet (cell count; 1.4×10$^7$) of human antibody producing cells were obtained from 25 ml of heparinized peripheral blood. Soft agar cloning was conducted twice to give EB virus transformed cell line MP 4091 capable of producing human monoclonal antibody HPs4 (IgM) having cross reactivity with group A and group L of serotype in the serological classification of the Serotyping Committee for the Japan *Pseudomonas aeruginosa* Society, and EB virus transformed cell line MP 5050 capable of producing human monoclonal antibody HPs5 (IgM) having cross reactivity with group G and group H of serotype in the serological classification of the Serotyping Committee for the Japan *Pseudomonas aeruginosa* Society. MP 5050 has been deposited in the Fermentation Research Institute of the Agency of Industrial Science and Technology of Japan under FERM BP-1600. The cells were cultured in a manner similar to Example 1 (7). From 250 ml of the culture solution obtained by culturing the EB virus transformed cell line MP 4091 capable of producing HPs4, 2.5 mg of IgM fraction was obtained. From 450 ml of the culture solution obtained by culturing the EB virus transformed cell line MP 5050 capable of producing HPs5, 8.6 mg of IgM fraction was obtained.

EXAMPLE 3

Production of Human Monoclonal Antibody by ES Virus Transformation Technique (3)

Transformation with EB virus was carried out in a manner similar to Example 1 except for using peripheral blood collected from another healthy donor. Pellet (cell count; 2.8×10$^7$) of human antibody producing cells were obtained from 25 ml of heparinized peripheral blood. Soft agar cloning was conducted twice to give EB virus transformed cell line MP 5046 capable of producing human monoclonal antibody HPs7 (IgM) having cross reactivity with group A and group F of serotype in the serological classification of the Serotyping Committee for the Japan *Pseudomonas aeruginosa* Society. MP 5046 has been deposited in the Fermentation Research Institute of the Agency of Industrial Science and Technology of Japan under FERM BP-1599. The cells were cultured in a manner similar to Example 1 (7). From 300 ml of the culture solution obtained by culturing the EB virus transformed cell line MP 5046 capable of producing HPs7, 4.1 mg of IgM fraction was obtained.

EXAMPLE 4

Production of Human Monoclonal Antibody by Hybridoma Technique (1)

(1) Preparation of human antibody producing cells (B cells)

Pellet (cell count; 4.6×10$^7$) of human antibody producing cells were obtained from 50 ml of heparinized peripheral blood collected from healthy donor, in a manner similar to Example 1 (3). To the pellet was added 46 ml of the vital solution prepared in Example 1 (2) followed by incubation at 37° C. for an hour. After incubation, a culture solution was added to the cells collected by centrifugation (250×g, 10 minutes) to suspend the cells in a density of 1×10$^5$/ml. The suspension was separately charged in two flasks (bottom area of 175 cm$^2$) followed by static culture at 37° C. in the presence of 5% carbon dioxide. Five days after 50 ml each of the culture solution was added and further 5 days after, the cells were collected by centrifugation.

(2) Cell fusion

EB virus transformed cells and mouse myeloma cell line NS-1 were washed with RPMI 1640 medium, respectively. In a plastic-made centrifugal tube of a 50 ml volume 1.3×10$^8$ of EB virus transformed cells and 1.3×10$^8$ of mouse myeloma cells were mixed with each other. The mixed cells were centrifuged (175×g, 10 minutes). The supernatant was discarded and the cells were loosened by gentle vibration. To the centrifugal tube containing the cells, 0.5 ml of RPMI 1640 medium supplemented with 50% polyethylene glycol (M.W. 1500, Wako Junyaku) and 10% dimethylsulfoxide was gently added. While slowly rotating the centrifugal tube, the cells were fused. Two minutes after, 10 ml of RPMI 1640 medium was added thereto. After gently agitating, centrifugation (175×g, 10 minutes) was performed. After the centrifugation, the supernatant was discarded and RPMI 1640 medium containing 2×10$^{-4}$M hypoxanthine, 0.176 µg/ml of aminoputerine, 13 µg/ml of thymidine, 5 µM ouabain and 20% FCS (hereafter merely referred to as HAT-O culture solution) was added to make a cell suspension in a density of 1×10$^6$/ml. 0.1 ml each per well of the suspension was charged in a 96 well flat bottom culture plate followed by static culture at 37° C. in the presence of 5% carbon dioxide. Four days after 0.1 ml of the HAT-O culture solution was added and thereafter, a half of the culture solution was replenished with a fresh HAT-O culture solution every 4 to 5 days.

(3) Detection of antibody

With respect to the well in which cell growth was noted, the presence or absence of human monoclonal antibody to *Pseudomonas aeruginosa* in the culture supernatant was determined by the DIBA method in a manner similar to Example 1 (5). The culture supernatant, 0.1 ml, in a 96 well flat bottom culture plate was diluted with RPMI 1640 medium to 2-fold and reacted in a 48 well culture plate with two grid-printed nitrocellulose membrane filters (6.2 mm×9.3 mm square) having fixed formalinized dry cells from *Pseudomonas aeruginosa* of 6 kinds of group A to group F and 7 kinds of group G to group M on different places.

(4) Cloning

3 % Glycogen (Tokyo Kasei Kogyo)-containing phosphate buffered saline (hereafter simply referred to as PBS) was previously injected intraperitoneally to mice (Balb/c) and peritoneal exudate cells were collected 4 days after to make a cell suspension in a density of 1×10$^5$/ml and a 96 well flat bottom culture plate separately charged with 0.1 ml each/well of the cell suspension was prepared. Next, cells in wells in which reactivity with *Pseudomonas aeruginosa* of a plurality of serotypes was noted by the antibody detection method were collected, respectively. The cells were accurately counted using a hemacytometer and dispersed in HAT-O culture solution to make cell suspensions of 20/ml and 200/ml. After the supernatant of each well in the 96 well flat bottom culture plate separately charged with the mouse peritoneal exudate cells described above was removed, 0.1 ml each was added followed by static culture at 37° C. in the presence of 5% carbon dioxide. Four days after 0.1 ml of the HAT-O culture solution was added and thereafter, a half of the culture solution was replenished with a fresh HAT-O culture solution every 4 to 5 days. With respect to wells in which cell growth was noted 7 to 14 days after, the presence or absence of human monoclonal antibody to *Pseudomonas aeruginosa* in the culture supernatant was determined by the DIBA method. Cells in a well which was judged to produce an antibody capable of reacting with *Pseudomonas aeruginosa* of a plurality of serotypes were again repeatedly subjected to operations similar to above thereby to achieve cloning. Thus, hybridoma cell line MP 4092 capable of producing human monoclonal antibody HPs6 (IgG) cross reactive with each of group E and group F in the serological classification of the Serotyping Committee for the Japan *Pseudomonas aeruginosa* Society, was obtained.

(5) Culture of cell line and purification of antibody

The hybridoma cells thoroughly grown in a 96 well flat bottom culture plate were cultured on a gradually enlarged scale, and in the stirring system of 1 liter, culture was performed using 500 ml of 20% FCS-containing RPMI 1640 medium. The culture was centrifuged (400×g, 30 minutes) to give the supernatant and, the antibody was purified by the 50% ammonium sulfate precipitation method and the fractionation method using Protein A-Sepharose 4B (Pharmacia) column to give 5 mg of IgG.

EXAMPLE 5

Production of Human Monoclonal Antibody by Hybridoma Technique (2)

(1) Preparation of 2-aminoethyl isothiouronium hydrobromide (hereafter simply referred to as AET)-treated sheep red blood cells In a plastic-made centrifugal tube of a 50 ml volume was taken 5 ml of a suspension of sheep red blood cells (Nihon Biotest Laboratory, hereafter simply reffered to as SRBC) and, 20 ml of gelatin veronal buffer (hereafter simply referred to as GVB) was added to the suspension. After thoroughly agitating, the mixture was centrifuged (1,600×g, 10 minutes). The supernatant was discarded by suction and precipitated SRBC was suspended in 20 ml of GVB. Centrifugal operation was repeated further 3 times. To about 1 ml of SRBC pellet obtained was added 4 ml of 0.143M AET aqueous solution to suspend the pellets. While agitating sometimes, the suspension was reacted at 37° C. for 15 minutes. Immediately after completion of the reaction, 20 ml of ice-cooled GVB was added to the reaction mixture. After thorough agitation, centrifugation was carried out (1,600×g, 10 minutes). The supernatant was discarded by suction and the precipitates were suspended in 20 ml of GVB. Centrifugal operation was repeated further twice. The AET-treated SRBC was suspended in GVB in a density of $2×10^8$/ml and stored under ice cooling until it was provided for use.

(2) Preparation of human antibody producing cells (B cells)

On an equal amount of mono-poly resolving medium (Flow) was laid 25 ml of heparinized peripheral blood collected from healty donor having a high titer to *Pseudomonas aeruginosa* who was in hospital by car accident and passed for about 3 months after cure of wound so as not to disturb the interface followed by centrifugation (350×g, 30 minutes) at room temperature. After the centrifugation, liquid containing cells at the interface was taken out using a pasteur pipette and an equal amount of 20% FCS-containing RPMI 1640 medium was added thereto. The mixture was centrifuged (350×g, 10 minutes) at room temperature. The precipitated cells were again suspended in 20% FCS-containing RPMI 1640 medium. Centrifugal operation was further repeated once to obtain pellet (cell count $5×10^7$) of human lymphocyte fraction.

Next, the obtained human lymphocyte fraction was suspended in 4 ml of 20% FCS-containing RPMI 1640 medium to make a suspension in a density of $5×10^6$/ml. In 8 plastic-made centrifugal tubes of a 50 ml each volume was separately charged 0.5 ml each of the suspension and, 1 ml each of the AET-treated SRBC suspension prepared in (1) was added to each centrifugal tube. After thoroughly agitating, the mixture was centrifuged (20×g, 2 minutes). After the centrifugation, the system was settled at 4° C. for 2 hours to perform rosette formation. After completion of the reaction, 1.5 ml of 20% FCS-containing RPMI 1640 medium was added and the pellet was gently destroyed using a pasteur pipette. The cell suspensions which formed rosette were collected and laid on 20 ml of mono-poly resolving medium charged in a plastic-made centrifugal tube of a 50 ml volume so as not to disturb the interface followed by centrifugation (350×g, 30 minutes). After the centrifugation, liquid containing cells at the interface was taken out using a pasteur pipette and an equal amount of 20% FCS-containing RPMI 1640 medium was added thereto. The mixture was centrifuged (250×g, 10 minutes) at room temperature. The precipitated cells were again suspended in 20% FCS-containing RPMI 1640 medium. Centrifugal operation was repeated further twice to obtain pellet (cell count $1.0×10^7$) of human antibody producing cells (B cells).

The pellet of human antibody producing cells (B cells) was suspended in 20 ml of 20% FCS-containing RPMI 1640 medium. The suspension was adjusted to a density of $5×10^5$/ml. Pokeweed mitogen (PWM) (Gibco) of a 1/200 volume was added to the suspension. The mixture was charged in a flask (bottom area of 75 cm$^2$) followed by static culture at 37° C. for 6 days in the presence of 5% carbon dioxide.

(3) Cell fusion

PBS containing 2.5% glycogen was previously injected intraperitoneally to mice (Balb/c) in 0.5 ml/mouse and peritoneal exudate cells were collected 4 days after. The cells were suspended in 20% FCS-containing RPMI 1640 medium, together with mouse spleen cells separately prepared to make cell suspensions in densities of $5×10^5$/ml and $1×10^6$/ml, respectively. A 96 well flat bottom culture plate (hereafter simply referred to as feeder plate) separately charged with 0.1 ml each/well of each cell suspension was prepared.

PWM-treated human antibody producing cells (B cells) and human lymphoblast like cells MHP-315 were washed with RPMI 1640 medium, respectively. In a plastic-made centrifugal tube of a 50 ml volume $5×10^7$ of human antibody producing cells (B cells) and the same count of human lymphoblast like cells were mixed with each other. The mixed cells were centrifuged (175×g, 10 minutes). The supernatant was discarded and the cells were suspended in FCS free RPMI 1640 medium. Centrifugal operation was repeated further twice. After the centrifugation, the supernatant was removed using a pasteur pipette as much as possible to make cell pellet. Gentle vibration was given to the pellet to loosen the cells a little. Then 0.3 ml of a fusing reagent (PBS containing 50% polyethylene glycol 4000 and 10% dimethylsulfoxide) was added thereto. The centrifugal tube was slowly rotated for 90 seconds. Ninety seconds after, 20 ml of 20% FCS-containing RPMI 1640 medium was gradually added thereto. Further 2 minutes after, 20 ml of the same medium was added to gently disperse the cells. The cells after cell fusion was pelletized by centrifugation (175×g, 10 minutes). The pellet was dispersed in 20% FCS-containing RPMI 1640 medium to adjust a density of $1\times10^6$/ml. After the supernatant in each well of the feeder plate was removed, 0.1 ml each/well of the cell dispersion was added followed by static culture at 37° C. in the presence of 5% carbon dioxide.

Twenty four hours after, 0.1 ml each/well of 20% FCS-containing RPMI 1640 medium containing $4\times10^{-4}$M hypoxanthine, 2 µg/ml of azaserine and 10 µM ouabain was added to the culture. Thereafter, a half of the culture solution was replenished with 20% FCS-containing RPMI 1640 medium containing $2\times10^{-4}$M hypoxanthine, 1 µg/ml of azaserine and 5 µM ouabain (hereafter simply referred to as HA-O culture solution) every 3 to 4 days.

(4) Detection of antibody

With respect to the well in which cell growth was noted about 4 to 5 weeks after, the presence or absence of human monoclonal antibody to *Pseudomonas aeruginosa* in the culture supernatant was determined by the DIBA method in a manner similar to Example 1 (5).

(5) Cloning

Cells in wells in which reactivity with *Pseudomonas aeruginosa* of a plurality of serotypes was noted by the antibody detection method were collected, respectively. The cells were accurately counted using a hemacytometer and dispersed in HA-O culture solution to make cell suspensions of 20/ml and 200/ml. After the supernatant of each well in the feeder plate described above was removed, 0.1 ml each was added followed by static culture at 37° C. in the presence of 5% carbon dioxide. Four days after 0.1 ml of the HA-O culture solution was added and thereafter, a half of the culture solution was replenished with a fresh HA-O culture solution every 3 to 4 days. With respect to the well in which cell growth was noted about 2 to 4 weeks after, the presence or absence of human monoclonal antibody to *Pseudomonas aeruginosa* in the culture supernatant was determined by the DIBA method. Cells which were judged to produce an antibody reactive with *Pseudomonas aeruginosa* of a plurality of serotypes were again subjected to operations similar to above thereby to achieve cloning. Thus, hybridoma cell line MP 4095 capable of producing human monoclonal antibody HPs8 (IgM) cross reactive with each of group E and group F in the serological classification of the Serotyping Committee for the Japan *Pseudomonas aeruginosa* Society, was obtained. MP 4095 has been deposited in the Fermentation Research Institute of the Agency of Industrial Science and Technology of Japan under FERM P-9750.

(6) Culture of cell line and purification of antibody

The hybridoma cell line MP 4095 thoroughly grown in a 96 well flat bottom culture plate was cultured on a gradually enlarged scale, and was cultured on 4 flasks (bottom area of 175 cm²) using 200 ml of NYSF 404 serum free medium [Yabe, Tissue Culture, 11, 458 (1985)]. The culture was centrifuged (400×g, 30 minutes) to give 190 ml of the supernatant. The supernatant was filtered through membrane filter having a pore size of 0.22 microns. The filtrate was adsorbed to Mono Q column (Pharmacia) at a flow rate of 2 ml/min, which column had been previously equilibrated with 0.025M phosphate buffer (pH 6.8). After adsorption, the column was washed with a mixture of the same amounts of said buffer and 0.3M phosphate buffer (pH 6.5). After washing, IgM fraction was eluted with 0.3M phosphate buffer (pH 6.5). From 190 ml of the culture supernatant, 1 mg of IgM antibody was obtained.

EXAMPLE 6

Production of Human Monoclonal Antibody by Hybridoma Technique (3)

(1) Preparation of human antibody producing cells

As human antibody producing cells, EB virus transformed cell line MP 5035 capable of producing human monoclonal antibody HPs1 (IgM) obtained in Example 1 and having cross reactivity with group I and group D in the serological classification of the Serotyping Committee for the Japan *Pseudomonas aeruginosa* Society was used. MP 5035 was cultured in a flask (bottom area of 175 cm²) using 20% FCS-containing RPMI 1640 medium. Cells in the logarithmic phase were collected by centrifugation and provided to produce hybridoma.

(2) Cell fusion

The transformed cell line MP 5035 and human lymphoblast like cell line MHP-315 were washed with FCS free RPMI 1640 medium, respectively. In a plastic-made centrifugal tube of a 50 ml volume $1.3\times10^8$ of the transformed cells and the same count of human lymphoblast like cells were mixed with each other. The mixed cells were centrifuged (175×g, 10 minutes). The supernatant was discarded and the precipitated cells were suspended in FCS free RPMI 1640 medium. Centrifugal operation was repeated further twice. After the centrifugation, the supernatant was removed using a pasteur pipette as much as possible to make cell pellet. Gentle vibration was given to the pellet to loosen the cells a little. Then 0.3 ml of a fusing reagent (PBS containing 50% polyethylene glycol 4000 and 10% dimethylsulfoxide) was added thereto. The centrifugal tube was slowly rotated for 90 seconds at room temperature. Ninety seconds after, 20 ml of 20% FCS-containing RPMI 1640 medium was was gradually added thereto. Further 2 minutes after, 20 ml of the same medium was added to gently disperse the cells. The cells after cell fusion was pelletized by centrifugation (175× g, 10 minutes). The pellet was dispersed in 20% FCS-containing RPMI 1640 medium to adjust a density of $1\times10^6$/ml. After the supernatant in each well of the feeder plate was removed, 0.1 ml each/well of the cell dispersion was added followed by static culture at 37° C. in the presence of 5% carbon dioxide.

Twenty four hours after, 0.1 ml each/well of 20% FCS-containing RPMI 1640 medium containing $4\times10^{-4}$M hypoxanthine, 2 µg/ml of azaserine and 10 µM ouabain was added to the culture. Thereafter, a half of the culture solution was replenished with 20% FCS-containing RPMI 1640 medium containing $2\times10^{-4}$M hypoxanthine, 1 µg/ml of azaserine and 5 µM ouabain (HA-O culture solution) every 3 to 4 days.

(3) Detection of antibody

With respect to the well in which cell growth was noted about 4 to 5 weeks after, the presence or absence of human monoclonal antibody to *Pseudomonas aeruginosa* in the culture supernatant was determined by the DIBA method in a manner similar to Example 1 (5).

(4) Cloning

Cells in wells in which the presence of an antibody having reactivity with *Pseudomonas aeruginosa* of serotypes of group D and group I was noted by the antibody detection method were collected, respectively. The cells were accurately counted using a hemacytometer and dispersed in HA-O culture solution to make cell suspensions of 20/ml and 200/ml. After the supernatant of each well in the feeder plate (each one plate) was removed, 0.1 ml each was inoculated per each well followed by static culture at 37° C. in the presence of 5% carbon dioxide. Four days after 0.1 ml of the HA-O culture solution was added and thereafter, a half of the culture solution was replenished with a fresh HA-O culture solution every 3 to 4 days. With respect to the well in which cell growth was noted about 2 to 4 weeks after, the presence or absence of human monoclonal antibody to *Pseudomonas aeruginosa* in the culture supernatant was determined by the DIBA method. Cells which were judged to produce an antibody reactive with *Pseudomonas aeruginosa* of serotypes of group D and group I were again subjected to operations similar to above thereby to achieve cloning. Thus, hybridoma cell line MP 5082 capable of producing human monoclonal antibody HPs9 (IgM) cross reactive with each of group D and group I in the serological classification of the Serotyping Committee for the Japan *Pseudomonas aeruginosa* Society, was obtained with twice cloning. The cells thoroughly grown in a 96 well flat bottom culture plate were cultured on a gradually enlarged scale. MP 5082 has been depodited in the Fermentation Research Institute of the Agency of Industrial Science and Technology of Japan under FERN P-9745.

(5) Culture of cell line and purification of antibody

The hybridoma cell line MP 5082 was dispersed in 200 ml of NYSF 404 serum free medium in a cell density of $3 \times 10^5$/ml. The suspension was separately charged in 4 flasks (bottom area of 175 cm$^2$) followed by static culture at 37° C. in the presence of 5% carbon dioxide. On the fourth day after onset of the culture, the culture solution was centrifuged (400×g, 20 minutes) to give 190 ml of the supernatant. From the culture supernatant, the antibody was purified by Mono Q column in a manner similar to Example 5 (6). From 190 ml of the culture supernatant, 1.7 mg of IgM antibody was obtained.

EXAMPLE 7

Production of Human Monoclonal Antibody by Hybridoma Technique (4)

Cell fusion was performed between human antibody producing cells and human derived lymphoblast like cell line MHP-315 in a manner similar to Example 6, except for using, as human antibody producing cells, EB virus transformed cell line MP 5038 established in Example 1, capable of producing human monoclonal antibody HPs2 (IgM) and having cross reactivity with group E and group F in the serological classification of the Serotyping Committee for the Japan *Pseudomonas aeruginosa* Society. Firstly, MP 5038 was cultured in a flask (bottom area of 175 cm$^2$) using 20% FCS-containing RPMI 1640 medium. Cells in the logarithmic phase were collected by centrifugation and provided to produce hybridoma. Cell fusion was performed between 1.0×108 of the EB virus transformed cells and the same count of human lymphoblast like cells followed by cloning in a manner similar to Example 6. Thus, there was obtained hybridoma cell line MP 5064 capable of producing human monoclonal antibody HPs10 (IgM) cross reactive with each of group E and group F in the serological classification of the Serotyping Committee for the Japan *Pseudomonas aeruginosa* Society. MP 5064 has been deposited in the Fermentation Research Institute of the Agency of Industrial Science and Technology of Japan under FERM P-9751. The hybridoma cell line MP 5064 was dispersed in 350 ml of NYSF 404 serum free medium in $3 \times 10^5$/ml. The suspension was separately charged in 7 flasks (bottom area of 175 cm$^2$) followed by static culture at 37° C. in the presence of 5% carbon dioxide. On the fourth day after onset of the culture, the culture solution was centrifuged (400×g, 20 minutes) to give 330 ml of the supernatant. From the culture supernatant, the antibody was purified by Mono Q column in a manner similar to Example 5 (6). From 300 ml of the culture supernatant, 7.7 mg of IgM was obtained.

EXAMPLE 8

Production of Human Monoclonal Antibody by Hybridoma Technique (5)

Cell fusion was performed between human antibody producing cells and human derived lymphoblast like cell line MHP-315 in a manner similar to Example 6, except for using, as human antibody producing cells, EB virus transformed cell line MP 5050 established in Example 2, capable of producing human monoclonal antibody HPs5 (IgM) and having cross reactivity with group G and group H in the serological classification of the Serotyping Committee for the Japan *Pseudomonas aeruginosa* Society. Firstly, MP 5050 was cultured in a flask (bottom area of 175 cm$^2$) using 20% FCS-containing RPMI 1640 medium. Cells in the logarithmic phase were collected by centrifugation and provided to produce hybridoma. Cell fusion was performed between 1.3×10 of the EB virus transformed cells and the same count of human lymphoblast like cells followed by a manner similar to Example 6. Thus, there was obtained hybridoma cell line MP 5104 capable of producing human monoclonal antibody HPs11 (IgM) cross reactive with each of group G and group H in the serological classification of the Serotyping Committee for the Japan *Pseudomonas aeruginosa* Society. MP 5104 has been deposited in the Fermentation Research Institute of the Agency of Industrial Science and Technology of Japan under FERM P-9753. The hybridoma cell line MP 5104 was dispersed in 500 ml of NYSF 404 serum free medium in $3 \times 10^5$/ml. The suspension was separately charged in 10 flasks (bottom area of 175 cm$^2$) followed by static culture at 37° C. in the presence of 5% carbon dioxide. On the fourth day after onset of the culture, the culture solution was centrifuged (400×g, 20 minutes) to give 470 ml of the supernatant- From the culture supernatant, the antibody was purified by Mono Q column in a manner similar to Example 5 (6). From 450 ml of the culture supernatant, 9.8 mg of IgM antibody was obtained.

EXAMPLE 9

Production of Human Monoclonal Antibody by Hybridoma Technique (6)

Cell fusion was performed between human antibody producing cells and human derived-lymphoblast like cell line MHP-315 in a manner similar to Example 6, except for using, as human antibody producing cells, EB virus transformed cell line MP 5046 established in Example 3, capable of producing human monoclonal antibody HPs7 (IgM) and having cross reactivity with group A and group F in the serological classification of the Serotyping Committee for the Japan *Pseudomonas aeruginosa* Society. Firstly, MP 5046 was cultured in a flask (bottom area of 175 cm²) using 20% FCS-containing RPMI 1640 medium. Cells in the logarithmic phase were collected by centrifugation and provided to produce hybridoma. Cell fusion was performed between $1.3 \times 10^8$ of the EB virus transformed cells and the same count of human lymphoblast like cells followed by a manner similar to Example 6. Thus, there was obtained hybridoma cell line MP 5075 capable of producing human monoclonal antibody HPs12 (IgM) cross reactive with each of group A and group F in the serological classification of the Serotyping Committee for the Japan *Pseudomonas aeruginosa* Society. MP 5075 has been deposited in the Fermentation Research Institute of the Agency of Industrial Science and Technology of Japan under FERM P-9752. The hybridoma cell line. MP 5075 was dispersed in 550 ml of NYSF 404 serum free medium in $3 \times 10^5$/ml. The suspension was separately charged in 11 flasks (bottom area of 175 cm²) followed by static culture at 37° C. in the presence of 5% carbon dioxide. On the fourth day after onset of the culture, the culture solution was centrifuged (400×g, 20 minutes) to give 530 ml of the supernatant. From the culture supernatant, the antibody was purified by Mono Q column in a manner similar to Example 5 (6). From 530 ml of the culture supernatant, 13.4 mg of IgM was obtained.

EXAMPLE 10

Reactivity of Human Monoclonal Antibodies with LPS, Ra and Lipid A

Reactivities of the human monoclonal antibodies obtained in Examples 1, 2, 3, 4, 5, 6, 7, 8 and 9 with LPS of each serotype of *Pseudomonas aeruginosa*, Ra strain derived LPS and lipid A having only a common structural region of LPS were examined by the DIBA method described in Example 1. As each serotype *Pseudomonas aeruginosa* LPS, one prepared in Example 1 was used. As Ra (*Salmonella minnesota* R60) strain derived LPS and lipid A, those commercially available (List Biological Laboratories Inc.) were used. The results are shown in Table 2. Each human monoclonal antibody did not react with Ra or lipid A which is a common structural region of LPS but specifically reacted with each serotype *Pseudomonas aeruginosa* LPS. Therefore, it was made clear that they were human monoclonal antibodies of recognizing O-specific polysaccharide chain of LPS.

EXAMPLE 11

Cross Reactivity of Human Monoclonal Antibodies with LPSs (1)

Cross reactivities of the human monoclonal antibodies HPs1 and HPs2 obtained in Example 1 with O-specific polysaccharide chain of *Pseudomonas aeruginosa*, namely, O-antigens were examined by the enzyme-linked immunosorbent assay (ELISA) using a plate coated with LPS. The *Pseudomonas aeruginosa* LPS prepared in Example 1 was dissolved in carbonate buffer (pH 9.6) to make a concentration of 2 µg/ml. In each well of a 96 well plate (Greiner) for ELISA, 50 µl of LPS solution was separately charged to the well, which was allowed to stand at 37° C. for 2 hours. After fixing, the solution was discarded and blocked with 2% BSA-containing carbonate buffer. Each antibody (25 ng/ml) solution dissolved in PBS containing 0.05% Tween 20 was mixed with an equal amount of a 2-fold serial dilution of each *Pseudomonas aeruginosa* LPS solution (50 µg/ml). The mixture was reacted at room temperature for 1 hour. Fifteen microliters of the reaction solution was separately charged in each well of the above LPS-fixed 96 well plate for ELISA and reacted at room temperature for 1.5 hours. After washing the well with 0.05% Tween 20-containing PBS, a reaction was carried out with 50 µl of peroxidase-conjugated rabit anti-human immunoglobulin (500-fold dilution) at room temperature for 1.5 hours. After washing with 0.05% Tween 20-containing PBS, a reaction was carried out with 50 µl of citrate buffer containing 10 mg/ml of 2,2'-azinobis(3-ethylbenzthiazoline sulfonic acid) (ABTS) and 0.003% of hydrogen peroxide at room temperature for 30 minutes. Absorbancy at a wavelength of 414 nm was measured and, an inhibitory rate to binding of each antibody to LPS fixed onto the plate by each *Pseudomonas aeruginosa* LPS was determined from the absorbancy.

As shown in FIG. 1, binding of HPs1 to the plate coated with LPS of group I *Pseudomonas aeruginosa* was inhibited by each of LPS of group I-and group D *Pseudomonas aeruginosa* but not inhibited by LPS of group A *Pseudomonas aeruginosa*. Thus, it was confirmed that HPs1 was a monoclonal antibody of recognizing two O-antigens of group I and group D in common. As shown in FIG. 2, binding of HPs2 to the plate coated with LPS of group F *Pseudomonas aeruginosa* was inhibited by each LFS of

TABLE 2

| Monoclonal Antibody | Reactivity of Antibodies to Each Serotype LPS | | | | | | | | | | | | | | |
|---|---|---|---|---|---|---|---|---|---|---|---|---|---|---|---|
| | [Serotype] | | | | | | | | | | | | | Lipid A | Ra |
| | A | B | C | D | E | F | G | H | I | J | K | L | M | | |
| HPs1 | − | − | − | + | − | − | − | − | + | − | − | − | − | − | − |
| HPs2 | − | − | − | − | + | + | − | − | − | − | − | − | − | − | − |
| HPs4 | + | − | − | − | − | − | − | − | − | − | − | + | − | − | − |
| HPs5 | − | − | − | − | − | − | + | + | − | − | − | − | − | − | − |
| HPs6 | − | − | − | − | + | + | − | − | − | − | − | − | − | − | − |
| HPs7 | + | − | − | − | − | + | − | − | − | − | − | − | − | − | − |
| HPs8 | − | − | − | − | + | + | − | − | − | − | − | − | − | − | − |
| HPs9 | − | − | − | + | − | − | − | − | + | − | − | − | − | − | − |
| HPs10 | − | − | − | − | + | + | − | − | − | − | − | − | − | − | − |
| HPs11 | − | − | − | − | − | − | + | + | − | − | − | − | − | − | − |
| HPs12 | + | − | − | − | − | + | − | − | − | − | − | − | − | − | − | group E and group F *Pseudomonas aeruginosa* but not inhibited by LPS of group D *Pseudomonas aeruginosa*. Thus, it was confirmed that HPs2 was a monoclonal antibody of recognizing two O-antigens of group E and group F in common.

EXAMPLE 12

Cross Reactivity of Human Monoclonal Antibodies with LPSs (2)

Figure 4:
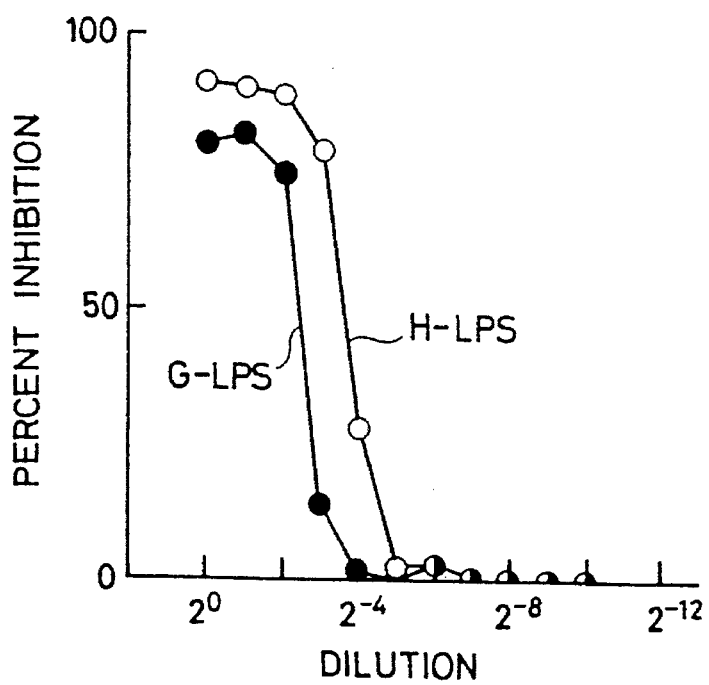
Figure 5:
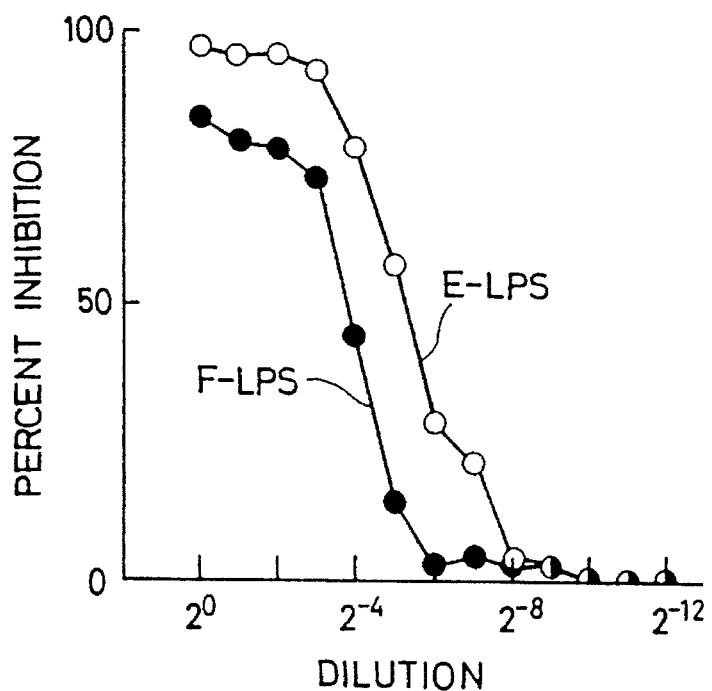
Figure 6:
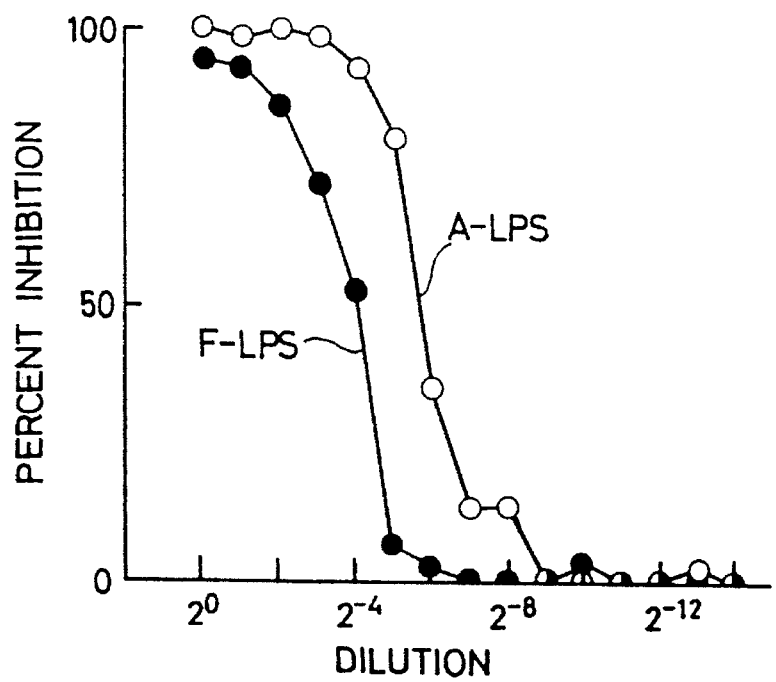
Figure 7:
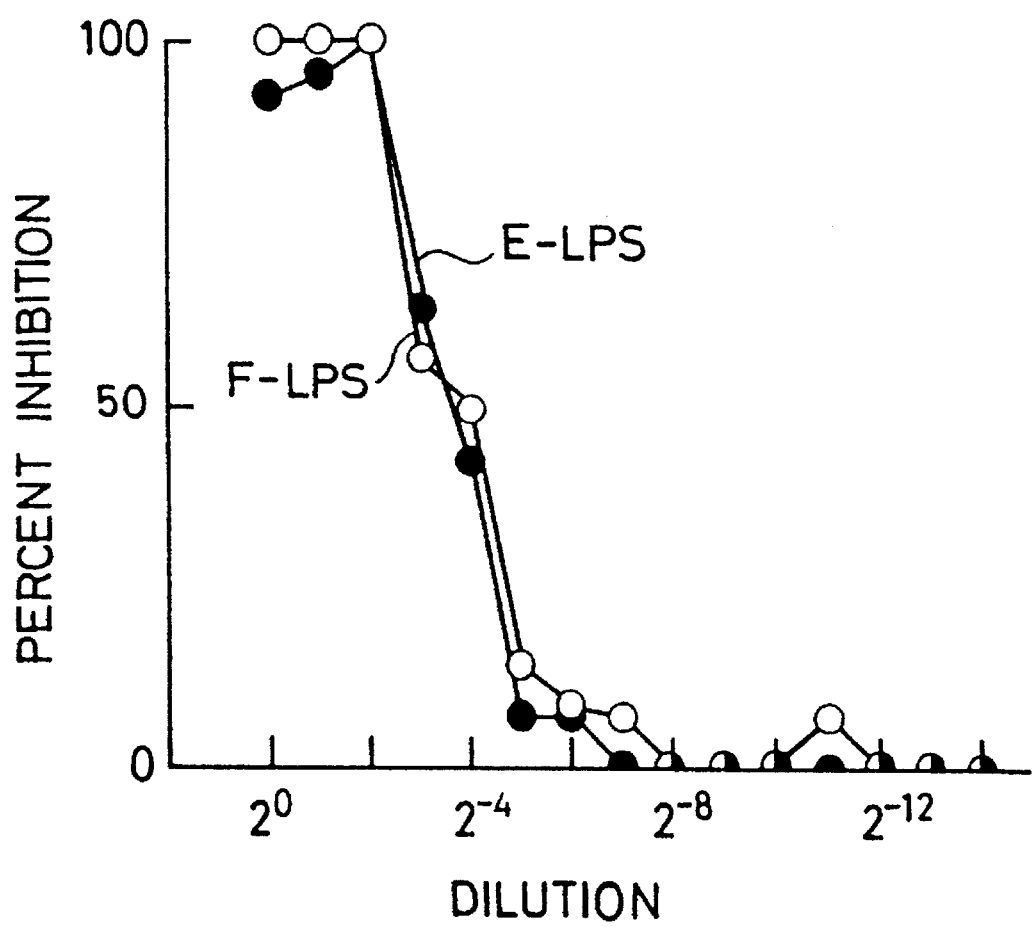

Cross reactivities of the human monoclonal antibodies HPs4, HPs5, HPs6, HPs7 and HPs8 obtained in Examples 2, 3, 4 and 5 with O-antigens of *Pseudomonas aeruginosa* were examined by ELISA using a plate coated with LPS in a manner similar to Example 11. As shown in FIG. 3, binding of HPs4 to the plate coated with LPS of group A *Pseudomonas aeruginosa* was inhibited by each LPS of group A and group L *Pseudomonas aeruginosa*; as shown in FIG. 4, binding of HPs5 to the plate coated with LPS of group H *Pseudomonas aeruginosa* was inhibited by each LPS of group G and group H *Pseudomonas aeruginosa*; as shown in FIG. 5, binding of HPs6 to the plate coated with LPS of group E *Pseudomonas aeruginosa* was inhibited by each LPS of group E and group F *Pseudomonas aeruginosa*; as shown in FIG. 6, binding of HPs7 to the plate coated with LPS of group A *Pseudomonas aeruginosa* was inhibited by each LPS of group A and group F *Pseudomonas aeruginosa*; and as shown in FIG. 7, binding of HPs8 to the plate coated with LPS of group E *Pseudomonas aeruginosa* was inhibited by each LPS of group E and group F *Pseudomonas aeruginosa*. From these results, it was confirmed that HPs4, HPs5, HPs6, HPs7 and HPs8 were human monoclonal antibodies of recognizing two O-antigens of groups A and L, groups G and H, groups E and F, groups A and F, groups E and F, respectively, in common.

EXAMPLE 13

Cross Reactivity of Human Monoclonal Antibodies with LPSs (3)

Cross reactivities of the human monoclonal antibodies HPs9, HPs10, HPs11 and HPs12 obtained in Example s 6, 7, 8 and 9 with O-antigens of *Pseudomonas aeruginosa* were examined by ELISA using a plate coated with LPS in a manner similar to Example 11. Binding of HPs9 to the plate coated with LPS of group I *Pseudomonas aeruginosa* was inhibited by each LPS of group D and group I *Pseudomonas aeruginosa*. Binding of HPs10 to the plate coated with LPS of group E *Pseudomonas aeruginosa* was inhibited by each LPS of group E and group F *Pseudomonas aeruginosa*. Binding of HPs11 to the plate coated with LPS of group H *Pseudomonas aeruginosa* was inhibited by each LPS of group G and group H *Pseudomonas aeruginosa*. Binding of HPs12 to the plate coated with LPS of group A *Pseudomonas aeruginosa* was inhibited by each LPS of group A and group F *Pseudomonas aeruginosa*. From these results, it was confirmed that HPs9, HPs10, HPs11 and HPs12 were human monoclonal antibodies of recognizing two O-antigens of groups D and I, groups E and F, groups G and H, and, groups A and F, respectively, in common.

EXAMPLE 14

Test for Promoting Effect of Human Monoclonal Antibody on Bactericidal Activity of Polymorphonuclear Cells against *Pseudomonas aeruginosa*

Promoting effect of human monoclonal antibody HPs2 obtained in Example 1 on bactericidal activity of mouse polymorphonuclear cells against *Pseudomonas aeruginosa* was examined. PBS containing 2.5% (w/v) glycogen was intraperitoneally injected in 2 ml/mouse to mice (Balb/c, female) of 8 to 12 weeks old after birth. Five hours after, peritoneal exudate cells (collected from 14 mice) containing polymorphonuclear cells were gathered. The peritoneal exudate cells containing polymorphonuclear cells were washed twice with Hanks' solution under ice cooling and dispersed in 10 mM HEPES-containing Hanks' balanced salt solution (hereafter simply referred to as HBSS) in a cell density of $1 \times 10^7$/ml, which was stored under ice cooling until it was provided for use. Group E *Pseudomonas aeruginosa* PA103 and group F *Pseudomonas aeruginosa* IID 1006 were inoculated on nutrient agar, respectively, followed by incubation at 37° C. for 20 hours. Grown colonies were scraped out and suspended in physiological salt solution. After washing twice with the same solution, the bacterial cells were suspended in HBSS to become absorbancy of 0.12 at a wavelength of 540 nm. The prepared bacterial cell suspensions were stored under ice cooling until it was provided for use. As complement a 5-fold dilution of guinea pig normal serum (lyophilized complement, Nihon Bloteat Laboratories) with HBSS was used.

Under ice cooling, 10 μl each of the bacterial cell suspension were separately charged in a plastic test tube (Falcon) and, 40 μl of HPs2 previously adjusted to concentrations of 25 μg/ml, 2.5 μg/ml and 0.25 μg/ml with HBSS and 10 μl of complement solution were added thereto. The mixture was thoroughly mixed. Next, 40 μl of peritoneal exudate cell suspension containing polymorphonuclear cells was added to the mixture. After thoroughly mixing, rotary shake culture (200 rpm) was carried out at 37° C. for 2 hours. After completion of the incubation, 900 μl of ice cooled water was added to each test tube to osmotically puncture polymorphonuclear cells. 100 μl each was taken out of each test tube and diluted to 10-fold, 100-fold and 1000-fold with HBSS. Each dilution was inoculated on nutrient agar plate (3 dishes) by 100 μl each followed by incubation at 37° C. for 18 hours. The number of colonies formed on the nutrient agar plate was counted to determine the remaining bacterial cell count. In the control group, HBSS was added instead of each addition solution. As shown in Tables 3 and 4, the results reveal that HPs2 promoted bactericidal activity of polymorphonuclear cells against different serotypes of group E and F *Pseudomonas aeruginosa* in the presence of complement.

TABLE 3

| Bactericidal Activity Against Group E *Pseudomonas aeruginosa* (PA103) | | | |
|---|---|---|---|
| Antibody (μg/ml) | Polymorphonuclear Cells | Complement | Count of Remained Viable Cells ($\times 10^5$ CFU/ml) |
| 0 | – | – | 9.1 |
| 0 | + | + | 16.0 |
| 0.01 | + | + | 4.7 |
| 0.1 | + | + | 0.56 |
| 1 | + | + | 0.65 |
| 10 | + | + | 0.12 |

*When started = $6 \times 10^5$ colony forming units (CFU)/ml

TABLE 4

Bactericidal Activity Against Group F
*Pseudomonas aeruginosa* (IID 1006)

| Antibody (μg/ml) | Polymorpho-nuclear Cells | Complement | Count of Remained Viable Cells (×10⁵ CFU/ml) |
|---|---|---|---|
| 0 | − | − | 0.41 |
| 0.1 | + | + | 0.040 |
| 1 | + | + | 0.073 |
| 10 | + | + | 0.073 |

*When started = $2.5 \times 10^5$ colony forming units (CFU)/ml

EXAMPLE 15

Test on Protective Activity of Human Monoclonal Antibody against *Pseudomonas aeruginosa* Infection (1)

Protective activity of the human monoclonal antibodies HPs1, HPs2, HPs4, HPs5, HPs6, HPs7 and HPs8 obtained in Examples 1, 2, 3, 4 and 5 against *Pseudomonas aeruginosa* infection was examined. The human monoclonal antibody was intraperitoneally injected to mice (Balb/c, female) of 8 to 12 weeks old after birth, one group being 5 to 10 mice, in 0.2 ml of a solution containing 50 ng, 500 ng, 5 μg and 50 μg of each human monoclonal antibody per mouse. Two hours after, bacterial suspension of each strain (IID 1001 (group A), IID 1004 (group D), PA 103 (group E), F7 (group F), P 28 (group G), IID 1009 (group H), IID 1010 (group I), and IID 1014 (group L)) was intraperitoneally challenged. In the control group, physiological salt solution alone was injected instead of the human monoclonal antibody. Each serotype *Pseudomonas aeruginosa* was inoculated on heart infusion agar plate medium followed by incubation at 37° C. overnight. Grown bacterial cell colonies were scraped out. After diluting with physiological salt solution, 5% mucin was added and adjusted to be a challenging bacterial amount of 3 to 15 times 50% lethal dose ($LD_{50}$ value) per mouse. After challenging *Pseudomonas aeruginosa*, 50% effective dose ($ED_{50}$ value) was determined based on survival rate of mice in each injection group on the 7th day. As shown in Table 5, the results reveal that each human monoclonal antibody had a high protective activity against infections with *Pseudomonas aeruginosa* of two different serotypes, each showing reaction specificity.

EXAMPLE 16

Test on Protective Activity of Human Monoclonal Antibody against *Pseudomonas aeruginosa* Infection (2)

Protective activity of the human monoclonal antibody HPs2 obtained in Example 1 against *Pseudomonas aeruginosa* infection was examined by varying time for injection of the antibody. The human monoclonal antibody HPs2 was intraperitoneally injected to mice (Balb/c, female) of 8 weeks old after birth, one group being 10 mice, in 0.2 ml of a solution containing 0.2 μg of HPs2 per mouse. The bacterial suspension of PA 103 (group E) was intraperitoneally challenged 24 hours and 2 hours prior to injection of the antibody, at the same time and 1 hour and 4 hours after. In the control group, physiological salt solution alone was injected instead of the human monoclonal antibody. The bacterial suspension was prepared in a manner similar to Example 15; i.e., after diluting with physiological salt solution, 5% mucin was added and adjusted to be a challenge bacterial amount of 8 times $LD_{50}$ per mouse. A survival rate of mice on the 3rd day after challenge of *Pseudomonas aeruginosa* was observed. As shown in Table 6, the results reveal that HPs2 showed protective activity against infection of group E *Pseudomonas aeruginosa* showing reaction specificity, except for injection four-hours after challenge of the bacterial solution. From the results, it was made clear that HPs2 had not only prophylactic effect but also therapeutic effect against *Pseudomonas aeruginosa* infection.

TABLE 6

| Antibody (μg/mouse) | Time Injected | Surviving Number (3 days after) | Survival Rate (%) |
|---|---|---|---|
| 0 | simultaneous | 0/10 | 0 |
| 0.2 | before 24 hours | 6/10 | 60 |
| 0.2 | before 2 hours | 10/10 | 100 |
| 0.2 | simultaneous | 9/10 | 90 |
| 0.2 | 1 hour after | 6/10 | 60 |
| 0.2 | 4 hours after | 1/10 | 10 |

EXAMPLE 17

Production of Lyophilized Preparation

HPs2 obtained in Example 1 was dissolved in PBS containing 0.2% (w/v) human serum albumin (Calbio) in a concentration of 1 mg/ml. The solution was filtered through membrane filter having a pore size of 0.22 microns for sterilization. The filtrate was aseptically charged in a vial by 1 ml each and lyophilized to produce a lyophilized prepa-

TABLE 5

| Monoclonal Antibody | $ED_{50}$ value (μg/mouse) [Serotype of Challenge Bacteria] | | | | | | | |
|---|---|---|---|---|---|---|---|---|
| | A | D | E | F | G | H | I | L |
| HPs1 | >50 | 0.5 | — | — | — | — | 5.0 | — |
| HPs2 | >50 | — | 0.055 | 0.1 | — | — | — | — |
| HPs4 | 0.1 | — | — | — | — | >50 | — | 0.1 |
| HPs5 | >50 | — | — | — | 0.08 | 0.1 | — | — |
| HPs6 | >50 | — | 0.08 | 0.1 | — | — | — | — |
| HPs7 | 0.5 | — | — | 0.5 | — | >50 | — | — |
| HPs8 | >50 | — | 0.1 | 0.1 | — | — | — | — | ration. The preparation was again dissolved in distilled water and titer to *Pseudomonas aeruginosa* was measured; its activity was maintained.

The novel immunoglobulin-non-producing mutant of the present invention can be obtained by producing a mass of mutants through manipulation for mutation, such as variation or deletion of the chromosome from known human hybridomas, e.g., KR-12, etc., screening from the cell mass the presence of cells of which all or a part of the capability of producing human immunoglobulin is deleted and isolating a single cell line through cloning. Furthermore, by allowing again to cause mutation on the cells during the course of cloning or on the isolated single cell line and repeating cloning, a single cell line of which all or a part of the capability of producing human immunoglobulin is deleted can be isolated. Finally by adapting to a medium containing 8-azaguanine and ouabain, the novel immunoglobulin-non-producing mutant can be produced.

As the human immunoglobulin-producing cell line used in the present invention, there are, in addition to the known cell lines such as KR-12, etc. described above, a variety of human myeloma cells, human lymphoblasts or human hybridomas newly produced by fusion of these cells. KR-12 used in the present invention is available from ATCC (American Type Culture Collection) as CRL 8658.

Mutation for variation or deletion of the chromosome can be performed by environmental change through manipulation such as a plurality of operations for freezing and thawing, overdensity culture, low oxygen concentration culture, low temperature or high temperature culture, change in culture temperature in a short period of time, etc., or by irradiating ultraviolet rays, radiation, etc. in a pulse interval or continuously. The mutation can also be effected by adding mutagenic chemicals such as 8-azaguanine, 6-thioguanine, colchicine, ethylmethane sulfonate (EMS), N-methyl-N'-nitro-N-nitrosoguanidine (MNNG), acridine mastard, etc. to a medium in a definite amount. These methods are applied singly or in appropriate combination to effectively induce variation or deletion of the chromosome.

Cell culture can be carried out by dispersing in a medium in a cell density of, e.g., $5 \times 10^4$/ml to $2 \times 10^6$/ml, inoculating the culture solution on an appropriate cell culture vessel and culturing at 37° C. in the presence of 5% carbon dioxide gas. Preferred examples of the medium include those obtained by supplementing basal medium such as RPMI 1640, Dulbecco modified Eagle's medium (DMEM), etc. with a suitable amount of fetal calf serum (FCS). In addition, various serum-free media can also be used. For example, NYSF 404 serum-free medium supplemented with an appropriate amount of bovine serum albumin is recommended. In subculture, it is preferred to repeat the operation of cell recovery and inoculation in an interval of 3 to 7 days.

Freezing of the cells can be carried out in a conventional manner. For example, the cells are dispersed in a suitable frozen cell storage solution in a cell density of $1 \times 10^5$/ml to $5 \times 10^7$/ml and the dispersion is frozen and stored in liquid nitrogen or liquid nitrogen gas or in a refrigerator at −20° to −80° C. It is recommended to use as the frozen cell storage solution one prepared by adding a suitable amount of animal serum or albumin, glucose, dimethyl sulfoxide (DMSO), etc. to the basal medium described above, neutral buffer solution, etc.

Operations for thawing the frozen cells, treatment after thawing and reincubation can be performed in a conventional manner. For example, the frozen cells are rapidly thawed in warm water. The cells after the thawing the cells are washed with a medium, etc. to wash off DMSO contained in the storage solution. Then, the cells are dispsersed in a medium followed by incubation.

Cloning of the cell line of the present invention from the mutants can be performed by the soft agar method ["Studies on Applied Tissue Culture", page 289 (1985) published by Soft Science Co., Ltd., etc.] or the limiting dilution method ["Monoclonal Antibody", page 73 (1983), published by Kodansha Publishing Co., Ltd., etc.]. In cloning according to, e.g., the limiting dilution method, the cell mass on which mutation was induced is dispersed in a medium containing 20% FCS and the dispersion is inoculated on a 96 well flat bottom plate on which mouse spleen cells are inoculated as feeder cells (hereafter simply referred to as the feeder plate) in one per well followed by culturing at 37° C. in the presence of 5% carbon dioxide gas. With respect to the well in which proliferation is noted as a single colony, the amount of human immunoglobulin in the culture supernatant is subjected to screening. With respect to the cells in the well in which production of human immunoglobulin is not noted, cloning is again performed by the limiting dilution method. By repeating the cloning operation several times, a cell line secreting no human immunoglobulin can be obtained as a single cell mass. By adding a chemical that kills the cells with hypoxanthine phosphate ribosyl transferase (hereafter simply referred to as HGPRT) to the medium in cloning, HGPRT-deficient cells can be efficiently selected. As such a chemical, 8-azaguanine or the like is preferred.

Screening of human immunoglobulin in the culture supernatant can be performed by conventional radioimmunoassay or enzyme-linked immunosorbent assay (ELISA), etc. In the case of using, e.g., ELISA, anti-human immunoglobulin antibody is immobilized onto a solid phase (the antibody used in this case is hereafter simply referred to as immobilized antibody) and a part of the culture supernatant is reacted with it. Next the reaction product is reacted with enzyme-labeled anti-human immunoglobulin antibody and substrate is added thereto. By measuring the color formed by the enzyme reaction, human immunoglobulin in the culture supernatant can be detected and the quantity of human immunoglobulin can be determined. Determination of human gamma chain, human lambda chain or human kappa chain can be carried out by using as the immobilized antibody anti-human IgG (human gamma chain-specific) antibody, anti-human lambda chain antibody or anti-human kappa chain antibody, and using as the enzyme-labeled antibody peroxidase-labeled anti-human IgG (human gamma chain-specific) antibody, peroxidase-labeled anti-human lambda chain antibody or peroxidase-labeled anti-human kappa chain antibody, respectively.

The parent cell line of the present invention is dead in a medium containing hypoxanthine, aminoputerine and thymidine (HAT medium) or in a medium containing hypoxanthine and azaserine (HA medium). This HGPRT-deficient property can be maintained by culturing in a medium containing 8-azaguanine in a concentration of 10 μg/ml to 100 μg/ml. Furthermore, the parent cell line is not dead in a medium containing ouabain in a concentration of 10 μM. Based on this selectivity property, human hybridomas between the parent cell line of the present invention and human antibody-producing cells can be produced. Furthermore, the resulting human hybridomas can secrete only the antibodies substantially derived from the human antibody-producing cells into the medium.

The parent cell line of the present invention can be subcultured using the medium described above. The parent cell line of the present invention can also be stably stored using the storage solution described above over a long period of time.

Fusion between the cells of the present invention and human antibody-producing cells can be carried out using conventional chemicals for fusion such as polyethylene glycol (hereafter simply referred to as PEG) or viral particles such as Sendai virus (Hemagglutinating Virus of Japan: HVJ), etc. For example, a solution obtained by adding PEG having a mean molecular weight of approximately 1000 to 6000 to RPMI 1640 medium or DMEM medium in a concentration of 30 to 50% (W/V) is preferred as a fusing solution. In order to further enhance a fusion efficiency, it is also preferable to add DMSO to the fusing solution. The fusion can also be effected by physical means using an electrofusion apparatus, etc. In the cell fusion, it is desired to use the human antibody-producing cells in an amount of 1 to 10 times that of the cells of the present invention. As the human antibody-producing cells, a cell mass transformed by Epstein-Barr virus (hereafter simply referred to as EB virus) and a single EB virus transformant obtained from the transformed cell mass by cloning can be used. In addition, lymphocyte fraction and human B cell fraction containing human antibody-producing cells derived from human antibody-producing cells obtained by stimulation and proliferation of these fractions with mitogen or antigen, etc. can be used as the human antibody-producing cells for cell fusion.

By the methods described above, the human antibody-producing cells are fused with the cells of the present invention. The fused cells are separately charged onto a culture plate of 24 wells or 96 wells followed by culturing in the selection medium at 37° C. in the presence of 5% carbon dioxide gas. During the culture, it is preferred to exchange half or the selection medium with a fresh selection medium at 3 to 5 day intervals. In this case, when mouse peritoneal exudate cells or the like are allowed to co-exist as the feeder cells, proliferation of human hybridomas can be accelerated. From the cell mass, the human hybridomas can be selected by the selection medium. If the human antibody-producing cells have no infinite limiting proliferation ability, HAT medium or HA medium can be used as the selection medium. When the human antibody-producing cells have infinite proliferation ability like EB virus transformants, etc., HAT medium or HA medium containing ouabain can be used as the selection medium.

The present invention is now described in more detail by referring to the following non-limiting examples.

EXAMPLE 18

Production of Human Immunoglobulin-non-producing Cell Line (1)

(1) Production of the mutant cell line

Human hybridoma ATCC CRL 8658 was suspended in 10 ml of RPMI 1640 medium containing 10% FCS (hereafter simply referred to as 10% FCS culture medium) in a density of $1 \times 10^5$ cells/ml. The suspension was inoculated on a plastic culture flask having a bottom area of 75 cm$^2$ (75T flask, Coaster) followed by stationary culture at 37° C. for 5 days in the presence of 5% carbon dioxide gas.

The culture was trasferred to a plastic centrifuging tube having a 15 ml volume (Corning). The cells were collected by centrifugation (200×g, 10 minutes) and suspended in RPMI 1640 medium containing 75% FCS and 10% DMSO (hereafter simply referred to as freeze storage solution) in a density of $1 \times 10^6$ cells/ml. After 1 ml/tube of the cell suspension was separately charged in a stock tube (Corning) having a 2 ml volume, the suspension was settled at −20° C. for an hour to freeze and were then stored at −80° C.

The frozen cell suspension in the stock tube was thawed while gently stirring in a hot bath of 37° C. The thawed cell suspension was transferred to a plastic centrifuging tube having a 15 ml volume and washed twice with 10 ml of 10% FCS culture medium. After inoculation on a 75T flask, stationary culture was carried out. The foregoing operations for cell culture (5 days) and freeze storage (2 days) were continuously performed over 6 weeks.

The frozen cell suspension was thawed and the cells were washed twice with 10 ml of 10% FCS culture medium. Thereafter, the cells were suspended in 10 ml of 10% FCS culture medium in a density of $5 \times 10^4$ cells/ml. After incoculation on a 75T flask stationary culture was carried out for 4 days. The cells were collected by centrifugation and suspended in 1 ml of 10% FCS culture medium containing EMS of a concentration of 200 μg/ml. After inoculation on one well of a 6 well culture plate (Coaster), stationary culture was carried out for 24 hours. The culture was centrifuged and washed twice with 10 ml of 10% FCS culture medium. Thereafter the cells were suspended in 12 ml of 10% FCS culture medium. After inoculation on a 75T flask, stationary culture was carried out for 4 days. The culture was centrifuged and washed twice with 10 ml of 10% FCS culture medium to give $6.0 \times 10^5$ of cells. The cells were suspended in 6 ml of 10% FCS culture medium. After inoculation on a 75T flask, stationary culture was carried out for 3 days. The culture was centrifuged to give $7.0 \times 10^5$ of mutation-induced cells.

(2) Screening and cloning

The mutation-induced cells were suspended in 20% FCS culture medium containing 15 μg/ml of 8-azaguanine (Tokyo Chemical Co., Ltd.) in a density of 10 cells/ml and 0.1 ml each of the suspensions was inoculated on each well of 10 plates of a 96 well flat bottom culture plate (Corning) on which $1 \times 10^5$ of mouse spleen cells had been previously inoculated as feeder cells followed by stationary culture. Two or three weeks after, the culture supernatant was collected in order from the wells in which colonies had sufficiently proliferated as a single clone. The presence or absence of human immunoglobulin in the culture supernatant was determined by screening in accordance with ELISA using a 96 well flat bottom plate (Greiner) for EIA and using goat anti-human immunoglobulin antibody (Tago) as immobilized antibody solution and peroxidase-labeled goat anti-human immunoglobulin antibody (Tago) as enzyme-labeled antibody. As the result, human gamma chain was not detected in the culture supernatant in ten wells (1C3, 1G10, 3F6, 3H2, 4B11, 5C5, 7A8, 8D1, 8H7 and 10F8) out of the 250 wells in which cell growth was noted.

The cells in the ten wells were independently collected and suspended in 20% FCS culture medium in a density of 10 cells/ml. After inoculating 0.1 ml each on each well of a feeder plate in one plate per one cell line, stationary culture was carried out. Two or three weeks after, the culture supernatant was collected in order from the wells in which colonies had proliferated as a single clone. The production of human gamma chain in the culture supernatant was determined by screening in accordance with ELISA. As the result, the production of human gamma chain was not detected in all of the culture supernatant in 68 wells in which colonies were proliferated as a single clone, in the plate inoculated with 7A8. With respect to the cells in the wells in which the production of human gamma chain was not noted, similar cloning operations were again repeated to give one single cell line. The cell line was named MP 4109. MP 4109 has been deposited under the terms of the Budapest Treaty in Fermentation Research Institute of the Agency of Industrial Science and Technology of Japan as Deposit Number FERM BP-2129.

EXAMPLE 19

Production of Human Immunoglobulin-non-producing Cell Line (2)

(1) Production of the mutant cell line

The cells in ten wells (1C3, 1G10, 3F6, 3H2, 4B11, 5C5, 7A8, 8D1, 8H7 and 10F8) from which no human gamma chain was detected in Example 18 were collected and suspended in 5 ml of 20% FCS culture medium. The suspension was inoculated on a culture flask having a bottom area of 25 cm² (25T flask, Corning) followed by stationary culture for 4 days. The cells were collected by centrifugation to give $3 \times 10^6$ cells. The cells were suspended in 3 ml of 10% FCS culture medium containing MNNG of a concentration of 0.5 µg/ml and 1 ml each of the suspension was separately charged in 3 wells of a 6 well culture plate followed by stationary culture for 24 hours. The cultures in the 3 wells were centrifuged and washed twice with 10% FCS culture medium to give $3.2 \times 10^6$ cells, from which $1 \times 10^6$ cells were suspended in 10 ml of 10% FCS culture medium. After inoculation on a 75T flask, stationary culture was carried out for 2 days. The culture was centrifuged to give $1.2 \times 10^6$ cells. The cells were suspended in 10 ml of 10% FCS culture medium. After inoculation on a 75T flask, stationary culture was carried out for 2 days. The culture was centrifuged to give $5.5 \times 10$ cells. The cells were suspended in 5 ml of 10% FCS culture medium. After inoculation on a 25T flask, stationary culture was carried out for 2 days. The culture was centrifuged to give $2.5 \times 10^5$ cells. The cells were suspended in 2 ml of 10% FCS culture medium and 1 ml each of the suspension was separately charged in 2 wells of a 6 well culture plate followed by stationary culture for 2 days. The culture was centrifuged to give $7.0 \times 10^5$ of mutation-induced cells.

(2) Screening and cloning

The mutation-induced cells were washed once with 10% FCS culture medium and suspended in 10% FCS culture medium in a density of 40 cells/ml. 0.1 ml each of the suspension was inoculated on each well of 4 plates of 96½ well flat bottom culture plate (Corning) on which $1 \times 10^5$ of mouse spleen cells had been previously inoculated as feeder cells followed by stationary culture for 15 days. During the culture, half of the medium was exchanged with a fresh medium at 3 to 4 day intervals. The culture supernatant was collected from the wells in which colonies had sufficiently proliferated as a single clone. The presence or absence of human immunoglobulin in the culture supernatant was determined by screening in accordance with ELISA.

With respect to the culture supernatant in 285 wells in which colonies were proliferated as a single clone, the quantity of human immunoglobulin was determined. As the result, the production of human gamma chain, human lambda chain and human kappa chain was negative in the culture supernatant from 4 wells (S1A6, S2C10, S2G7 and S4D3); the production of human gamma chain and human lambda chain was negative in the culture supernatant from 2 wells (S2E7, S4E2); and the production of human gamma chain and human kappa chain was negative in the culture supernatant from 1 well (S1F5). The cells in each well were cultured on an enlarged scale and the quantity of human immunoglobulin in the resulting culture supernatant was again determined. As the result, the culture supernatant in the well on which the cells in S4D3 were inoculated showed negative production of human kappa chain and the culture supernatant in the well on which the cells in S2E7 were inoculated showed negative production of human lambda chain. Next, the cells in S2E7 were suspended in 10% FCS culture medium in a density of 20 cells/ml and again cloned (using 4 feeder plates). Sixteen days after inoculation, with respect to the wells in which colonies had sufficiently proliferated as a single clone, the presence or absence of human immunoglobulin in the culture supernatant was determined by screening in accordance with ELISA. The production of human gamma chain and human lambda chain was negative in the culture supernatant from 17 wells (1D3, 2A9, 2F7, 4B2, etc.) out of 23 wells assayed. The next day, the cells in 4B2 were cloned (using 3 feeder plates). Sixteen days after inoculation, with respect to the wells in which colonies were sufficiently proliferated as a single clone, the presence or absence of human immunoglobulin in the culture supernatant was determined by screening in accordance with ELISA. The production of human kappa chain was positive but the production of human gamma chain and human lambda chain was negative, in all of the culture supernatants from the assayed 281 wells. From them, a single cell line having excellent proliferation was selected and named MP 4112. MP 4112 has been deposited under the terms of the Budapest Treaty in Fermentation Research Institute of the Agency of Industrial Science and Technology of Japan as Deposit Number FERM BP-2128.

EXAMPLE 20

Production of Human Immunoglobulin-non-producing Cell Line (3)

(1) Production of the mutant cell line

The cell line incapable of synthesizing human gamma chain and human lambda chain of immunoglobulins was isolated from human hybridoma ATCC CRL 8658 in a manner similar to Example 18. The $5 \times 10^5$ cells of this cell line were suspended in 5 ml of 10% FCS culture medium containing EMS of a 150 µg/ml concentration, The suspension was inoculated on a 25T flask followed by stationary culture for 24 hours. The cells were collected by centrifugation to give mutation-induced cells.

(2) Screening and cloning

The mutation-induced cells were washed twice with 10% FCS culture medium and suspended in a density of $1.2 \times 10^6$ cells/ml. 0.1 ml of the suspension was added to and mixed with 24 ml of the 20% FCS culture medium containing 0.3% agarose (Sea Plaque agarose, F.M.C. Inc.). Next, 3 ml of the culture medium containing cells were charged and solidified on 6 cm Petri dishes (7 dishes) which had been previously solidified by charging 4 ml each of the 16.7% FCS medium containing 0.5% agarose. The 6 cm Petri dish charged with the cells was subjected to stationary culture at 37° C. in the presence of 5% carbon dioxide gas. Two weeks after, the cells were proliferated in soft agar and colones were observed with the naked eye. Each colony was transferred to each well of a 96 well flat bottom culture plate, in which 0.1 ml per well of the 20% FCS medium had previously been charged, using a Pasteur pipette. Two days after, 0.1 ml of the 20% FCS medium was supplemented and a further 3 days after, the culture supernatant was collected. The presence or absence of human kappa chain in the culture supernatant was determined by screening using ELISA.

With respect to the culture supernatant in 432 wells, the quantity of human kappa chain was determined. As the result, the production of human kappa chain was negative in the supernatant from 4 wells (2F10, 2G9, 3E9, 4H7). The cells in each well were cultured on an enlarged scale and the quantity of human kappa chain in the resulting culture supernatant was again determined. As the result, the culture supernatant in the well on which the cells in 2G9 were inoculated showed negative production of human kappa chain. Next, the cells in 2G9 were suspended in 10% FCS culture medium in a density of 40 cells/ml and inoculated on each well of 3 plates of 96½ well flat bottom culture plate on which 1×10⁵ of mouse spleen cells had been previously inoculated as feeder cells followed by stationary culture for 8 days. Nine days after inoculation, with respect to the wells in which colonies were sufficiently proliferated as a single clone, the presence or absence of human immunoglobulin in the culture supernatant was determined by screening in the accordance with ELISA. The production of human kappa chain was negative, in all of the culture supernatants from the assayed 184 wells. From them, a single cell line having excellent proliferation was selected and named MP 4126. MP 4126 has deposited under the terms of the Budapest Treaty in Fermentation Research Institute of the Agency of Industrial Science and Technology of Japan as Deposit Number FERM BP-2615.

EXAMPLE 21

Measurement of Chromosomal Count

Distribution in the chromosomal count of MP 4109, MP 4112 and MP 4126 was determined in a manner similar to the Yoshida method ["Practical Manual for Utilization of Animal Cells", page 337 (1984), Realize Co., Ltd.].

MP 4109, MP 4112 and MP 4126 in the log phase were collected and approximately $1 \times 10^6$ cells were cultured for 90 minutes in 10% FCS culture medium containing 0.1 µg/ml of colcemid (Sigma). After culture, centrifugation was performed (200×g, 5 minutes) and 5 ml of 0.075M potassium chloride aqueous solution was added to the cell residue. The mixture was gently agitated and allowed to stand at 37° C. for 20 minutes. After allowing it to stand, 1 ml of a fixing fluid (Carnoy's solution; methanol:acetic acid=3:1) was added and the mixture was gently agitated followed by allowing it to stand at 4° C. for 30 minutes. Next, centrifugation was performed (180×g, 5 minutes) and 3 ml of the culture supernatant was removed. The same amount of fixing solution was added followed by agitation. The amounts of the culture supernatant to be removed after centrifugation increased to 4, 5 and 6 ml, repeating the same operations. Lastly, 0.5 ml of fixing solution was added to the cell residue to form a suspension. Several drops of the suspension were dropped onto a glass slide. After allowing it to stand on a boiling water bath for about 1 minute, the glass slide was dried in the air at room temperature.

After the glass slide was immersed for 15 minutes in Gimsa solution diluted with ¹⁄₁₅M phosphate buffer (pH 7.0) to 20-fold, superfluous staining solution was washed out with tap water followed by drying. After drying, an inclusion chemical was added dropwise and the glass slide was covered with a cover glass. A picture was taken under an optical microscope to count chromosomes. As shown in Tables 7, 8 and 9, MP 4109, MP 4112 and MP 4126 had modes on 89, 75 and 73 counts of chromosome, respectively.

TABLE 7

Distribution of chromosome in MP 4109

| Number of Sample | 1 | 6 | 2 | 9 | 3 | 4 | 5 | 13 | 15 | 10 | 10 | 16 | 6 | 6 | 1 | 3 | 1 |
|---|---|---|---|---|---|---|---|---|---|---|---|---|---|---|---|---|---|
| Count of Chromosome | 78 | 79 | 80 | 81 | 82 | 83 | 84 | 85 | 86 | 87 | 88 | 89 | 90 | 91 | 92 | 93 | 100 |

Total number of samples = 126

TABLE 8

Distribution of chromosome in MP 4112

| Number of Sample | 1 | 2 | 1 | 1 | 1 | 1 | 1 | 2 | 2 | 1 | 2 | 2 | 1 | 4 | 7 | 5 | 3 | 10 | 8 | 8 | 3 |
|---|---|---|---|---|---|---|---|---|---|---|---|---|---|---|---|---|---|---|---|---|---|
| Count of Chromosome | 51 | 56 | 58 | 59 | 61 | 62 | 63 | 64 | 65 | 67 | 68 | 69 | 70 | 71 | 72 | 73 | 74 | 75 | 76 | 77 | 78 |

Total number of samples = 66

TABLE 9

Distribution of chromosome in MP 4126

| Number of Sample | 1 | 1 | 1 | 2 | 1 | 1 | 1 | 2 | 2 | 2 | 1 | 2 | 3 | 2 | 6 | 2 | 4 | 1 | 1 | 1 | 2 |
|---|---|---|---|---|---|---|---|---|---|---|---|---|---|---|---|---|---|---|---|---|---|

TABLE 9-continued

Distribution of chromosome in MP 4126

| Count of Chromosome | 48 | 55 | 56 | 57 | 61 | 63 | 64 | 65 | 66 | 68 | 69 | 70 | 71 | 72 | 73 | 74 | 76 | 77 | 78 | 79 | 80 |
|---|---|---|---|---|---|---|---|---|---|---|---|---|---|---|---|---|---|---|---|---|---|
| Number of Sample | 1 | 4 | 3 | 3 | 1 | 1 | 1 | 1 | 1 | 1 | 1 | 1 | 1 | 1 | 1 | 1 | 1 | | | | |

| Count of Chromosome | 81 | 82 | 83 | 84 | 85 | 87 | 90 | 96 | 97 | 104 | 109 | 112 | 125 | 127 | 134 | 150 |
|---|---|---|---|---|---|---|---|---|---|---|---|---|---|---|---|---|

Total number of samples = 62

EXAMPLE 22

Measurement of Human Immunoglobulin Synthesized and Secreted

A sample for measuring the amount of human immunoglobulin secreted out of the cells by MP 4109, MP 4112 and MP 4126 was prepared as follows. The cells in the log phase were collected and suspended in 10% FCS culture medium in a density of $1\times10^6$ cells/ml. 0.1 ml each was inoculated on each well of a 6 well culture plate and subjected to stationary culture at 37° C. in the presence of 5% carbon dioxide gas. Twenty four hours after, the culture supernatant was separated by centrifugation (250×g, 10 minutes) and provided as a sample. ATCC CRL 8658 was cultured in a similar manner prepare a positive control sample for secreting human gamma chain, human lambda chain and human kappa chain.

A sample for determining an amount of human immunoglobulin synthesized intracellularly in MP 4109 was prepared as follows. The cells in the log phase were collected ($1\times10^7$ cells) and suspended in 1 ml of phosphate buffer containing 1% polyoxyethylene sorbitan monolaurate (Sigma) followed by homogenization with a potter type homogenizer. The homogenate was centrifuged (50,000×g, 30 minutes) and the resulting supernatant was filtered throght a filter of 0.22 μm and provide as a sample. ATCC CRL 8658 was treated in a similar manner to prepare a positive control sample for synthesizing human gamma chain, human lambda chain and human kappa chain. Furthermore, Raji cells were treated in a similar manner to prepare a negative control sample incapable of synthesizing human immunoglobulin. The amounts of human gamma chain, human lambda chain and human kappa chain in the samples were determined by ELISA.

Human gamma chain was not detected in the culture supernatant of MP 4109 and the cell homogenate. The amounts of human lambda chain and human kappa chain secreted by MP 4109 into the culture were all approximately ⅓ that of ATCC CRL 8658. Human gamma chain and human lambda chain were not detected in the culture supernatant of MP 4112 and the cell homogenate. The amounts of human kappa chain secreted by MP 4112 into the culture supernatant were all approximately ⅓ that of ATCC CRL 8658. Human gamma chain, human lambda chain and human kappa chain were not detected in the culture supernatant of MP 4126 and the cell homogenate.

EXAMPLE 23

Measurement of Cell Doubling Time

MP 4109, MP 4112 and MP 4126 in the log phase were collected and suspended in 10% FCS culture medium in a density of $5\times10^4$ cells. 0.1 ml each was inoculated on each well of a 6 well culture plate and subjected to stationary culture at 37° C. in the presence of 5% carbon dioxide gas. The cell count in the well was accurately counted once a day using a hemocytometer. The number of the cells in 3 wells was counted every time. The doubling time of MP 4109, MP 4112 and MP 4126 in the log phase determined from the mean value was 24.6, 25.6 and 20.5 hours, respectively.

EXAMPLE 24

Production of Human Hybridoma (1)

The culture supernatant of B95-8 cells (marmoset lymphoblast capable of producing infectious EB virus) was added to the human antibody-producing cells (lymphocytes) separated from the peripheral blood of a healthy donor to infect with EB virus. Then, the cells in the well in which the production of human IgM in the culture supernatant was noted were cloned and the resulting human IgM-producing human lymphoblast 87H4G was used as a partner for fusion to produce a human hybridoma. Human IgM-producing human lymphoblast which had been previously proliferated in 10% FCS culture medium and MP 4109 were washed with RPMI 1640 medium, respectively. In a plastic centrifuging tube of 50 ml volume, $3\times10^7$ human lymphoblast and the same count of MP 4109 cells were mixed with each other. After centrifugation (175×g, 10 minutes), the culture supernatant was removed by suction and 0.5 ml of RPMI 1640 medium containing 50% PEG (molecular weight of 1500, Wako Pure Chemical) and 10% DMSO was gently charged and slowly rotated to cause cell fusion. Two minutes after, 10 ml of RPMI 1640 medium was added. After gently agitating the mixture, centrifugation was carried out (175×g, 10 minutes). The culture supernatant was removed by suction and 20% FCS culture medium supplemented with $2\times10^{-4}$M hypoxanthine (Sigma), 1 μg/ml azaserine (Sigma) and 5 μM ouabain (Sigma) (hereafter simply referred to as HA-O medium) was added to the culture supernatant to form a cell suspension in a density of $1\times10^6$ cells/ml. 0.1 ml each per well of the suspension was inoculated on a 96 well flat bottom culture plate (627 wells in total). The cells were subjected to stationary culture at 37° C. in the presence of 5% carbon dioxide gas. Four days after, 0.1 ml of HA-O medium was added and thereafter, the half of the HA-O medium was exchanged by a fresh HA-O medium at 4 to 5 day intervals. The number of wells in which proliferation of colonies of human hybridoma was noted until 7 weeks thereafter was 78 out of 627 wells. Frequency in fusion was calculated to be $2.6\times10^{-6}$.

From the wells in which the proliferation of colonies was noted, 4 wells were chosen at random and human hybridoma was cultured in an increasing scale toward a 24 well plate, a 6 well plate, a 6 cm Petri dish and 75T flask. Four human hybridomas were suspended in 20% FCS culture medium, respectively, in a density of 1×10⁶ cells/ml. One ml each per well of the suspension was inoculated on a 6 well plate. The cells were subjected to stationary culture at 37° C. in the presence of 5% carbon dioxide gas. Twenty four hours after, centrifugation was performed (200×g, 10 minutes) and the culture supernatant was separated. The amounts of human mu chain and human gamma chain in the culture supernatant were determined by ELISA. The results are shown in Table 10. All of the human hybridomas secreted human mu chain, which was a heavy chain derived from human IgM-producing human lymphoblast, but did not secrete the other heavy chain (human gamma chain).

TABLE 10

Results of Measurement on Amount of Antibody secreted by MP 4109-derived Human Hybridoma

| Human Hybridoma | Amount of antibody Secreted ($\mu$g/10⁶ cells/24 hrs) | |
|---|---|---|
|  | Human Mu Chain | Human Gamma Chain |
| 2S3B12 | 18.3 | <0.001 |
| 2S4B7 | 21.1 | <0.001 |
| 2S7A2 | 33.3 | <0.001 |
| 2S6B1 | 18.6 | <0.001 |

EXAMPLE 25

Production of Human Hybridoma (2)

In a manner similar to Example 24, 3×10⁷ counts of human IgM-producing human lymphoblast 87H4G were fused with the same cells of MP 4112. The number of wells in which proliferation of colonies of human hybridoma was noted until 7 weeks thereafter was 69 out of 610 wells. Frequency in fusion was calculated to be 2.4×10⁻⁶.

From the wells in which the proliferation of colonies was noted, 4 wells were chosen at random and human hybridoma was cultured in an increasing scale toward a 24 well plate, a 6 well plate, a 6 cm Petri dish and a 75T flask. Four human hybridomas were suspended in 20% FCS culture medium, respectively, in a density of 1×10⁶ cells/ml. One ml each per well of the suspension was inoculated on a 6 well plate. The cells were subjected to stationary culture at 37° C. in the presence of 5% carbon dioxide gas. Twenty four hours after, centrifugation was performed (200×g, 10 minutes) and the culture supernatant was separated. The amounts of human mu chain and human gamma chain in the culture supernatant were determined by ELISA. The results are shown in Table 11. All of the human hybridomas secreted human mu chain, which was a heavy chain derived from human IgM-producing human lymphoblast 87H4G but did not secrete other heavy chain (human gamma chain).

TABLE 11

Results of Measurement on Amount of Antibody Secreted by MP 4112-derived Human Hybridoma

| Human Hybridoma | Amount of Antibody Secreted ($\mu$g/10⁶ cells/24 hrs) | |
|---|---|---|
|  | Human Mu Chain | Human Gamma Chain |
| 3N1A8 | 25.6 | <0.001 |
| 3N3C6 | 15.8 | <0.001 |
| 3N3E12 | 28.2 | <0.001 |

TABLE 11-continued

Results of Measurement on Amount of Antibody Secreted by MP 4112-derived Human Hybridoma

| Human Hybridoma | Amount of Antibody Secreted ($\mu$g/10⁶ cells/24 hrs) | |
|---|---|---|
|  | Human Mu Chain | Human Gamma Chain |
| 3N5A3 | 35.5 | <0.001 |

EXAMPLE 26

Production of Human Hybridoma (3)

The culture supernatant of B95-8 cells was added to the human antibody producing cells (lymphocytes) separated from the peripheral blood of a healthy donor to infect with EB virus. Then the cells in the well in which the production of human IgM in the culture supernatant was noted were cloned and the resulting human IgM (human mu chain and lambda chain)-producing human lymphoblast 87L8GNM was produced.

In a manner similar to Example 24, 2.5×10⁷ cells of 87L8GNM was fused with the same counts of MP 4126. The number of wells in which proliferation of colonies of human hybridoma was noted until 7 weeks thereafter was 6 out of 480 wells. As the result, frequency in fusion was calculated to be 2.4×10⁻⁷.

From the wells in which the proliferation of colonies was noted, 4 wells were chosen at random and human hybridoma was cultured in an increasing scale toward a 24 well plate, a 6 well plate, a 6 cm Petri dish and a 75T flask. Four human hybridomas were suspended in 20% FCS culture medium, respectively, in a density of 1×10⁶ cells/ml. One ml each per well of the suspension was inoculated on a 6 well plate. The cells were subjected to stationary culture at 37° C. in the presence of 5% carbon dioxide gas. Twenty four hours after, centrifugation was performed (200×g, 10 minutes) and the culture supernatant was separated. The amount of human mu chain and the amounts of human gamma chain in the culture supernatant were determined by ELISA. The results are shown in Table 6. All of the human hybridomas secreted only human mu chain which were heavy chain derived from human IgM-producing human lymphoblast, but secreted no other heavy chain (human gamma chain). The amount of human kappa chain and human lambda chain in the culture supernatant were determined by ELISA. Human lambda chain was detected, but human kappa chain was not detected.

TABLE 12

Results of Measurement on Amount of Antibody Secreted by MP 4126-derived Human Hybridoma

| Human Hybridoma | Amount of Antibody Secreted ($\mu$g/10⁶ cells/24 hrs) | |
|---|---|---|
|  | Human Mu Chain | Human Gamma Chain |
| 4C1H9 | 17.8 | <0.001 |
| 4C2F1 | 21.3 | <0.001 |
| 4C2G6 | 30.6 | <0.001 |
| 4C3B12 | 12.2 | <0.001 |

1. *Pseudomonas aeruginosa* used:

For convenience, the classification of *Pseudomonas aeruginosa* used in the present invention follows the serologic classification by the Serotyping Comittee for the Japan *Pseudomonas aeruginosa* Society as stated above. In the present invention, strains belonging to group A to group M are used.

Strains belonging to group A to group M can be acquired from the American Type Culture Collection (ATCC) and the Medical and Science Research Institute of Tokyo University.

2. Production of human-human hybridoma:

Human-human hybridomas capable of producing human monoclonal antibodies having reactivities respectively with groups A, B, E, G and I of *Pseudomonas aeruginosa* in the serologic classification by the Serotyping Comittee for the Japan *Pseudomonas aeruginosa* Society can be produced by fusing cells of the parent cell line MP 4109 or its subcultured cell line for producing hybridoma with human antibody producing cells, in a manner similar to a known method [textbook "MONOCLONAL ANTIBODIES", page 363, published by Plenum Press (1980) and the like]. As the human antibody producing cells, there may be used B cells obtained from the peripheral blood, lymph node, tonsil or spleen of healthy donors observed to be able to produce antibodies to *Pseudomonas aeruginosa* or patients with a past history of *Pseudomonas aeruginosa* infectious diseases or, from cord blood upon delivery, etc., by known methods. However, it is preferred to use the colonies of EB virus transformant obtained by infecting B cells with EB virus to perform transformation, culturing the transformant for a definite period of time, secreting antibodies having reactivity with *Pseudomonas aeruginosa* in the culture supernatant, and selecting colonies of EB virus transformed cells in which the secreted antibodies are detected or by using the cell line singly selected from these colonies of EB virus transformed cells.

Next, each step is now described in detail.

Isolation and concentration of B cells from blood or tissues described above can be efficiently carried out by the specific gravity centrifugation method using cell separation fluid such as Ficoll-Conray (Registered mark) solution, etc., the E rosette formation method, the Panning method, etc. preferably in combination. In addition, after B cells are cultured in the medium supplemented with pokeweed mitogen (PWM) for several days to grow B cells, the proliferated B cells may also be provided for the cell fusion.

Transformation of B cells with EB virus can be carried out in a manner similar to known methods [for example, Steinitz et al., Nature, 269, 420–422 (1977)]. B95-8 cells (cells derived from marmoset leucocyte derived cells capable of producing infectious EB virus) are cultured in RPMI 1640 medium containing 20% fetal calf serum (hereafter simply referred to as FCS), the RPMI 1640 medium containing FCS being sometimes simply referred to as the medium, and the culture supernatant obtained by centrifugation on Day 7 close to the stationary state is used as virus solution [Ono et al., Proceedings of the Japanese Society for Immunology, 4, 399–401 (1974)]. B cells are centrifuged and the supernatant is removed by suction. The virus solution is added to the resulting pellets to disperse the pellets followed by incubation at 37° C. for 30 minutes to an hour in the presence of 5% carbon dioxide gas. After the incubation, centrifugation is performed and the supernatant is removed by suction. Then, the medium is added to the pellets at a cell density of $1\times10^5$/ml to $5\times10^5$/ml to disperse the cells. The cell dispersion is dispensed in each well of a 24 well culture plate or a 96 well culture plate followed by incubation at 37° C. for 2 to 4 weeks in the presence of 5% carbon dioxide gas. During the period, it is preferred that half of the medium is exchanged by fresh medium at 3 or 4 day intervals.

Detection of the antibody having reactivity with *Pseudomonas aeruginosa* can be made by ordinary radioimmunoassay, enzyme-linked immunosorbent assay (hereafter simply referred to as ELISA), etc. ["MONOCLONAL ANTIBODIES", page 144, published by Kodansha Publishing Co. (1983), etc.]. In the present invention, ELISA is used. That is, the dot immunobinding assay (hereafter simply referred to as DIBA) which comprises fixing *Pseudomonas aeruginosa* previously treated with 0.3% formalin onto a membrane filter, reacting it with the cell culture supernatant in a vessel for a definite period of time, then reacting it with enzyme conjugated rabbit anti-human antibody and determining the presence or absence of the production of the desired antibody and its amount produced by coloration of the substrate by the enzyme reaction [Anal. Biochem., 119, 142–147 (1982)] is used as a handy assay method.

The well in which the desired antibody is present is selected by the ELISA described above by observing the culture supernatant of each well in which growth colonies of EB virus transformed cells are observed. Then, the cells in the well are subjected to cloning by the soft agar method ["ADVANCED TISSUE CULTURES FOR IN VITRO ASSAY AND PRODUCTION", page 289, published by Soft Science Inc. (1985), etc.] or by the limiting dilution method ["MONOCLONAL ANTIBODIES", page 73, published by Kodansha Publishing Co. (1983), etc.]. After growth of the cells is further observed by cloning, an assay is again performed by ELISA. By cloning one or more times, a single cell line capable of secreting the desired antibody alone can be obtained.

Fusion of MP 4109 and human antibody producing cells can be effected using conventional reagents for fusion such as polyethylene glycol (hereafter simply referred to as PEG) or using virus particles or virions such as Sendai virus (hemagglutinating virus of Japan: HVJ), etc. For example, RPMI 1640 medium or Dulbecco's modified Eagle's medium (DMEM) supplemented with PEG having a mean molecular weight of about 1000 to about 6000 in a concentration of 30% to 50% (W/V) is preferred as a fusing agent. Further, in order to enhance a fusion efficiency, it is preferred to supplement the fusing agent with dimethylsulfoxide (DMSO). Furthermore, physical means using an apparatus for electric fusion, etc. may be also applicable to enhancing a fusion efficiency.

For example, MP 4109 and cells in the well in which production of the desired antibody was noted after transformation with EB virus or antibody producing cells isolated from peripheral blood, etc. are mixed in a ratio of approximately 1:1 to 1:10 and a medium for cell fusion (RPMI 1640 medium containing 50% PEG and 10% DMSO, or the like) is added to the mixture to fuse the cells. Next, the cells are dispersed in a medium suited for growth of the fused hybridoma alone (hereafter simply referred to as selective medium) at a cell density of $1\times10^5$/ml to $5\times10^6$/ml. The cell dispersion is separately charged in a 24 well or 96 well culture plate followed by incubation at 37° C. for 2 to 4 weeks in the presence of 5% carbon dioxide gas. During the period, it is preferred that half of the medium is exchanged by fresh selective medium at 3 to 5 day intervals. In this case, the copresence of mouse peritoneal exudate cells, etc. as feeder cells can accelerate growth of the hybridoma. In the case that the human antibody producing cells are incapable of infinite growth (B cells), a medium containing hypoxanthine, aminoputerine and thymidine (hereafter simply referred to as HAT medium) or a medium containing hypoxanthine and azaserine (hereafter simply referred to as HA medium) can be used as the selective medium. Further, if the human antobody producing cells are cells capable of infinite growth such as EB virus transformed cells, etc., a medium obtained by adding ouabain to HAT medium (HAT-O medium) or a medium obtained by adding ouabain to HA medium (HA-O medium) can be used as the selective medium. The culture supernatant of each well in which growth colonies of the hybridoma are observed is examined, and the well in which the desired antibody is present is selected by ELISA described above followed by cloning by the limiting dilution method. After the cell growth is observed by cloning, assay is again performed by ELISA. By cloning one or more times, the single cell line capable of secreting the desired antibody alone can be obtained.

The human-human hybridoma of the present invention can be cultured in a conventional medium. For example, the human-human hybridoma is dispersed in a medium at a cell density of $5\times10^4$/ml to $2\times10^6$/ml and the dispersion is inoculated on a suitable cell culture vessel followed by culturing at 37° C. in the presence of 5% carbon dioxide gas. As the medium, basal medium such as RPMI 1640 medium, DMEM, etc. supplemented with a suitable amount of FCS is preferred. In addition, various low serum content or serum-free media can also be appropriately used. For example, NYSF 404 serum-free medium alone or NYSF 404 serum-free medium supplemented with a suitable amount of bovine serum albumin is preferred. Subculture may be performed by repeating the procedures of recovering the cells and inoculation in intervals of 3 to 7 days.

The human-human hybridoma of the present invention can be stored by freeaing in a conventional manner. For example, the cells are dispersed in a suitable storage solution for freezing at a cell density of $1\times10^5$/ml to $5\times10^7$/ml. The dispersion can be stored by freezing in liquid nitrogen or over liquid nitrogen, or in a refrigerator at −20° to −80° C. It is preferred to use the cell freeze storage solution by appropriately adding animal serum, albumin, methyl cellulose, glucose, dimethylsulfoxide, etc. to the basal medium described above or to a neutral buffer solution, etc.

The frozen cells can be thawed in a conventional manner. For example, the storage solution containing the frozen cells is rapidly thawed in warm water, the cells are washed with a medium, etc. to wash away DMSO contained in the storage solution and the cells are then dispersed in the medium followed by incubation.

The amount of immunoglobulin in the culture supernatant can be assayed by conventional ELISA. For example, in the case of using ELISA, the amount of immunoglobulin in the culture supernatant can be determined by immobilizing anti-human immunoglobulin antibody onto a solid phase (the antibody used in this case is hereafter simply referred to as fixed antibody), reacting a part of the culture supernatant with it, then reacting with enzyme conjugated anti-human immunoglobulin antibody, adding substrate to form a color in response to the enzyme reaction, and measuring the degree of coloration. Human IgM can be determined using anti-human IgM (mu chain specific) antibody as the fixed antibody and peroxidase-labeled anti-human IgM (mu chain specific) antibody as the enzyme conjugated antibody.

3. Production of human monoclonal antibody:

The human-human hybridoma of the present invention is capable of synthesizing and secreting the heavy chain derived from the antibody producing cell line and can be stably subcultured and proliferated in any ordinary medium used for the cultivation of animal cells over long periods of time. The human-human hybridoma is also capable of producing antibodies even in a serum-free medium which is free from the danger that unknown impurities derived from medium might be intermingled upon purification of the antibodies from the culture. The human-human hybridoma is thus most suited for obtaining human monoclonal antibody as the raw material for preparing compositions for preventing and treating *Pseudomonas aeruginosa* infectious diseases.

After culturing the human-human hybridoma of the present invention is serum-free medium, the resulting human monoclonal antibodies having reactivities respectively with groups A, B, E, G and I of *Pseudomonas aeruginosa* in the serologic classification by the Serotyping Comittee for the Japan *Pseudomonas aeruginosa* Society, can be relatively easily purified from the culture to a high purity by optional and conventional technique, for example, physicochemical purification such as gel filtration, ion exchange chromatography, adsorption chromatography using hydroxyapatite, etc.; affinity chromatography using a carrier to which antigen or a substance having affinity to human monoclonal antibody (e.g., protein A, anti-human immunoglobulin antibody, etc.) has been fixed, electrophoresis, precipitation such as the ammonium sulfate precipitation method, etc. individually or in combination.

4. Production of a composition comprising human monoclonal antibody:

The human monoclonal antibody of the present invention having reactivities respectively with groups A, B, E, G and I of *Pseudomonas aeruginosa* in the serologic classification by the Serotyping Comittee for the Japan *Pseudomonas aeruginosa* Society has a high protective activity against the corresponding serotype *Pseudomonas aeruginosa* infectious diseases. The human monoclonal antibody of the present invention can be provided for prophylaxis and therapy of *Pseudomonas aeruginosa* infectious diseases, by itself or in the form of a liquid or other suitable pharmaceutical composition or freeze dried preparation with additives, excipients, etc. conventionally used. In general, the additives and excipients are appropriately chosen from naturally occurring products and compounds used in biological preparations. In order to maintain stability of the antibody, animal protein such as albumin, etc., polysaccharides such as dextran, etc., amino acids and carbohydrates give good results. Furthermore, the human monoclonal antibody of the present invention may also be mixed with other monoclonal antibodies or polyclonal antibodies reactive with *Pseudomonas aeruginosa* reactive to different groups or to microorganisms other than *Pseudomonas aeruginosa* to produce multipurpose and multivalent pharmaceutical compositions.

5. Prophylaxis and therapy of infectious diseases by human monoclonal antibody:

In prophylaxis and therapy of actual *Pseudomonas aeruginosa* infectious diseases, the composition comprising the human monoclonal antibody of the present invention may be administered singly or as admixture of two or more human monoclonal antibodies. Alternatively, the composition may also be mixed with other monoclonal antibodies reactive with *Pseudomonas aeruginosa* or, with compositions comprising the same or with immune serum globulins.

The human monoclonal antibody of the present invention having reactivities with one or more groups A, B, E, G and I of *Pseudomonas aeruginosa* in the serologic classification by the Serotyping Committee for the Japan *Pseudomonas aeruginosa* Society or the composition comprising the human monoclonal antibody can be administered directly to humans for prophylaxis and therapy of *Pseudomonas aeruginosa* infectious diseases. Dosages and administration routes are appropriately chosen but a preferred dose is in the range of from 0.01 to 10 mg/body weight (kg). The administration route may be suitably chosen from intracutaneous, subcutaneous, intramuscular, intravenous and the like routes of administration.

The present invention provides a human monoclonal antibody producing cell line for industrial production which can be applied over wide fields such as prophylaxis, therapy, diagnosis and the like of *Pseudomonas aeruginosa* infectious diseases.

The present invention is further described in more detail by referring to the examples that follow but is not deemed to be limited thereto.

The parent cell line MP 4109 used for producing hybridoma has been deposited in the Fermentation Research Institute of the Agency of Industrial Science and Technology of Japan under accession No. FERM BP-2129 on Oct. 27, 1988. The human monoclonal IgM producing EB virus transformed cell line MP 5046, which is cross-reactive with groups A and F of *Pseudomonas aeruginosa*, has been deposited in the Fermentation Research Institute of the Agency of industrial Science and Technology of Japan under accession No. FERM BP-1599 on Dec. 9, 1987. The human monoclonal IgM producing EB virus transformed cell line MP 5038, which is cross-reactive with groups E and F of *Pseudomonas aeruginosa*, has been deposited in the Fermentation Research Institute of the Agency of Industrial Science and Technology of Japan under accession No. FERN BP-1596 on Dec. 7, 1987. The human monoclonal IgM producing EB virus transformed cell line MP 5050, which is cross-reactive with groups G and H of *Pseudomonas aeruginosa*, has been deposited in the Fermentation Research Institute of the Agency of Industrial Science and Technology of Japan under accession No. FERN BP-1600 on Dec. 9, 1987. The human monoclonal IgM producing EB virus transformed cell line MP 5035, which is cross-reactive with groups I and D of *Pseudomonas aeruginosa*, has been deposited in the Fermentation Research Institute of the Agency of Industrial Science and Technology of Japan under accession No. FERM BP-1598 on Dec. 9, 1987. As the standard serotype *Pseudomonas aeruginosa* in the serologic classification by the Serotyping Comittee for the Japan *Pseudomonas aeruginosa* Society, ATCC 27577 (IID 1001) was used for group A of *Pseudomonas aeruginosa*; ATCC 27578 (IID 1002), ATCC 27583 (IID 1007), ATCC 27589 (IID, 1013) and IID 5004 for group B of *Pseudomonas aeruginosa*; ATCC 27580 (IID 1004) for group D of *Pseudomonas aeruginosa*; ATCC 27581 (IID 1005) for group E of *Pseudomonas aeruginosa*; ATCC 27582 (IID 1006) for group F of *Pseudomonas aeruginosa*; ATCC 27584 (IID 1008) for group G of *Pseudomonas aeruginosa*; ATCC 27585 (IID 1009) for group H of *Pseudomonas aeruginosa*; and ATCC 27586 (IID 1010) for group I of *Pseudomonas aeruginosa*.

EXAMPLE 27

Production of a Hybridoma Capable of Producing Monoclonal Antibody to *Pseudomonas aeruginosa* (1)

(1) Cell fusion:

MP 4109 and MP 5046 were grown in RPMI 1640 medium containing 10% FCS (hereafter sometimes simply referred to as 10% FCS medium) and then collected and washed with RPMI 1640 medium, respectively. The cells of $2 \times 10^7$ each were mixed with each other in a plastic centrifuge tube of a 50 ml volume. After centrifugation (175×g, 10 minutes), the supernatant was removed by suction and, 0.5 ml of RPMI 1640 medium containing 50% PEG (M.W.: 1500, Wako Chemicals) and 10% DMSO was gently added directly to the cell pellets. While slowly rotating, the cells were fused. Two minutes after, 10 ml of RPMI 1640 medium was added to the system. After gently agitating, centrifugation (175×g, 10 minutes) followed. After the supernatant was removed by suction, RPMI 1640 medium containing 20% FCS, $2 \times 10^{-4}$M of hypoxanthine (Sigma), 1 µg/ml azaserine (Sigma) and $5 \times 10^{-6}$M of ouabain (Sigma) (hereafter sometimes simply referred to as HA-O medium) was added to the cell pellets followed by suspending at a cell density of $1 \times 10^6$/ml. Then, the suspension was inoculated on a 96 well flat bottom culture plate in 0.1 ml each per well (384 wells in total). The cells were subjected to stationary culture at 37° C. in the presence of 5% carbon dioxide gas. Four days after, 0.1 ml of HA-O medium was added and thereafter, half of the volume of HA-O medium was replaced by fresh HA-O medium at 3 to 5 day intervals. Four to five weeks after, cell growth was observed in 65 wells in total.

(2) Detection of antibody to *Pseudomonas aeruginosa*:

The presence or absence of human antibody to group A *Pseudomonas aeruginosa* in the culture supernatant was examined by the DIBA method. The culture supernatant, 0.1 ml, in each well was reacted with a nitrocellulose membrane filter (3.1 mm square; Toyo Roshi) with grid to which 0.4 µg/dot of group A *Pseudomonas aeruginosa* ATCC 27577 treated with formalin and then dried had been fixed, in a 96 well U-shaped bottom microplate. After reacting at room temperature for 2 hours, the filter was reacted with peroxidase-labeled rabbit anti-human immunoglobulin antibody (Dako Co.) for 2 hours and a color was formed using 4-chloro-1-naphthol as a substrate. When a color was observed on the nitrocellulose membrane filter by the naked eye, antibody production was judged to be positive.

(3) Cloning:

Among the culture supernatant 65 wells in which cell growth was observed, the production of human antibody to group A *Pseudomonas aeruginosa* was observed in 51 wells of the culture supernatant. From 51 wells, 18 wells containing the cells well grown were selected and the cells in the wells were collected, respectively, and accurately counted using a hemocytometer. The cells were dispersed in HA-O medium to prepare a cell suspension at a cell density of 20/ml. After the supernatant in each well of a 96 well flat bottom culture plate, on which $1 \times 10^5$/well of mouse spleen cells had previously been inoculated(hereafter simply referred to as feeder plate), was removed, the cell suspension was inoculated on the feeder plate by 0.1 ml each per well followed by stationary culture at 37° C. in the presence of 5% carbon dioxide gas. One feeder plate was used for each cell. Four days after, 0.1 ml of HA-O medium was added and then, half of the volume of HA-O medium was replaced by fresh HA-O medium at 3 to 5 day intervals. The presence or absence of human antibody to group A *Pseudomonas aeruginosa* in the culture supernatant was examined by the DIBA method in the wells in which cell growth was observed two to four weeks after. The cells in the well in which production of the antibody reactive with group A *Pseudomonas aeruginosa* was again subjected to cloning as described above. By cloning twice, 12 strains of hybridomas from MP 5120 to MP 5131 producing the human monoclonal antibody capable of cross-reacting with groups A and F *Pseudomonas aeruginosa* in the serologic classification by the Serotyping Comittee for the Japan *Pseudomonas aeruginosa* Society were obtained.

MP 5121 was deposited in the Fermentation Research Institute of the Agency of Industrial Science and Technology of Japan under accession No. FERM BP-2270.

The hybridomas sufficiently grown in the 96 well flat bottom culture plate were cultured gradually on a large scale. After the cells were suspended in a cell storage solution composed of 15% RPMI 1640 medium, 75% FCS and 10% DMSO at a density of $1\times10^6$/ml, the suspension was separately charged in a 2 ml freezing tube. After cooling it to $-20°$ C. at a rate of $1°$ C./min, the tube was stored freezingly in liquid nitrogen.

(4) Determination of amount of antibody produced:

The amount of IgM which the hybridomas secreted outside the cells was determined as follows. The cells in the logarithmic phase were collected and suspended in 10% FCS medium at a density of $1\times10^6$/ml, and 1 ml each of the suspension was inoculated on each well of a 6 well culture plate followed by stationary culture at $37°$ C. in the presence of 5% carbon dioxide gas. Twenty four hours after, the culture supernatant was separated by centrifugation ($250\times$g, 10 minutes) and an amount of IgM in the supernatant was quantitatively determined by ELISA. In the 12 hybridomas, 10 cells secreted 6 to 56 µg of human IgM to the culture supernatant for 24 hours.

(5) Determination of stability of the cell line in continuous subculture:

Stability of the cell line in continuous subculture was examined in terms of cell growth efficiency and antibody productivity.

Stability of the grown was determined by measuring growth curves of the cells at the time of initiating culture and 3 months after the initiation of continuous subculture. Stability of antibody production was examined by measuring amounts of IgM antibody produced at the time when the culture started, and one month, 2 months and 3 months after the initiation of culture by ELISA as in (4) above.

Continuous subculture was carried out as follows. The cells were independently suspended in duplicate in 10% FCS medium at a cell density of $5\times10^4$/ml. Then 4 ml of each suspension was inoculated on a cell culture flask having a bottom area of 25 cm² followed by stationary culture at $37°$ C. in the presence of 5% carbon dioxide gas. The cells were collected at 3 or 4 day intervals and again suspended in fresh 10% FCS medium at the same density followed by stationary culture. The procedure was carried out continuously for 3 months.

Growth curve was measured as follows. The cells in the logarithmic phase which had been independently cultured in duplicate were collected and suspended at a density of $5\times10^4$/ml in 10% FCS medium. Then 1 ml of the suspension was inoculated on each well of a 6 well culture plate (6 wells in total) followed by stationary culture at $37°$ C. in the presence of 5% carbon dioxide gas. The culture in one well was collected every day to count viable cell and dead cell densities. The amount of IgM in the culture supernatant was determined by ELISA.

MP 5121 showed almost the same growth curve with the cells at the beginning of cultivation and 3 months after the cultivation. The doubling time calculated from the growth curve was 25.5 hours. Furthermore, IgM secreted by 10 cells for 24 hours was 56 µg at the beginning of cultivation, 40 µg one month after the initiation of cultivation, 45 µg 2 months after and 42 µg 3 months after, indicating that there was no significant difference in the amount of antibody produced during continuous subculture for 3 months.

EXAMPLE 28

Cell Culture and Purification of the Antibody (1)

The frozen cells of MP 5121 were thawed and cultured in 10% FCS medium on a large scale. After culturing the cells in NYSF 404 medium [Noritsugu Yabe, TISSUE CULTURE, 11, 458 (1985)] on a larger scale, the cells were collected and suspended in 500 ml of NYSF 404 medium at a cell density of $5\times10^4$/ml. The cells were then inoculated on 10 flasks (bottom area of 175 cm²) followed by stationary culture at $37°$ C. for 5 days in the presence of 5% carbon dioxide gas. From the culture, 480 ml of the supernatant was obtained by centrifugation ($400\times$g, 20 minutes) and filtered through a membrane filter having a pore size of 0.22 micron.

After 480 ml of saturated ammonium sulfate aqueous solution was added to the filtrate, the mixture was allowed to stand at $4°$ C. The next day, the mixture was centrifuged ($10,000\times$g, 30 minutes) and the precipitates were collected. The precipitates were dissolved in 5 ml of PBS(-) and sufficiently dialyzed against PBS(-) to give the crude IgM fraction.

For purification, a hydroxyapatite-packed column for high performance liquid chromatography was used and fractionation was carried out at a flow rate of 1 ml/min. HCA-Column (guard column; 4 mm$\times$10 mm, body column: 7.6 mm$\times$100 mm, Mitsui Toatsu Chemical Co., Ltd.) was previously equilibrated with 0.01M sodium phosphate buffer (pH 7.0) containing 0.15M sodium chloride (hereafter simply referred to as Solution A) and 2 ml of the crude IgM fraction was added thereto. The column was washed with Solution A for 10 minutes and further with a solution obtained by adding Solution A to 0.25M sodium phosphate buffer (pH 7.5 ,hereafter simply referred to as Solution B) in 75:25 by volume for 15 minutes. Thereafter, linear density gradient elution of 25% to 100% in the ratio of Solution B was performed over 20 minutes. The IgM fraction eluted as the single peak was thoroughly dialyzed against PBS(-). From 480 ml of the culture supernatant, the solution containing 12.3 mg of IgM (N4-2) was obtained.

EXAMPLE 29

Production of Hybridoma Capable of Producing Monoclonal Antibody to *Pseudomonas aeruginosa* (2)

(1) preparation of EB virus solution:

B95-8 cells which produced and released EB virus were dispersed in RPMI 1640 medium containing 20% FCS (hereafter sometimes simply referred to as 20% FCS medium) at a cell density of $3\times10^5$/ml followed by stationary culture at $37°$ C. in the presence of 5% carbon dioxide gas. The culture supernatant on Day 7 close to the stationary state were collected by centrifugation ($800\times$g, 10 minutes) and filtered through a membrane filter (Millipore) having a pore size of 0.45 micron to give EB virus solution.

(2) Preparation of human lymphocyte:

From healthy donor whose serum antibody activity to group A *Pseudomonas aeruginosa* was detected up to 1000-fold dilution by the DIBA method, 50 ml of heparinized peripheral blood was collected. An equal volume of RPMI 1640 medium was added to the blood to dilute it 2-fold. The dilution was overlaid on the half volume of Ficoll-Paque (Pharmacia) not to ruffle the interface, followed by centrifugation (400×g, 30 minutes) at room temperature. After centrifugation, the interface was withdrawn using a Pasteur pipette and an equal volume of 20% FCS medium was added thereto followed by centrifugation (250×g, 10 minutes) at room temperature. After the precipitated cells were suspended in 20% FCS medium, centrifugation was further repeated to give human lymphocyte pellets (cell number: $4 \times 10^7$).

(3) Transformation with EB virus:

To $4 \times 10^7$ of human antibody producing cells was added 40 ml of the virus solution prepared in (1) followed by incubation at 37° C. for an hour. After the incubation, the cells were collected by centrifugation (250×g, 10 minutes). The cells were dispersed in 20% FCS medium. After the dispersion was adjusted to a cell density of $5 \times 10^5$/ml, 0.1 ml each of the dispersion was inoculated on a 96 well flat bottom culture plate followed by stationary culture at 37° C. in the presence of 5% carbon dioxide gas. Four days after, 0.1 ml of 20% FCS medium was added and half of the volume of the medium was replaced by a fresh medium at 3 to 5 day intervals. With respect to the wells where cell growth was observed, the presence or absence of human antibody to group A *Pseudomonas aeruginosa* in the culture supernatant was examined by the DIBA method in a manner similar to Example 27, (2). The cells in the wells in which antibody production was detected were cultured in a 24 well culture plate on an enlarged scale.

(4) Cloning:

The cells in the wells in which production of human antibody to group A *Pseudomonas aeruginosa* antibody was detected by the antibody detection method were transferred to a Petri dish of 6 cm in diameter. The cells grown in the Petri dish were frozen and then stored in liquid nitrogen as in Example (3). The frozen tube containing the cells was withdrawn from liquid nitrogen and thawed while stirring in a warm bath at 37° C. The cells were then suspended in 10 ml of 20% FCS medium. The cells were collected by centrifugation (250×g, 10 minutes) and dispersed in 2 ml of 20% FCS medium. The dispersion was inoculated on a Petri dish of 6 cm in diameter followed by stationary culture at 37° C. for 3 days in the presence of 5% carbon dioxide gas. The grown cells were subjected to cloning once by the soft agar method. Firstly, after the cell number was accurately counted with a hemocytometer, a cell suspension at a cell density of $1 \times 10^6$/ml was prepared. To 30 ml of medium containing 0.3% agarose (SeaPlaque Agarose (Registered mark), FMC) was added 0.1 ml of this cell suspension for mixing. Next, 3 ml of a medium containing the cells and 0.3% agarose were separately charged and fixed in a Petri dish of 6 cm which had been separately charged and fixed with 4 ml of medium containing 0.5% agarose (10 plates per each cell). The 6 cm Petri dish separately charged and fixed the cells were subjected to stationary culture at 37° C. in the presence of 5% carbon dioxide gas. Three to five weeks after, the cells grew on soft agar and colonies were observed with the naked eye. Then, each colony was transferred to each well of a 96 well flat bottom culture plate, which had been previously charged separately with 0.1 ml of 20% FCS medium, using a Pasteur pipette. Two days after, 0.1 ml of 20% FCS medium was further added thereto and an additional 2 days after, with respect to the wells where cell growth was observed, the presence or absence of human monoclonal antibody to *Pseudomonas aeruginosa* in the culture supernatant was examined by the DIBA method. The cells in the wells in which antibody production was judged to be positive was cultured in a 24 well culture plate on an enlarged scale. Three days after, with respect to the wells of the 24 well culture plate, the presence or absence of human antibody to *Pseudomonas aeruginosa* in the culture supernatant was examined by the DIBA method. Among them, the cells in the wells in which the activity of human antibody to *Pseudomonas aeruginosa* was high in the culture supernatant were cultured in order on an enlarged scale to give EB virus transformed cell colony §965N5 capable of producing human IgM antibody to group A *Pseudomonas aeruginosa*.

(5) cell fusion:

Using $2 \times 10^7$ of EB virus transformed cell colony §965N5 capable of producing human IgM antibody to group A *Pseudomonas aeruginosa* and MP 4109, respectively, cell fusion was performed in a manner similar to Example 27, (1). The fused cells were suspended in HA-O medium at a cell density of $1 \times 10^6$/ml and the suspension was inoculated on a 96 well flat bottom culture plate in 0.1 ml each per well (384 wells in total). The cells were subjected to stationary culture at 37° C. in the presence of 5% carbon dioxide gas. Four days after, 0.1 ml of HA-O medium was added thereto and thereafter, half of the volume of HA-O medium was replaced by fresh HA-O medium at 4 or 5 day intervals. With respect to 35 wells in which the antibody to group A *Pseudomonas aeruginosa* in the cells grew, the presence or absence of human culture supernatant was examined by the DIBA method in a manner similar to Example 27, (2). The antibody production was detected in the culture supernatant of 2 wells of 1B5 and 3G12. The cells in the 2 wells were cloned in a manner similar to Example 27, (3), respectively, to give hybridoma MP 5136 capable of producing human monoclonal antibody reactive only with group A *Pseudomonas aeruginosa*.

MP 5136 was deposited in the Fermentation Research Institute of the Agency of Industrial Science and Technology of Japan under accession No. FERM BP-2271.

(6) Determination of amount of antibody produced:

The amount of antibody produced by MP 5136 was determined in a manner similar to Example 27, (4).

As the result, in hybridoma MP 5136, $10^6$ cells secreted 13 μg of human IgM in the culture supernatant for 24 hours.

(7) Determination of stability of cell line in continuous subculture:

The growth ability and the stability of amount of antibody production of MP 5136 cell line were determined in a manner similar to Example 27, (5).

MP 5136 showed almost the same growth curve with the cells at the beginning of cultivation and 3 months after the cultivation. The doubling time calculated from the growth curve was 27 hours. Furthermore, IgM secreted by 10 cells for 24 hours was 13 μg at the beginning of cultivation, 14 μg one month after the initiation of cultivation, 8 μg 2 months after and 12 μg 3 months after, indicating that there was no significant difference in the amount of antibody produced during continuous subculture for 3 months.

EXAMPLE 30

Cell Culture and Purification of Antibody (2)

The frozen cells of MP 5136 were thawed and cultured in 10% FCS medium on a large scale. After culturing the cells in NYSF 404 medium on a larger scale, the cells were suspended in 50 ml of NYSF 404 medium at a cell density of $5 \times 10^4$/ml. The cells were then inoculated on 1 flask (bottom area of 175 cm$^2$) followed by stationary culture at 37° C. for 5 days in the presence of 5% carbon dioxide gas.

The cells were collected and suspended in 500 ml of NYSF 404 medium at a cell density of $5\times10^4$/ml. The suspension was then inoculated on one starring culture flask (Techne) followed by spinner culture at 37° C. for 5 days at 20 rpm in the presence of 5% carbon dioxide gas. From 485 ml of the culture, 480 ml of the supernatant was obtained by centrifugation (400×g, 20 minutes) and filtered through a membrane filter having a pore size of 0.22 micron.

The antibody was purified from the filtrate in a manner similar to Example 28. From 480 ml of the culture supernatant, the solution containing 10.5 mg of IgM (N10-1) was obtained.

EXAMPLE 31

Production of Hybridoma Capable of Producing Antibody to *Pseudomonas aeruginosa* (3)

(1) Preparation of EB virus solution:

EB virus solution was prepared in a manner similar to Example 29, (1).

(2) Preparation of human lymphocyte:

Heparinized peripheral blood, 50 ml, collected from healthy donors whose serum antibody activity to group B *Pseudomonas aeruginosa* was detected up to 1000-fold dilution by the DIBA method was used. Human lymphocytes were prepared in a manner similar to Example 29, (2) to give human lymphocyte pellets (cell number, $3.5\times10^7$).

(3) Transformation with EB virus:

Transformation with EB virus was performed in a manner similar to Example 29, (3), using $3.5\times10^7$ of the human antibody producing cells prepared in (2) and 35 ml of the virus solution prepared in (1). The transformant was inoculated on 672 wells in total. Three weeks after, cell growth was noted in all of the wells.

(4) Detection of antibody to *Pseudomonas aeruginosa*:

Group B serotype *Pseudomonas aeruginosa* ATCC 27578 was used as the formalinized dry bacteria. Anti-*Pseudomonas aeruginosa* human antibody was detected in a manner similar to Example 27, (2).

(5) Cloning:

The cells in the 64 wells in which production of anti-group B *Pseudomonas aeruginosa* antibody was detected by the antibody detection method were transferred to a 24 well culture plate, a 6 well culture plate and a Petri dish of 6 cm in diameter, in this order, on an enlarged scale. With respect to the Petri dish in which cell growth was observed, the presence or absence of antibody to group B *Pseudomonas aeruginosa* in the culture supernatant was examined by the DIBA method in a manner similar to (4). Cloning was performed by the procedures similar to Example 29, (4), except for using the cells in the 16 Petri dishes showing a potent activity out of 52 dishes in which antibody production was detected. Three to five weeks after, the cells grew on soft agar and colonies were observed with the naked eye. Then, each colony was transferred to each well of a 96 well flat bottom culture plate, which had been previously charged separately with 0.1 ml of 20% FCS medium, using a Pasteur pipette. Two days after, 0.1 ml of 20% FCS medium was further added thereto and an additional 2 days thereafter, with respect to the wells where cell growth was observed, the presence or absence of human antibody to *Pseudomonas aeruginosa* in the culture supernatant was examined by the DIBA method. Antibody production was detected in soft agar colonies derived from 2 Petri dishes of 6 cm in diameter. These colonies were cultured sequentially on an enlarged scale to give EB virus transformed cell colonies 6L10N1, 6L10N2, 6L10N3 and 6L10N4 capable of producing human IgM antibody to group B *Pseudomonas aeruginosa*.

(6) Cell fusion:

Using $3\times10^7$ cells of EB virus transformed cell colony 6L10N2 capable of producing human IgM antibody to group B *Pseudomonas aeruginosa* and MP 4109, respectively, cell fusion was performed in a manner similar to Example 27, (1).

The fused cells were suspended in HA-O medium. After adjusting to a cell density of $5\times10^6$/ml, 0.1 ml each per well was inoculated on a 96 well flat bottom culture plate (192 wells in total). The cells were subjected to stationary culture at 37° C. in the presence of 5% carbon dioxide gas. Four days after, 0.1 ml of HA-O medium was added thereto and thereafter, half of the volume of HA-O medium was replaced by fresh HA-O medium at 3 to 5 day intervals. Four or 5 weeks after, cell growth was observed in 26 wells in total.

(7) cloning:

The production of human antibody to group B *Pseudomonas aeruginosa* was detected in the culture supernatant of 20 wells among the culture supernatant of 26 wells in which cell growth was observed The cells of the 20 wells were cloned in a manner similar to Example 27, (3). Two to four weeks after, with respect to the wells where-cell growth was observed, the presence or absence of human antibody to group B *Pseudomonas aeruginosa* in the culture supernatant was examined by the DIBA method. The cells of the wells in which production of antibody reactive with group B *Pseudomonas aeruginosa* was detected were again cloned in a manner similar to Example 27, (3). By cloning twice, 10 strains of MP hybridomas from MP 5090 to 5098 and MP 5147 capable of producing human monoclonal antibody reactive with group B *Pseudomonas aeruginosa* (ATCC 27588, ATCC 27583, ATCC 27589, IID 5004) were obtained.

MP 5097 was deposited in the Fermentation Research Institute of the Agency of Industrial Science and Technology of Japan under accession No. FERM BP-2268.

The hybridomas sufficiently grown in the 96 well flat bottom culture plate were cultured gradually on a larger scale. After the cells were suspended in a cell storage solution composed of 75% FCS, 10% DMSO and 15% RPMI 1640 medium at a density of $1\times10^6$/ml, the suspension was separately charged in a 2 ml freezing tube. After cooling it to −20° C. at a rate of 1° C./min, the tube was stored freezingly in liquid nitrogen.

(8) Determination of the amount of antibody produced:

The amount of antibody produced by 10 strains from MP 5090 to MP 5098 and MP 5147 was measured in a manner similar to Example 27, (4).

In the 10 hybridomas, 106 cells secreted 8 to 38 μg of human IgM to the culture supernatant for 24 hours.

(9) Determination of stability of cell line in continuous subculture:

Stability of the growth and antibody production of MP 5093, MP 5095 and MP 5097 were examined in a manner similar to Example 27, (5).

Each of the three cell lines showed almost the same growth curve with the cells at the beginning of cultivation and 3 months after the cultivation. The doubling times of MP 5093, MP 5095 and MP 5097 calculated from the growth curves were 25.5, 25 and 25.5 hours, respectively. IgM secreted by 10 cells for 24 hours was reduced in MP 5093 and MP 5095 during continuous subculture over 3 months. However, in MP 5097, IgM secreted by 10 cells for 24 hours was 20 μg at the beginning of cultivation, 22 μg two months after and 15 μg 3 months after, indicating that there was no significant difference in the amount of antibody produced during continuous subculture for 3 months.

EXAMPLE 32

Cell Culture and Purification of Antibody (3)

The frozen cells of MP 5097 were thawed and cultured in 10% FCS medium on a large scale. After culturing the cells in NYSF 404 medium on a larger scale, the cells were suspended in 500 ml of NYSF 404 medium at a cell density of $5 \times 10^4$/ml. The suspension was then inoculated on ten flasks (bottom area of 175 cm$^2$) followed by stationary culture at 37° C. for 5 days in the presence of 5% carbon dioxide gas. From the culture, 480 ml of the supernatant was obtained by centrifugation (400×g, 20 minutes) and filtered through a membrane filter having a pore size of 0.22 micron.

The antibody was purified from the filtrate in a manner similar to Example 28. From 480 ml of the culture supernatant, the solution containing 12.1 mg of IgM (N3-8) was obtained.

EXAMPLE 33

4. Production of Hybridoma Capable of Producing Monoclonal Antibody to *Pseudomonas aeruginosa* (4)

(1) Cell fusion:

Using $3 \times 10^7$ of MP 4109 and MP 5038, respectively, cell fusion was carried out in a manner similar to Example 27, (1).

After the fused cells were suspended in HA-O medium at a cell density of $1 \times 10^6$/ml, the suspension was inoculated on a 96 well flat bottom culture plate in 0.1 ml each per well (576 wells in total). The cells were subjected to stationary culture at 37° C. in the presence of 5% carbon dioxide gas. Four days after, 0.1 ml of HA-O medium was added thereto and thereafter, half of the volume of HA-O medium was replaced by fresh HA-O medium at 3 to 5 day intervals. Four to five weeks after, cell growth was observed in 3 wells in total of 1E5, 3E2 and 4A11.

Using $5 \times 10^6$ of MP 4109 and MP 5038, respectively, cell fusion was carried out as described above. After the fused cells were suspended in RPMI 1640 medium containing 20% FCS, $2 \times 10^{-4}$M of hypoxanthine, 0.66 μg/ml azaserine and $6 \times 10^{-7}$M of ouabain at a cell density of $1 \times 10^6$/ml, the suspension was inoculated on a 96 well flat bottom culture plate in 0.1 ml each per well (96 wells in total). The cells were subjected to stationary culture at 37° C. in the presence of 5% carbon dioxide gas. Four days after, 0.1 ml of RPMI 1640 medium containing 20% FCS, $2 \times 10^{-4}$M of hypoxanthine, 0.33 μg/ml azaserine and $3 \times 10^{-7}$M of ouabain (modified HA-O medium) was added thereto and thereafter, half of the volume of HA-O medium was replaced by fresh HA-O medium at 3 to 5 day intervals for the following 2 weeks. After two weeks passed, the medium was exchanged by RPMI 1640 medium containing 20% FCS and $2 \times 10^{-4}$M of hypoxanthine. Four to five weeks after, cell growth was observed in 4 wells in total of 5A10, 5C3, 5C8 and 5G5.

(2) Detection of antibody to *Pseudomonas aeruginosa*:

Group E *Pseudomonas aeruginosa* ATCC 27581 was used as the formalinized dry bacteria. Anti-*Pseudomonas aeruginosa* antibody was detected in a manner similar to Example 27, (2).

(3) Cloning:

Among the culture supernatant of 7 wells in which cell growth was observed, the production of human antibody to group E *Pseudomonas aeruginosa* was detected in the culture supernatant of 5 wells of 1E5, 3E2, 14A11, 5C3 and 5G5. The cells of the 5 wells were cloned in a manner similar to Example 27, (3). Two to four weeks after, with respect to the wells where cell growth was observed, the presence or absence of human antibody to group E *Pseudomonas aeruginosa* in the culture supernatant was examined by the DIBA method. The cells of the wells in which production of antibody reactive with group E *Pseudomonas aeruginosa* was detected were again cloned in a manner similar to Example 27, (3). By cloning twice, 5 strains of hybridomas MP 5133, MP 5135, MP 5137, MP 5138 and MP 5139 capable of producing human monoclonal antibody which is cross-reactive with groups E and F *Pseudomonas aeruginosa* in the serologic classification by the Serotyping Comittee for the Japan *Pseudomonas aeruginosa* Society were obtained.

MP 5139 was deposited in the Fermentation Research Institute of the Agency of Industrial Science and Technology of Japan under accession No. FERM BP-2272.

The hybridomas sufficiently grown in a 96 well flat bottom culture plate were cultured gradually on a larger scale. After the cells were suspended in a cell storage solution composed of 75% FCS, 10% DMSO and 15% RPMI 1640 medium at a density of $1 \times 10^6$/ml, the suspension was separately charged in a 2 ml freezing tube. After cooling it to −20° C. at a rate of 1° C./min, the tube was stored freezingly in liquid nitrogen.

(4) Determination of amount of antibody produced:

The amount of antibody produced by 5 strains of MP 5133, MP 5135, MP 5137, MP 5138 and MP 5139 was measured in a manner similar to Example 27, (4).

In hybridomas of MP 5133, MP 5135, MP 5137, MP 5138 and MP 5139, 10 cells secreted 18 μg, 30 μg, 44 μg, 7 μg, and 45 μg of human IgM to the culture supernatant for 24 hours.

(5) Determination of stability of cell line in continuous subculture:

Stability of the growth and antibody production of MP 5139 were examined in a manner similar to Example 27, (5).

MP 5139 showed almost the same growth curve with the cells at the beginning of cultivation and 3 months after the cultivation, The doubling time calculated from the growth curve was 26 hours. Furthermore, IgM secreted by 10 cells for 24 hours was 45 μg at the beginning of cultivation, 40 μg one month after the initiation of cultivation, 38 μg 2 months after and 36 μg 3 months after, indicating that there was no significant difference in the amount of antibody produced during continuous subculture for 3 months.

EXAMPLE 34

Cell Culture and Purification of antibody (4)

The frozen cells of MP 5139 were thawed and cultured in 10% FCS medium on a large scale. After culturing the cells in NYSF 404 medium on a larger scale, the cells were suspended in 500 ml of NYSF 404 medium at a cell density of $5 \times 10^4$/ml. The suspension was then inoculated on ten flasks (bottom area of 175 cm$^2$) followed by stationary culture at 37° C. for 5 days in the presence of 5% carbon dioxide gas. From the culture, 480 ml of the supernatant was obtained by centrifugation (400×g, 20 minutes) and filtered through a membrane filter having a pore size of 0.22 micron.

The antibody was purified from the filtrate in a manner similar to Example 28. From 480 ml of the culture supernatant, the solution containing 10.6 mg of IgM (N1-5) was obtained.

EXAMPLE 35

Production of Hybridoma Capable of Producing Monoclonal Antibody to *Pseudomonas aeruginosa* (5)

(1) Preparation of EB virus solution:

EB virus solution was prepared in a manner similar to Example 29, (1).

(2) Preparation of human lymphocyte:

Heparinized peripheral blood, 50 ml, collected from healthy donor whose serum antibody activity to group E *Pseudomonas aeruginosa* was detected up to 1000-fold dilution by the DIBA method was used. Human lymphocytes were prepared in a manner similar to Example 29, (2) to give human lymphocyte pellets (cell number, $5 \times 10^7$).

(3) Transformation with EB virus:

Transformation with EB virus was performed in a manner similar to Example 29, (3), using $5 \times 10^7$ of the human antibody producing cells prepared in (2) and 50 ml of the virus solution prepared in (1). With respect to the wells in which cell growth was observed, the presence or absence of antibody to group E *Pseudomonas aeruginosa* in the culture supernatant was examined in a manner similar to Example 27, (2). The cells in the well in which antibody production was judged to be positive were cultured in a 24 well culture plate on a large scale.

(4) Cloning:

The cells in the wells in which production of human monoclonal antibody to group E *Pseudomonas aeruginosa* antibody was detected by the antibody detection method were transferred to a Petri dish of 6 cm in diameter. The cells grown in the Petri dish were cloned in a manner similar to Example 29, (4). Three to five weeks after, the cells grew on soft agar and colonies were observed with the naked eye. Then, each colony was transferred to each well of a 96 well flat bottom culture plate, which had been previously charged separately with 0.1 ml of 20% FCS medium, using a Pasteur pipette. Two days after, 0.1 ml of 20% FCS medium was also added and an additional 2 days after, with respect to the wells where cell growth was observed, the presence or absence of human antibody to *Pseudomonas aeruginosa* in the culture supernatant was examined by the DIBA method. The cells in the wells where antibody production was judged to be positive were cultured in a 24 well culture plate on an enlarged scale. Three days after, with respect to the wells in the 24 well culture plate, the presence or absence of human antibody to *Pseudomonas aeruginosa* in the culture supernatant was examined by the DIBA method. Among them, the cells in the wells in which the activity of human antibody to *Pseudomonas aeruginosa* was high in the culture supernatant were cultured in order on an enlarged scale to give EB virus transformed cell colony 86Z26AN6 capable of producing human IgM antibody to group E *Pseudomonas aeruginosa*.

(5) Cell fusion:

Using $2.5 \times 10^7$ each of EB virus transformed cell colony 86Z26AN6 capable of producing human IgM antibody to group E *Pseudomonas aeruginosa* and MP 4109, cell fusion was carried out in a manner similar to Example 27, (1). The fused cells were suspended in HA-O medium to adjust to a cell density of $1 \times 10^6$/ml, and 0.1 ml each per well was inoculated on a 96 well flat bottom culture plate (480 wells in total). The cells were subjected to stationary culture at 37° C. in the presence of 5% carbon dioxide gas. Four days after, 0.1 ml of HA-O medium was added thereto and thereafter, half of the volume of HA-O medium was replaced by fresh HA-O medium at 4 or 5 day intervals. With respect to the 21 wells where cell grew, the presence or absence of human antibody to *Pseudomonas aeruginosa* in the culture supernatant was determined by the DIBA method. The antibody activity was detected in four wells of 1F2, 3A6, 3H11 and 4B4. And they were cloned, 3 strains of hybridomas MP 5140, MP 5141 and MP 5143 capable of producing human monoclonal antibody reactive only with group E *Pseudomonas aeruginosa* were obtained.

MP 5140 was deposited in the Fermentation Research Institute of the Agency of Industrial Science and Technology of Japan under accession No. FERM BP-2273.

(6) Determination of amount of antibody produced:

The amount of antibody produced by 3 strains of MP 5140, MP 5141 and MP 5143 was measured in a manner similar to Example 27, (4).

In hybridomas of MP 5140, MP 5141 and MP 5143, $10^6$ cells secreted 54 µg, 53 µg and 13 µg of human IgM in the culture supernatant for 24 hours, respectively.

(7) Determination of stability of cell line in continuous subculture:

Stability of the growth and antibody production of MP 5140 were examined in a manner similar to Example 27, (5).

MP 5140 showed almost the same growth curve with the cells at the beginning of cultivation and 3 months after the cultivation. The doubling time calculated from the growth curve was 24.5 hours. IgM secreted by 10 cells for 24 hours was 54 µg at the beginning of cultivation, 45 µg one month after, 40 µg two months after and 38 µg three months after, indicating that there was no significant difference in the amount of antibody produced during continuous subculture for 3 months.

EXAMPLE 36

Cell Culture and Purification of Antibody

The frozen cells of MP 5140 were thawed and cultured in 10% FCS medium on a large scale. After culturing the cells in NYSF 404 medium on a larger scale, the cells were suspended in 50 ml of NYSF 404 medium at a cell density of $5 \times 10^4$/ml. The cells were then inoculated on 1 flask (bottom area of 175 cm$^2$) followed by stationary culture at 37° C. for 5 days in the presence of 5% carbon dioxide gas. The cells were collected and suspended in 500 ml of NYSF 404 medium at a cell density of $5 \times 10^4$/ml. The suspension was then inoculated on one starring culture flask (Techne) followed by spinner culture at 37° C. for 5 days at 20 rpm in the presence of 5% carbon dioxide gas. From 485 ml of the culture, 480 ml of the supernatant was obtained by centrifugation (400×g, 20 minutes) and filtered through a membrane filter having a pore size of 0.22 micron.

The antibody was purified from the filtrate in a manner similar to Example 28. From 480 ml of the culture supernatant, the solution containing. 13.2 of IgM (N11-1) was obtained.

EXAMPLE 37

Production of Hybridoma Capable of Producing Monoclonal Antibody to *Pseudomonas aeruginosa* (6)

(1) Cell fusion:

Using $1.5\times10^7$ of MP 4109 and MP 5050, respectively, cell fusion was carried out in a manner similar to Example 27, (1).

After the fused cells were suspended in HA-O medium at a cell density of $1\times10^6$/ml, the suspension was inoculated on a 96 well flat bottom culture plate in 0.1 ml each per well (288 wells in total). The cells were subjected to stationary culture at 37° C. in the presence of 5% carbon dioxide gas. Four days after, 0.1 ml of HA-O medium was added thereto and thereafter, half of the volume of HA-O medium was replaced by fresh HA-O medium at 3 to 5 day intervals. Four to five weeks after, cell growth was observed in 10 wells in total.

(2) Detection of antibody to *Pseudomonas aeruginosa*:

As the formalinized dry bacteria, group G *Pseudomonas aeruginosa* ATCC 27584 was used. Anti-*Pseudomonas aeruginosa* human antibody was detected in a manner similar to Example 27,(2).

(3) Cloning:

Among the culture supernatant of the 10 wells in which cell growth was observed, the production of human antibody to group G *Pseudomonas aeruginosa* was detected in the culture supernatant of 8 wells. The cells of the 8 wells were cloned in a manner similar to Example 27, (3). Two to four weeks after, with respect to the wells where cell growth was observed, the presence or absence of human antibody to group G *Pseudomonas aeruginosa* in the culture supernatant was examined by the DIBA method. The cells of the wells in which production of antibody reactive with group G *Pseudomonas aeruginosa* was detected were again cloned in a manner similar to Example 27,(3). By cloning twice, 2 strains of hybridomas MP 5142 and MP 5151 capable of producing human monoclonal antibody which is cross-reactive with groups G and H *Pseudomonas aeruginosa* in the serologic classification by the Serotyping Comittee for the Japan *Pseudomonas aeruginosa* Society were obtained.

MP 5151 was deposited in the Fermentation Research Institute of the Agency of Industrial Science and Technology of Japan under accession No. FERM BP-2274.

The hybridomas sufficiently grown in a 96 well flat bottom culture plate were cultured gradually on a larger scale. After the cells were suspended in a cell storing solution composed of 75% FCS, 10% DMSO and 15% RPMI 1640 medium at a density of $1\times10^6$/ml, the suspension was separately charged in a 2 ml freezing tube. After cooling to −20° C. at a rate of 1° C./min, the tube was stored freezingly in liquid nitrogen.

(4) Determination of amount of antibody produced:

The amount of antibody produced by 2 strains of MP 5142 and MP 5151 was measured in a manner similar to Example 27, (4).

In hybridomas of MP 5142 and MP 5151, $10^6$ cells secreted 16 μg and 18 μg of human IgM in the culture supernatant for 24 hours, respectively.

(5) Determination of stability of cell line in continuous subculture:

Stability of the growth and antibody production of MP 5151 were examined in a manner similar to Example 27, (5).

MP 5151 showed almost the same growth curve with the cells at the beginning of cultivation and 3 months after the cultivation. The doubling time calculated from the growth curve was 23.5 hours. Furthermore, IgM secreted by $10^6$ cells for 24 hours was 18 μg at the beginning of cultivation, 15 μg one month after the initiation of cultivation, 15 μg 2 months after and 13 μg 3 months after, indicating that there was no significant difference in the amount of antibody produced during continuous subculture for 3 months.

EXAMPLE 38

Cell Culture and Purification of Antibody (6)

The frozen cells of MP 5151 were thawed and cultured in 10% FCS medium on a large scale. After culturing the cells in NYSF 404 medium on a larger scale, the cells were suspended in 500 ml of NYSF 404 medium at a cell density of $5\times10^4$/ml. The suspension was then inoculated on ten flasks (bottom area of 175 cm$^2$) followed by stationary culture at 37° C. for 5 days in the presence of 5% carbon dioxide gas. From the culture, 480 ml of the supernatant was obtained by centrifugation (400×g, 20 minutes) and filtered through a membrane filter having a pore size of 0.22 micron.

The antibody was purified from the filtrate in a manner similar to Example 28. From 480 ml of the culture supernatant, the solution containing 13.7 mg of IgM (N7-2) was obtained.

EXAMPLE 39

Production of Hybridoma Capable of Producing Monoclonal Antibody to *Pseudomonas aeruginosa* (7)

(1) Preparation of EB virus solution:

EB virus solution was prepared in a manner similar to Example 29, (1).

(2) Preparation of human lymphocyte:

Heparinized peripheral blood, 50 ml, collected from healthy donor whose serum antibody activity to group G *Pseudomonas aeruginosa* was detected up to 1000-fold dilution by the DIBA method was used. Human lymphocytes were prepared in a manner similar to Example 29, (2) to give human lymphocyte pellets (cell number, $4.8\times10^7$).

(3) Transformation with EB virus:

Transformation with EB virus was performed in a manner similar to Example 29, (3), using $4.8\times10^7$ of the human antibody producing cells prepared in (2) and 48 ml of the virus solution prepared in (1). The cells in the well in which antibody production was judged to be positive were cultured in a 24 well culture plate on a large scale.

(4) Cloning:

The cells in the wells in which production of human antibody to Group G *Pseudomonas aeruginosa* antibody was detected by the antibody detection method were transferred to a Petri dish of 6 cm in diameter. The cells grown in the 6 cm Petri dish were cloned in a manner similar to Example 29, (4). Three to five weeks after, the cells grew on soft agar and colonies were observed with the naked eye. Then, each colony was transferred to each well of a 96 well flat bottom culture plate, which had been previously charged separately with 0.1 ml of 20% FCS medium, using a Pasteur pipette followed by stationary culture. Two days after, 0.1 ml of 20% FCS medium was further added thereto and an additional 2 days after, with respect to the wells where cell growth was observed, the presence or absence of human antibody to *Pseudomonas aeruginosa* in the culture supernatant was examined by the DIBA method. The cells in the wells wherein antibody production was judged to be positive were cultured in a 24 well culture plate on an enlarged scale. Three days after, with respect to the wells in the 24 well culture plate, the presence or absence of human antibody to *Pseudomonas aeruginosa* in the culture supernatant was examined by the DIBA method. Among them, the cells in the wells in which the activity of human antibody to *Pseudomonas aeruginosa* was high in the culture supernatant were cultured in order on an enlarged scale to give EB virus transformed cell colonies 7N19N1, 7N19N2, 7N19N3, 7N19N4, 7N19N5 and 7N19N6 capable of producing human IgM antibody to group G *Pseudomonas aeruginosa*.

(5) Cell fusion:

Using $1.0 \times 10^7$ of a mixture of EB virus transformed cell colonies 7N19N1, 7 N19N3, and 7 N19N4 capable of producing human monoclonal IgM antibody to group G *Pseudomonas aeruginosa* and the same cell number of MP 4109, cell fusion was carried out in a manner similar to Example 27, (1). The fused cells were suspended in HA-O medium to adjust to a cell density of $1 \times 10^6$/ml, and 0.1 ml each per well was inoculated on a 96 well flat bottom culture plate (192 wells in total). The cells were subjected to stationary culture at 37° C. in the presence of 5% carbon dioxide gas. Four days after, 0.1 ml of HA-O medium was added thereto and thereafter, half of the volume of HA-O medium was replaced by fresh HA-O medium at 4 or 5 day intervals. With respect to the 37 wells where cells grew, the presence or absence of human antibody to *Pseudomonas aeruginosa* in the culture supernatant was determined by the DIBA method. The antibody activity was detected in the culture supernatant of the 37 wells. By cloning in a manner similar to Example 27, (3), 6 hybridomas of MP 5148, MP 5114, MP 5115, MP 5116, MP 5117 and MP 5118 capable of producing human monoclonal antibody reactive only with group G *Pseudomonas aeruginosa* were obtained.

MP 5114 was deposited in the Fermentation Research Institute of the Agency of Industrial Science and Technology of Japan under accession No. FERM BP-2269.

(6) Determination of amount of antibody produced:

An amount of antibody produced by 6 strains of MP 5148, MP 5114, MP 5115, MP 5116, MP 5117 and MP 5118 was measured in a manner similar to Example 27, (4).

In hybridomas of MP 5148, MP 5114, MP 5115, MP 5116, MP 5117 and MP 5118, $10^6$ cells secreted 10 μg, 18 μg, 10 μg, 12 μg, 11 μg and 15 μg of human IgM in the culture supernatant for 24 hours, respectively.

(7) Stability of cell line in continuous subculture:

Stability of the growth and antibody production of MP 5114 were examined in a manner similar to Example 27, (5).

MP 5114 showed almost the same growth curve with the cells at the beginning of cultivation and 3 months after the cultivation. The doubling time calculated from the growth curve was 24 hours. IgM secreted by $10^6$ cells for 24 hours was 18 μg at the beginning of cultivation, 12 μg one month after, 14 μg two months after and 15 μg three months after, indicating that there was no significant difference in the amount of antibody produced during continuous subculture for 3 months.

EXAMPLE 40

Cell Culture and Purification of Antibody (7)

The frozen cells of MP 5114 were thawed and cultured in 10% FCS medium on a large scale. After culturing the cells in NYSF 404 medium on a larger scale, the cells were suspended in 50 ml of NYSF 404 medium at a cell density of $5 \times 10^4$/ml. The cells were then inoculated on 1 flask (bottom area of 175 cm$^2$) followed by stationary culture at 37° C. for 5 days in the presence of 5% carbon dioxide gas. The cells were collected and suspended in 500 ml of NYSF 404 medium at a cell density of $5 \times 10^4$/ml. The suspension was then inoculated on one starring culture flask (Techne) followed by spinner culture at 37° C. for 5 days at 20 rpm in the presence of 5% carbon dioxide gas. From 485 ml of the culture, 480 ml of the supernatant was obtained by centrifugation (400×g, 20 minutes) and filtered through a membrane filter having a pore size of 0.22 micron.

The antibody was purified from the filtrate in a manner similar to Example 28. From 480 ml of the culture supernatant, the solution containing 11.9 mg of IgM (N8-2) was obtained.

EXAMPLE 41

Production of Hybridoma Capable of Producing Monoclonal Antibody to *Pseudomonas aeruginosa* (8)

(1) Cell fusion:

Using $4.5 \times 10^7$ each of MP 4109 and MP 5035, respectively, cell fusion was carried out in a manner similar to Example 27, (1).

After the fused cells were suspended in HA-O medium at a cell density of $1 \times 10^6$/ml, the suspension was inoculated on a 96 well flat bottom culture plate in 0.1 ml each per well (864 wells in total). The cells were subjected to stationary culture at 37° C. in the presence of 5% carbon dioxide gas. Four days after, 0.1 ml of HA-O medium was added thereto and thereafter, half of the volume of HA-O medium was replaced by fresh HA-O medium at 3 to 5 day intervals. Four to five weeks after, cell growth was observed in 26 wells.

(2) Detection of antibody to *Pseudomonas aeruginosa*:

As the formalinized dry bacteria, group I *Pseudomonas aeruginosa* ATCC 27586 was used. Anti-*Pseudomonas aeruginosa* antibody was detected in a manner similar to Example 27, (2).

(3) Cloning:

Among the culture supernatant of 26 wells in which cell growth was observed, the production of human antibody to group I *Pseudomonas aeruginosa* was detected in the culture supernatant of 14 wells. The cells of the 14 wells were cloned in a manner similar to Example 27, (3). Two to four weeks after, with respect to the wells where cell growth was observed, the presence or absence of human antibody to group I *Pseudomonas aeruginosa* in the culture supernatant was examined by the DIBA method. The cells of the wells in which production of antibody reactive with group I *Pseudomonas aeruginosa* was detected were again cloned in a manner similar to Example 27,(3). By cloning twice, 2 strains of hybridomas MP 5156 and MP 5163 capable of producing human monoclonal antibody which is cross-reactive with groups I and D *Pseudomonas aeruginosa* in the serologic classification by the Serotyping Comittee for the Japan *Pseudomonas aeruginosa* Society were obtained.

MP 5156 was deposited in the Fermentation Research Institute of the Agency of Industrial Science and Technology of Japan under accession No. FERM BP-2339.

The hybridomas sufficiently grown in a 96 well flat bottom culture plate were cultured gradually on a larger scale. After the cells were suspended in a cell storing solution composed of 75% FCS, 10% DMSO and 15% RPMI 1640 medium at a density of $1 \times 10^6$/ml, the suspension was separately charged in a 2 ml freezing tube. After cooling to −20° C. at a rate of 1° C./min, the tube was stored freezingly in liquid nitrogen.

(4) Determination of amount of antibody produced:

The amount of antibody produced by 2 strains of MP 5156 and MP 5163 was measured in a manner similar to Example 27, (4).

In hybridomas of MP 5156 and MP 5163, $10^6$ cells secreted 15 μg and 10 μg of human IgM in the culture supernatant for 24 hours, respectively.

(5) Determination of stability of cell line in continuous subculture

Stability of the growth and antibody production of MP 5156 were examined in a manner similar to Example 27, (5).

MP 5156 showed almost the same growth curve with the cells at the beginning of cultivation and 3 months after the cultivation. The doubling time calculated from the growth curve was 23.6 hours. Furthermore, IgM secreted by $10^6$ cells for 24 hours was 15 μg at the beginning of cultivation, 11 μg one month after the initiation of cultivation, 12 μg 2 months after and 10 μg 3 months after, indicating that there was no significant difference in the amount of antibody produced during continuous subculture for 3 months.

EXAMPLE 42

Cell Culture and Purification of Antibody (8)

The frozen cells of MP 5156 were thawed and cultured in 10% FCS medium on a large scale. After culturing the cells in NYSF 404 medium on a larger scale, the cells were suspended in 500 ml of NYSF 404 medium at a cell density of $5 \times 10^4$/ml. The suspension was then inoculated on ten flasks (bottom area of 175 cm$^2$) followed by stationary culture at 37° C. for 5 days in the presence of 5% carbon dioxide gas. From the culture, 480 ml of the supernatant was obtained by centrifugation (400×g, 20 minutes) and filtered through a membrane filter having a pore size of 0.22 micron.

The antibody was purified from the filtrate in a manner similar to Example 28. From 480 ml of the culture supernatant, the solution containing 11.6 mg of IgM (N5-1) was obtained.

EXAMPLE 43

Test on Protective Activity of Human Monoclonal Antibody Against *Pseudomonas aeruginosa* Infectious Diseases (1)

The protective activity of the human monoclonal antibodies N4-2 and N10-1 obtained in Examples 28 and 30 against group A *Pseudomonas aeruginosa* infections was examined. Five to 10 mice (Balb/c, female) of 8 to 12 weeks of age in-one group were intraperitoneally administered 0.2 ml of each of solutions containing 50 ng, 500 ng, 5 μg and 50 μg of the human monoclonal antibody per mouse. Two hours after, the mice were challenged with a solution of group A *Pseudomonas aeruginosa* (F-1839) intraperitoneally. For the control group, physiological salt solution alone was administered instead of human monoclonal antibody. *Pseudomonas aeruginosa* was inoculated on heart infusion agar plate medium followed by culturing at 37° C. overnight. The grown cell colonies were scraped out and diluted with physiological salt solution. To the dilution was added 5% mucin to prepare the bacterial solution in a challenge dose by 8.7 times the 50% lethal dose ($LD_{50}$ value) per mouse. After challenge with *Pseudomonas aeruginosa*, 50% effective dose ($ED_{50}$ value) was determined from the survival ratio of mice in each administration group on day 7. N4-2 and N10-1 showed $ED_{50}$ of 0.25 μg and 0.2 μg, respectively. Each human monoclonal antibody had a high protective activity against group A *Pseudomonas aeruginosa* infections.

EXAMPLE 44

Test on Protective Activity of Human Monoclonal Antibody Against *Pseudomonas aeruginosa* Infectious Diseases (2)

The protective activity of the human monoclonal antibody N3-8 obtained in Example 6 against group B *Pseudomonas aeruginosa* infections was examined in a manner similar to Example 43. As the challenge bacteria, group B *Pseudomonas aeruginosa* (F-1860) was used and the bacterial amount was 20 times the $LD_{50}$ value. N3-8 showed $ED_{50}$ of 0.74 μg. The human monoclonal antibody had a high protective activity against group B *Pseudomonas aeruginosa* infections.

EXAMPLE 45

Test on Protective Activity of Human Monoclonal Antibody Against *Pseudomonas aeruginosa* Infectious Diseases (3)

The protective activity of the human monoclonal antibodies N1-5 and N11-1 obtained in Examples 8 and 10 against group E *Pseudomonas aeruginosa* infections was examined in a manner similar to Example 43. As the challenge bacteria, group E *Pseudomonas aeruginosa* (PA 103) was used and the bacterial amount was 13.5 times the $LD_{50}$ value. N1-5 and N11-1 showed $ED_{50}$ of 0.135 μg and 0.39 μg, respectively. Each human monoclonal antibody had a high protective activity against group E *Pseudomonas aeruginosa* infections.

EXAMPLE 46

Test on Protective Activity of Human Monoclonal Antibody Against *Pseudomonas aeruginosa* Infectious Diseases (4)

The protective activity of the human monoclonal antibodies N7-2 and N8-2 obtained in Examples 38 and 40 against group G *Pseudomonas aeruginosa* infections was examined in a manner similar to Example 43. As the challenge bacteria, group G *Pseudomonas aeruginosa* (P-28) was used and the bacterial amount was 8 times the $LD_{50}$ value. N7-2 and N8-2 showed $ED_{50}$ of 0.11 μg and 0.11 μg, respectively. Each human monoclonal antibody had a high protective activity against group G *Pseudomonas aeruginosa* infections.

EXAMPLE 47

Test on Protective Activity of Human Monoclonal Antibody Against *Pseudomonas aeruginosa* Infectious Diseases (5)

The protective activity of the human monoclonal antibody N5-1 obtained in Example 42 against group I *Pseudomonas aeruginosa* infections was examined in a manner similar to Example 43. As the challenge bacteria, group I *Pseudomonas aeruginosa* (F-1856) was used and the bacterial amount was 11.0 times the $LD_{50}$ value. N5-1 showed $ED_{50}$ of 3.5 μg. The human monoclonal antibody had a high protective activity against group I *Pseudomonas aeruginosa* infections.

EXAMPLE 48

Preparation of Liquid Composition (1)

N4-3 obtained in Example 28 and N10-1 obtained in Example 30 were, respectively, prepared in a concentration of 1 mg/ml with PBS(-) containing 0.2% (w/v) human serum albumin (Calbio). Each mixture was aseptically filtered through a membrane filter having a pore size of 0.22 micron. Each antibody solution was aseptically charged in vials, 1 ml/vial, to prepare each liquid composition. The compositions were allowed to stand at 4° C. and 37° C. for a month. Stability of the compositions during storage was determined by assaying antibody titer by ELISA using group A Pseudomonas aeruginosa (ATCC 27577) LPS as antigen.

The antibody titer was determined as follows.

LPS was dissolved (2 µg/ml) in 0.1M citrate buffer (pH 4.0) and 0.05 ml each of the solution was separately charged in each well of a 96 well plate for EIA (Greiner Co.). After allowing it to stand at 37° C. for 16 hours, LPS was adsorbed to the plate. Serial dilution of the liquid composition was reacted in the well at room temperature for 2 hours. Next, after reacting with peroxidase-conjugated goat anti-human IgM antibody (Tago) for 2 hours, a color was formed using as substrate 2,2'-azinobis(3-ethylbenzthiazolinesulfonic acid) (Sigma) and absorbance was measured at a wavelength of 414 nm. The dilution magnification showing absorbance of 0.1 was calculated by the method of least squares and this dilution value was made the antibody titer.

There was no difference in the antibody titers of N4-2 and N10-1 after allowing the solutions to stand between at 4° C. or 37° C. and at −80° C. as a control for a month. Each antibody activity was maintained.

EXAMPLE 49

Preparation of Liquid Composition (2)

A liquid composition of N3-8 obtained in Example 32 was prepared in a manner similar to Example 48. Stability of the liquid composition during storage was determined by assaying antibody titer by ELISA using group B Pseudomonas aeruginosa (ATCC 27578) LPS as antigen.

There was no difference in the antibody titer of N3-8 after allowing the solution to stand between at 4° C. or 37° C. and at −80° C. as a control for a month. The antibody activity of N3-8 was maintained.

EXAMPLE 50

Preparation of Liquid Composition (3)

Liquid compositions were prepared in a manner similar to Example 48 except for using N1-5 obtained in Example 34 and N11-1 obtained in Example 36. Stability of the liquid compositions during storage was determined by assaying antibody titer by ELISA using group E Pseudomonas aeruginosa (ATCC 27581) LPS as antigen.

There was no difference in the antibody titers of N1-5 and N11-1 after allowing them to stand between at 4° C. or 37° C. and at −80° C. as a control for a month. Each antibody activity of the liquid compositions was maintained.

EXAMPLE 51

Preparation of Liquid Composition (4)

Liquid compositions were prepared in a manner similar to Example 48 except for using N7-2 obtained in Example 38 and N8-2 obtained in Example 40. Stability of the liquid compositions during storage was determined by assaying antibody titer by ELISA using group G Pseudomonas aeruginosa (ATCC 27584) LPS as antigen.

There was no difference in the antibody titers of N7-2 and N8-2 after allowing them to stand between at 4° C. or 37° C. and at −80° C. as a control for a month. Each antibody activity of the liquid compositions was maintained.

EXAMPLE 52

Preparation of Liquid Composition (5)

Liquid composition of N5-1 obtained in Example 42 was prepared in a manner similar to Example 48. Stability of the liquid composition during storage was determined by assaying the antibody titer by ELISA using group I Pseudomonas aeruginosa (ATCC 27586) LPS as antigen.

There was no difference in the antibody titer of N5-1 after allowing it to stand between at 4° C. or 37° C. and at −80° C. as a control for a month. The antibody activity of N5-1 was maintained.

EXAMPLE 53

Preparation of Lyophilized Composition (1)

N4-2 obtained in Example 28 and N10-1 obtained in Example 30 were, respectively, prepared in a concentration of 1 mg/ml with PBS(-) containing 0.2% (w/v) human serum albumin (Cablio). Each mixture was aseptically filtered through a membrane filter having a pore size of 0.22 micron. Each antibody solution was aseptically charged in vials, 1 ml/vial, and lyophilized to prepare each lyophilized composition. The lyophilized compositions, immediately after freeze drying and after allowing them to stand at 4° C. and 37° C. for 3 months and 6 months, were again dissolved in distilled water. The antibody titer was determined in a manner similar to Example 48 by ELISA using group A Pseudomonas aeruginosa (ATCC 27577) LPS as antigen. There was no difference in the antibody titers of N4-2 and N10-1 between the lyophilized compositions redissolved and the non-lyophilized compositions used for comparison. Each antibody activity was maintained.

EXAMPLE 54

Preparation of Lyophilized Composition (2)

Lyophilized composition of N3-8 obtained in Example 32 was prepared in a manner similar to Example 53. Stability of the lyophilized composition was determined by assaying the antibody titer by ELISA using group B Pseudomonas aeruginosa (ATCC 27578) LPS as antigen.

There was no difference in the antibody titer of the solution of N3-8 between the lyophilized composition redissolved and the non-lyophilized composition used for comparison. The antibody activity was maintained.

EXAMPLE 55

Preparation of Lyophilized Composition (3)

Lyophilized compositions were prepared in a manner similar to Example 53 except for using N1-5 obtained in Example 34 and N11-1 obtained in Example 36. Stability of the lyophilized compositions was determined by assaying the antibody titer by ELISA using group E *Pseudomonas aeruginosa* (ATCC 27581) LPS as antigen.

There was no difference in the antibody titers of N1-5-and N11-1 between the lyophilized compositions redissolved and the non-lyophilized compositions used for comparison. Each antibody activity was maintained.

EXAMPLE 56

Preparation of Lyophilized Composition (4)

Lyophilized compositions were prepared in a manner similar to Example 53 except for using N7-2 obtained in Example 38 and N8-2 obtained in Example 40. Stability of the lyophilized compositions was determined by assaying the antibody titer by ELISA using group G *Pseudomonas aeruginosa* (ATCC 27584) LPS as antigen.

There was no difference in the antibody titers of the solutions of N7-2 and N8-2 between the lyophilized compositions redissolved and the non-lyophilized compositions used for comparison. Each antibody activity was maintained.

EXAMPLE 57

Preparation of Lyophilized Composition (5)

Lyophilized composition of N5-1 obtained in Example 42 was prepared in a manner similar to Example 53. Stability of the lyophilized composition was determined by assaying the antibody titer by ELISA using group I *Pseudomonas aeruginosa* (ATCC 27586) LPS as antigen.

There was no difference in the antibody titer of N5-1 between the lyophilized composition redissolved and the non-lyophilized composition used for comparison. The antibody activity was maintained.

EFFECTS OF THE INVENTION

By use of the human monoclonal antibodies according to the present invention singly or in combination of two or more or in combination with other human antibodies, excellent prophylactic and therapeutic effects against *Pseudomonas aeruginosa* infectious diseases can be achieved.

To be notable in the present invention is that the present inventors have found for the first time that antigens recognized by the single human monoclonal antibodies having cross reactivity between *Pseudomonas aeruginosa* of different serotypes are present on an O-specific polysaccharide chain which is a serotype specific antigenic site and the human monoclonal antibodies exhibit prophylactic and therapeutic effects against *Pseudomonas aeruginosa* infectious diseases in an extremely low concentration and low dose. The present inventors have further found that protective spectrum can be broadened by single use and such thus makes it possible to reduce the kind of human monoclonal antibodies to be mixed in production of preparations containing the human monoclonal antibodies to O-antigens of *Pseudomonas aeruginosa*.

In Published Unexamined Japanese Patent Application No. 155398/1986, human monoclonal antibody showing reactivity to bacteria of serotype 2, 7 and 13 according to the Homma's classification are described but all of the bacteria recognized by the monoclonal antibody are classified into the same serotype according to the serological classification of the Serotyping Committee for the Japan *Pseudomonas aeruginosa* Society and the Lanyi's classification. The human monoclonal antibody is considered to be an antibody merely recognizing substrain in the same serotype but is different in property from the single human monoclonal antibody which recognizes *Pseudomonas aeruginosa* of a plurality of different serotypes referred to in the present invention.

The term showing cross reactivity between serotypes of *Pseudomonas aeruginosa* as used in the present invention refers to a case in which a plurality of *Pseudomonas aeruginosae* with which a human monoclonal antibody shows reactivity are not classified into only one serotype in any of serological classifications hitherto known. In case that a plurality of *Pseudomonas aeruginosa* with which a human monoclonal antibody shows reactivity are classified into a plurality of serotypes only in a specific serological classification, such a case is not referred to as showing cross reactivity between serotypes of *Pseudomonas aeruginosa* but this shows that the human monoclonal antibody is reactive merely with substrains in the same serotype.

Furthermore in the human monoclonal antibodies of the present invention, type of immunoglobulin is IgM or IgG but may also be IgA, needless to say.

By using the novel parent cell line of the present invention, human hybridomas with human antibody-producing cells can be produced.

What is notable in the present invention is that the human hybridomas produced by cell fusion between the novel parent cell lines of the present invention, MP 4109, MP 4112 and MP 4126, and human antibody-producing cells contain no human immunoglobulin heavy chain derived from the parent cell lines at all in the resulting human monoclonal antibodies. It is particularly of great significance in the case of industrially utilizing human monoclonal antibodies produced by human hybridomas that a parent cell line for producing human hybridomas do not synthesize human immunoglobulin heavy chain. The human hybridomas produced by cell fusion between the heavy chain-non-producing parent cell line of the present invention and human antibody-producing cells of the IgA type, IgG type, IgM type, type or IgD type do not synthesize heavy chain derived from the parent cell lines so that the desired antibodies of the IgA type, IgG type, IgM type, IgE type or IgD type can be readily purified. The human hybridomas produced by cell fusion between the heavy chain-non-producing parent cell line of the present invention and human antibody-producing cells are free of any chance to produce antibodies in which heavy chain derived from the parent cells is recombined with the desired antibodies. Furthermore, the human hybridomas produced by cell fusion between MP 4126 and antibody-producing cells synthesize only human immunoglobulin derived from human antibody-producing cells so that the desired antibodies can be readily purified. The use of the novel parent cell lines of the present invention can be appropriately selected depending upon the Type of human antibody-producing cells or purpose of using the antibodies produced.

The parent cell line of the present invention can be fused with a variety of human antibody-producing cells of different origins. After the cell fusion, the human hybridomas produced can be selectively proliferated by their own selectivity characteristics. As the human antibody-producing cells, there may be used, for example, antibody-producing cells isolated from spleen, lymph node, tonsile, peripheral blood, etc. of healty donor or patients with various diseases; cell masses obtained by transforming these antibody-producing cells with EB virus and single EB virus transformant obtained from these transformed cell masses by cloning. Furthermore, human antibody-producing cells in which a high blood antibody titer to a specific antigen is induced by immunization with a specific antigen, antibody-producing cells obtained by stimulating and proliferating by culturing human antibody-producing cells (B cells) in a medium supplemented with factors such as poke weed mitogen (PWM), etc. and a specific antigen for several days, and the like, may also be used as the human antibody-producing cells for cell fusion.

By cell fusion between the novel parent cell lines of the present invention and human antibody-producing cells, human monoclonal antibodies which can be used for diagnosis, prophylaxis and treatment of various diseases can be produced. For example, it is now possible to produce human monoclonal antibodies to viruses such as cytomegalovirus (CMV), human T cell leukemia virus (HTLV), herpes simplex virus (HSV), varicella-zoster virus (VZV), hepatitis B virus (HBV), influenza virus, RS virus (RSV), etc.; bacteria such as *Pseudomonas aeruginosa*, pathogenic *Escherichia coli*, *Haemophilus influenzae*, *Diplococcus pnumoniae*, *Staphylococcus aureus*, etc.; fungi such as Aspergirus, Candida, etc. Human monoclonal antibodies which are applicable to a wide range such as classification of cells, electrophoretic analysis, purification of substance, histology, cellology, etc., in addition to diagnosis and therapy. For example, human monoclonal antibodies to cancer antigen, toxin such as exotoxin A, etc. produced by *Pseudomonas aeruginosa*, various allergens such as cedar pollens, hormones, physiologically active proteins, histocompatible antigens, etc. all now possible. The globulin class of antibodies produced by the human antibody-producing cells may be any one of the various isotypes including IgG, IgM, IgA, IgD and IgE.

Furthermore, the parent cell line of the present invention can be used not only as the parent cell line for cell fusion but also as host cells for producing various proteins by transfecting and expressing various genes. In addition, the parent cell line can also be used as cells for preparing-human antibody genes by producing human hybridomas with human antibody-producing cells.

The novel parent cell line of the present invention can impart a high antibody-secreting ability to the human hybridomas produced by cell fusion. By this property, the time period for incubation can be shortened and production costs can be reduced in the case of producing human monoclonal antibodies through culturing the human hybridomas produced in large quantities.

Either by selecting the parent cell line of the present invention or by selecting after induction of mutation, a new human immunoglobulin-non-producing cell line can be obtained. Alternatively, the parent cell line of the present invention is fused with human myeloma cells or human lymphoblasts to create a new parent cell line. The parent cell line of the present invention can also be directed to a new parent cell line by introducing a foreign gene for imparting selectivity characteristics or to induce mutation. For example, a plasmid having a gene resistant to chamicals such as neomycin, etc. can be introduced into the parent cell line or the parent cell line can be fused with cells having a gene resistant thereto.

While the invention has been described in detail and with reference to specific embodiments thereof, it is apparent to one skilled in the art that various changes and modifications can be made therein without departing from the spirit and the scope of the present invention.

The human monoclonal antibody, produced by culturing the human-human hybridoma of the present invention in a suitable medium for production and purified from the culture, is used singly or in a combination of two or more kinds of the human monoclonal antibody or in combination with other human antibodies, whereby excellent prophylactic and therapeutic effects against *Pseudomonas aeruginosa* infectious diseases can be exhibited.

The human-human hybridoma of the present invention is capable of producing a human monoclonal antibody reactive with at least one serological bacteria which are the major causative bacteria of *Pseudomonas aeruginosa* infectious diseases, the inventive human-human hybridoma can be continuously subcultured and grown stably in fetal calf serum-supplemented medium for animal tissue culture over long periods of time. In addition, the human-human hybridoma is also capable of producing the antibody in large quantities even in serum-free medium which is free of danger that the system might be contaminated by unknown impurities derived from the medium during the course of purifying the human monoclonal antibody from the culture. Thus, the human-human hybridoma is most suited for obtaining the human monoclonal antibody which can be raw materials for preparing compositions for prophylaxis and therapy of *Pseudomonas aeruginosa* infectious diseases. That is, the novel human-human hybridoma of the present invention has an enhanced ability of secreting the antibody can shorten the period for incubation, and thus can reduce production costs, when the human monoclonal antibody is produced by culturing on a large scale.

Furthermore, the human-human hybridoma of the present invention can be not only used as the cell line for producing human monoclonal antibody but also used as raw cells for preparing human antibody gene in the case of transfecting and expressing globulin gene in other host cells or microorganisms. The following deposits were made at National Institute of Bioscience and Human Technology, Agency of Industrial Science and Technology, Ministry of International Trade and Industry, 1-3, Higashi 2-chome, Tsukuba-shi, Ibaraki-ken 305, Japan:

| Deposit No. FERM | Depositor's ref. | Date Deposited |
|---|---|---|
| BP-1598 | MP 5035 | December 9, 1987 |
| BP-1596 | MP 5038 | December 7, 1987 |
| BP-1600 | MP 5050 | December 9, 1987 |
| BP-1599 | MP 5046 | December 9, 1987 |
| BP-2128 | MP 4112 | October 27, 1988 |
| BP-2129 | MP 4109 | October 27, 1988 |
| BP-2615 | MP 4126 | September 26, 1989 |
| BP-2271 | MP 5136 | February 7, 1989 |
| BP-2268 | MP 5097 | February 7, 1989 |
| BP-2273 | MP 5140 | February 7, 1989 |
| BP-2269 | MP 5114 | February 7, 1989 |

What is claimed is:

1. A transformed cell line selected from the group consisting of FERM BP-1599, FERM BP-1598, FERM BP-1596, and FERM BP-1600.

2. A human monoclonal antibody which is specific for *Pseudomonas aeruginosa* groups A and F, produced by a cell line FERM BP-1599 and having the binding characteristics thereof.

3. A human monoclonal antibody which is specific for

*Pseudomonas aeruginosa* groups D and I, produced by a cell line FERM BP-1598 and having the binding characteristics thereof.

4. A human monoclonal antibody which is specific for *Pseudomonas aeruginosa* groups E and F, produced by a cell line FERM BP-1596 and having the binding characteristics thereof.

5. A human monoclonal antibody which is specific for *Pseudomonas aeruginosa* groups G and H, produced by a cell line FERM BP-1600 and having the binding characteristics thereof.

* * * * *